(12) United States Patent
Cai et al.

(10) Patent No.: US 7,589,095 B2
(45) Date of Patent: Sep. 15, 2009

(54) 4-PHENYL-PYRIMIDINE-2-CARBONITRILE DERIVATIVES

(75) Inventors: Jiaqiang Cai, Newhouse (GB); Zoran Rankovic, Newhouse (GB); Jennifer Helen Moir, Newhouse (GB)

(73) Assignee: N.V. Organon, Oss (NL)

( * ) Notice: Subject to any disclaimer, the term of this patent is extended or adjusted under 35 U.S.C. 154(b) by 151 days.

(21) Appl. No.: 11/628,623

(22) PCT Filed: Jun. 9, 2005

(86) PCT No.: PCT/EP2005/006266

§ 371 (c)(1),
(2), (4) Date: Feb. 1, 2007

(87) PCT Pub. No.: WO2005/121106

PCT Pub. Date: Dec. 22, 2005

(65) Prior Publication Data

US 2008/0090813 A1    Apr. 17, 2008

(30) Foreign Application Priority Data

Jun. 11, 2004 (EP) ................................. 04253491
Dec. 23, 2004 (EP) ................................. 04106949

(51) Int. Cl.
*C07D 239/28* (2006.01)
*A61K 31/505* (2006.01)
*A61P 9/10* (2006.01)
*A61P 19/02* (2006.01)
*A61P 19/10* (2006.01)
*A61P 29/00* (2006.01)

(52) U.S. Cl. ....................... 514/256; 514/269; 544/319; 544/326

(58) Field of Classification Search ................. 544/319, 544/326; 514/269, 256
See application file for complete search history.

(56) References Cited

U.S. PATENT DOCUMENTS 7,326,715 B2 * 2/2008 Rankovic et al. ............ 514/269

FOREIGN PATENT DOCUMENTS

| EP | 0330057 A | 8/1989 |
|----|-----------|--------|
| WO | WO 02/064571 A | 8/2002 |
| WO | WO 03/020278 | 3/2003 |
| WO | WO 03/020287 | 3/2003 |
| WO | WO 03/020721 | 3/2003 |
| WO | WO 2004/000819 A | 12/2003 |
| WO | WO 2004/000843 | 12/2003 |

OTHER PUBLICATIONS

Yamanaka et al., Synthesis 8, 681-683, 1984; CA 102: 78913, 1985.*
Hou et al. Arthritis & Rheumatism, 46(3): 663-674, 2002.*
Honma et al., Chemical & Pharmaceutical Bulletin (1982), 30(12), 4314-24.*
Caton et al., Journal of the Chemical Society [Section] C: Organic (1967), (13), 1204-9.*
Bossard, et al., "Proteolytic Activity of Human Osteoclast Cathepsin K," *J. Biol. Chem. 271*, 1996, 12517-12524.
Bromme, et al., "Human Cathepsin O2, a Novel Cysteine Protease Highly Expressed in Osteoclastomas and Ovary Molecular Cloning, Sequencing and Tissue Distribution," *Biol. Chem. Hoppe-Seyler, 376*, 1995, 379-384.
Bromme, et al., "Human Cathepsin O2, a Matrix Protein-degrading Cysteine Protease Expressed in Osteoclasts," *J. Biol. Chem.,271*, 1996, 2126-2132.
Kafienah, et al., "Human cathepsin K cleaves native type I and II collagens at the N-terminal end of the triple helix," *Biochem. J. 331*, 1998, 727-732.
Lindstedt, et al., "Cathepsins F and S block $HDL_3$-induced cholesterol efflux from macrophage foam cells," *Biochem. Biophys. Research Comm. 312*, 2003, 1019-1024.
Maciewicz, et al., "A comparison of four cathepsins (B, L, N and S) with collagenolytic activity from rabbit spleen," *Biochem. J. 256*, 1988, 433-440.
Saegusa, et al., "Cathepsin S inhibitor prevents autoantigen presentation and autoimmunity," *J. Clin. Invest. 110*, 2002, 361-369.
Shi, et al., "Cystatin C deficiency in human atherosclerosis and aortic aneurysms," *J. Clin. Invest. 104*, 1999, 1191-1197.
Shi, et al., "Molecular Cloning and Expression of Human Alveolar Macrophage Cathepsin S, an Elastinolytic Cysteine Protease," *J. Biol. Chem., 267*, 1992, 7258-7262.
Sukhova, et al., "Deficiency of cathepsin S reduces atherosclerosis in LDL receptor-deficient mice," *J. Clin. Invest. 111*, 2003, 897-906.
Sukhova, et al., "Expression of the Elastolytic Cathepsins S and K in Human Atheroma and Regulation of their Production in Smooth Muscle Cells," *J. Clin. Invest. 102*, 1998, 576-583.
Xin, et al., "The Specificity and Elastinolytic Activities of Bovine Cathepsins S and H," *Arch. Biochem. Biophys., 299*, 1992, 334-339.
Written Opinion and International Search Report PCT/EP2005/006266 dated Aug. 29, 2005.
English language abstract of EP 0330057A.

* cited by examiner

*Primary Examiner*—Venkataraman Balasubramanian
(74) *Attorney, Agent, or Firm*—Susan Hess

(57) ABSTRACT

The invention relates to 4-phenyl-pyrimidine-2-carbonitrile derivatives having the general formula I Formula I wherein each of the substituents is given the definition as set forth in the specification and claims, or a pharmaceutically acceptable salt thereof. The invention also relates to pharmaceutical compositions comprising the derivatives as well as to the use thereof in the treatment of osteoporosis, atherosclerosis, inflammation and immune disorders, such as rheumatoid arthritis, and chronic pain, such as neuropathic pain.

23 Claims, No Drawings

4-PHENYL-PYRIMIDINE-2-CARBONITRILE DERIVATIVES

The invention relates to 4-phenyl-pyrimidine-2-carbonitrile derivatives, to pharmaceutical compositions comprising the same, as well as to the use of these derivatives for the preparation of a medicament for the treatment of cathepsin K and cathepsin S related diseases such as atherosclerosis, bone diseases such as osteoporosis, inflammation and immune disorders such as rheumatoid arthritis and multiple sclerosis, and chronic pain such as neuropathic pain.

Cysteine proteases represent a class of peptidases characterised by the presence of a cysteine residue in the catalytic site of the enzyme, and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, rheumatoid arthritis, osteoarthritis, osteoporosis, tumors, coronary disease, atherosclerosis, autoimmune diseases and infectious diseases.

Cathepsin K has strong collagenolytic, elastase and gelatinase activities (Bromme et al., J. Biol, Chem, 271, 2126-2132, 1996) and is predominantly expressed in osteoclasts (Bromme and Okamoto, Biol. Chem. Hopp-Seyler, 376, 379-384, 1995). It cleaves key bone matrix proteins, including collagen type I and II (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminuation of osteoclast mediated bone resorption. Cathepsin K inhibitors may therefore represent new therapeutic agents for the treatment of disease states in man such as osteoporosis.

Sukhova et al (J. Clin. Invest. 102, 576-583, 1998) have thereafter demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and/or S at sites of plaques prone to rupture may thus represent an effective way of preventing such events. Like cathepsin K, cathepsin S also has potent elastolytic (Arch. Biochem. Biophys., 299, 334-339, 1992; J. Biol. Chem., 267, 7258-7262, 1992) and collagenolytic activities (Biochem. J., 256, 433-440, 1998). Diseased human arteries overexpress both cathepsin K and S and exhibit a reciprocal deficiency of cystatin C, the most abundant endogenous inhibitor of cysteine proteases (J. Clin. Invest. 102, 576-583, 1998; J. Clin. Invest. 104, 1191-1197, 1999). Sukhova et al (J. Clin. Invest. 111, 897-906, 2003) have demonstrated that deficiency of cathepsin S reduces atherosclerosis in LDL receptor-deficient mice. Bromme et al (Biochem. Biophys. Research Comm. 312, 1019-1024, 2003) also demonstrated that both Cathepsin K and S are capable of degrading HDL3 and lipid free apoA-1 in vitro. This further indicates cathepsin K and S as therapeutic target for atherosclerosis.

Cathepsin S has been shown to be a key enzyme involved in invariant chain processing in human and mouse antigen-presenting cells (J. Clin. Invest. 110, 361-369, 2002). This invariant chain processing regulates MHC class II function and is associated with inflammation and autoimmnune disorders. Saegusa et al (J. Clin. Invest. 110, 361-369, 2002) have thereafter demonstrated that inhibition of cathepsin S in vivo alters autoantigen presentation and development of organ-specific autoimmunity.

It is also disclosed in International Patent Application WO 03/020287 that mRNA for cathepsin S is up-regulated in animal models of chronic pain and that administration of cathepsin S inhibitors causes a reversal of mechanical hyperalgesia in these animals.

4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO04/000819 (ASTRAZENECA AB) as Cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB).

It has now been found that 4-phenyl-pyrimidine-2-carbonitrile derivatives having the general formula I

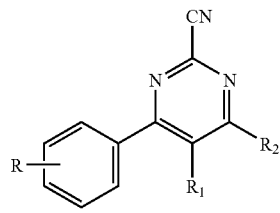

Formula I wherein

R represents 1-3 optional substituents independently selected from $(C_{1-6})$alkyl (optionally substituted with one or more halogens), $(C_{1-6})$alkyloxy (optionally substituted with one or more halogens), cyano, halogen, hydroxy, nitro, $(C_{3-6})$cycloalkyl, $CO(C_{1-6})$alkyl, $S(C_{1-6})$alkyl, $SO(C_{1-6})$alkyl, $SO_2(C_{1-6})$alkyl, $SO_2NH(C_{1-8})$alkyl, $SO_2NH_2$, $NHCO(C_{1-8})$alkyl and $CO_2H$; or 2 substituents R on adjacent positions represent together $OCH_2O$, $OCH_2CH_2O$ or $CH_2CH_2O$;

$R_1$ is H or $(C_{1-6})$alkyl;

$R_2$ is $(C_{2-6})$alkyl, optionally substituted with OH, $(C_{1-4})$alkyloxy, $(C_{6-10})$aryloxy, $(C_{6-10})$aryl$(C_{1-4})$alkyloxy, one or more halogens, $NR_3R_4$, $CO_2H$ or $CONR_6R_7$;

$R_3$ and $R_4$ are independently H, $(C_{1-8})$alkyl [optionally substituted with one or more halogens, $(C_{1-4})$alkyloxy or $(C_6-C_{10})$aryloxy], $(C_{3-8})$cycloalkyl [optionally substituted with one or more halogens], $(C_{1-4})$alkyl substituted with a 4-8 membered saturated heterocyclic ring comprising a heteroatom selected from O, S and $NR_5$, a 4-8 membered saturated heterocyclic ring comprising a heteroatom selected from O, S and $NR_5$, $(C_6-C_{10})$aryl, $(C_{2-9})$heteroaryl [optionally substituted with 1-3 substituents selected from halogen, $CF_3$, $(C_{1-4})$alkyl and $(C_{1-4})$alkyloxy], $(C_{6-10})$aryl$(C_{1-4})$alkyl or $(C_{2-9})$heteroaryl$(C_{1-4})$alkyl; or $R_3$ and $R_4$ together with the nitrogen to which they are bound form a 4-8 membered saturated heterocyclic ring, optionally substituted with one or more halogens or with $CONR_8R_9$, and optionally further comprising 1 or more heteroatoms selected from O, S and $NR_5$; or $R_3$ is H or $(C_{1-4})$alkyl; and $R_4$ is $(C_{1-4})$alkyl substituted with $CONR_8R_9$, $COOR_{10}$; $NR_8$, $R_9$, $NR_8COR_9$, or $NR_8CONR_9R_{10}$;

$R_5$ is H, $(C_{1-4})$alkyl [optionally substituted with $(C_{3-8})$cycloalkyl, $(C_{6-10})$aryl or $(C_{2-5})$-heteroaryl], $(C_{3-8})$cycloalkyl, $(C_6-C_{10})$aryl or $(C_{2-5})$heteroaryl;

$R_6$ and $R_7$ are independently H, $(C_{1-4})$alkyl or a 4-8 membered saturated heterocyclic ring comprising a heteroatom selected from O, S and $NR_5$; or $R_6$ and $R_7$ together with the nitrogen to which they are bound form a 4-8 membered saturated heterocyclic ring, optionally substituted with one or more halogens, and optionally further comprising 1 or more heteroatoms selected from O, S and $NR_5$;

$R_8$ and $R_9$ are independently H or $(C_{1-4})$alkyl; or $R_8$ and $R_9$ together with the atoms to which they are bound form a 4-8 membered saturated heterocyclic ring, optionally comprising 1 or more heteroatoms selected from O, S and $NR_5$:

$R_{10}$ is H or $(C_{1-4})$alkyl;

or a pharmaceutically acceptable salt thereof, are inhibitors of cathepsin K and cathepsin S and can therefore be used for the preparation of a medicament for the treatment of cathepsin K and cathepsin S related disorders, e.g. atherosclerosis, bone diseases such as osteoporosis, inflammation and immune disorders such as rheumatoid arthritis and multiple sclerosis, and chronic pain such as neuropathic pain.

A further aspect of the invention concerns 4-phenyl-pyrimidine-2-carbonitrile derivatives having the general formula I

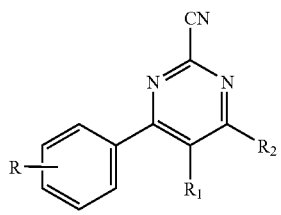

Formula I wherein

R represents 1-3 optional substituents independently selected from $(C_{1-6})$alkyl [optionally substituted with one or more halogens], $(C_{1-6})$alkyloxy [optionally substituted with one or more halogens], cyano and halogen;

$R_1$ is H or $(C_{1-6})$alkyl;

$R_2$ is $(C_{2-6})$alkyl, optionally substituted with OH, $(C_{1-4})$alkyloxy, one or more halogens, or $NR_3R_4$;

$R_3$ and $R_4$ are independently H, $(C_{1-8})$alkyl [optionally substituted with one or more halogens], $(C_{3-8})$cycloalkyl [optionally substituted with one or more halogens], a 4-8 membered saturated heterocyclic ring comprising a heteroatom selected from O, S and $NR_5$, $(C_{6-10})$aryl, $(C_{2-9})$heteroaryl, $(C_{6-10})$aryl$(C_{1-4})$alkyl or $(C_{2-9})$heteroaryl-$(C_{1-4})$alkyl; or $R_3$ and $R_4$ together with the nitrogen to which they are bound form a 4-8 membered saturated heterocyclic ring, optionally substituted with one or more halogens, and optionally further comprising 1 or more heteroatoms selected from O, S and $NR_5$;

$R_5$ is H, $(C_{1-4})$alkyl [optionally substituted with $(C_{3-8})$cycloalkyl, $(C_{6-10})$aryl or $(C_{2-5})$-heteroaryl], $(C_{3-8})$cycloalkyl, $(C_6-C_{10})$aryl or $(C_{2-5})$heteroaryl; or a pharmaceutically acceptable salt thereof.

The term $(C_{1-6})$alkyl, as used in the definition of formula I, means a branched or unbranched alkyl group having 1-6 carbon atoms, like hexyl, pentyl, 3-methyl-butyl, butyl, isobutyl, tertiary butyl, propyl, isopropyl, ethyl and methyl.

The term $(C_{2-6})$alkyl likewise means a branched or unbranched alkyl group having 2-6 carbon atoms, like hexyl, pentyl, 3-methyl-butyl, butyl, isobutyl, tertiary butyl, propyl, isopropyl and ethyl. A preferred $(C_{2-6})$alkyl, as used in the definition of $R_2$ in formula I, is n-propyl.

The term $(C_{1-4})$alkyl means a branched or unbranched alkyl group having 1-4 carbon atoms, like butyl, isobutyl, tertiary butyl, propyl, isopropyl, ethyl and methyl.

The term $(C_{1-8})$alkyl means a branched or unbranched alkyl group having 1-8 carbon atoms, like octyl, heptyl, hexyl, pentyl, 3-methyl-butyl, butyl, isobutyl, tertiary butyl, propyl, isopropyl, ethyl and methyl.

The term $(C_{3-6})$cycloalkyl means a cycloalkyl group having 3-6 carbon atoms, such as cyclohexyl, cyclopentyl, cyclobutyl and cyclopropyl.

The term $(C_{3-8})$cycloalkyl likewise means a cycloalkyl group having 3-8 carbon atoms, such as cyclooctyl, cycloheptyl, cyclohexyl, cyclopentyl, cyclobutyl and cyclopropyl.

The term $(C_{6-10})$aryl means a radical derived from an aromatic group having 6-10 carbon atoms like for example phenyl and naphthyl.

The term $(C_{6-10})$aryl$(C_{1-4})$alkyl means a $(C_{1-4})$alkyl group which is substituted with a $(C_6-C_{10})$aryl group, like for example the benzyl group.

The term $(C_{2-9})$heteroaryl means a 5 or 6-membered cyclic aromatic group having 1-3 heteroatoms selected from nitrogen, oxygen or sulfur, and to which another 5 or 6-membered (hetero)aromatic ring can be fused. Examples of such heteroaryl groups are pyridyl, imidazolyl, pyrazolyl, pyrimidinyl, thiazolyl, isothiazolyl, oxazolyl, isoxazolyl, thienyl, oxadiazolyl, quinolyl, isoquinolyl, benzothiazolyl, benzimidazolyl, and the like. Preferred heteroaryl groups are 2-pyridyl and 3-pyridyl.

The term $(C_{2-5})$heteroaryl means a 5 or 6-membered cyclic aromatic group having 1-3 heteroatoms selected from nitrogen, oxygen or sulfur. Examples of such heteroaryl groups are pyridyl, imidazolyl, pyrazolyl, pyrimidinyl, thiazolyl, isothiazolyl, oxazolyl, isoxazolyl, thienyl, oxadiazolyl, and the like. Preferred heteroaryl groups are 2-pyridyl and 3-pyridyl.

The term $(C_{2-9})$heteroaryl$(C_{1-4})$alkyl means a $(C_{1-4})$alkyl group which is substituted with a $(C_{2-9})$heteroaryl group, like for example a pyridin-4-ylmethyl group.

In the definition of formula I $R_3$ and $R_4$, and/or $R_6$ and $R_7$, and/or $R_8$ and $R_9$, can form together with the nitrogen to which they are bound a 4-8 membered saturated heterocyclic ring, such as an azetidine, a pyrrolidine, a piperidine, or a 1H-azepine ring. Such rings may contain 1 or more additional heteroatoms selected from O, S or $NR_5$ to form rings such as a morpholine, a thiomorpholine, a hexahydro-1,4-oxazepine, a piperazine, a homopiperazine, an imidazolidine or a tetrahydrothiazole ring. The term halogen means F, Cl, Br, or I. When halogen is a substituent at an alkyl group, F is preferred. A preferred halogen substituted alkyl group is trifluoromethyl.

Preferred in the invention are those 4-phenyl-pyrimidine-2-carbonitrile derivatives according to formula I wherein $R_2$ is $(C_{2-6})$alkyl substituted with OH, $(C_{1-4})$alkyloxy, one or more halogens, or $NR_3R_4$.

Further preferred are the compounds wherein $R_2$ is propyl substituted at the 3-position with $NR_3R_4$.

More preferred are the derivatives of formula I wherein the 4-phenyl group comprises a trifluoromethyl substituent at a meta position.

Especially preferred 4-phenyl-pyrimidine-2-carbonitrile derivatives of the invention are:
4-(3-hydroxy-1-propyl)-6-(3-trifluoromethylphenyl)-pyrimidine-2-carbonitrile;
4-(3-(piperidin-1-yl)propyl)-6-(3-trifluoromethylphenyl)-pyrimidine-2-carbonitrile;
4-[3-(1-ethyl-propylamino)-propyl]-6-(3-trifluoromethylphenyl)-pyrimidine-2-carbonitrile;
4-[3-(4-methyl-[1,4]diazepan-1-yl)-propyl]-6-(3-trifluoromethylphenyl)-pyrimidine-2-carbonitrile;
4-(3-cyclohexylamino-propyl)-6-(3-trifluoromethylphenyl)-pyrimidine-2-carbonitrile;
4-{3-[methyl-(1-methyl-piperidin-4-yl)-amino]-propyl}-6-(3-trifluoromethylphenyl)-pyrimidine-2-carbonitrile;
4-[3-(4-methyl-piperazin-1-yl)-propyl]-6-(3-trifluoromethylphenyl)-pyrimidine-2-carbonitrile
4-(3-Isopropylamino-propyl)-6-(3-trifluoromethylphenyl)-pyrimidine-2-carbonitrile;
4-[3-(4-Pyridin-2-yl-piperazin-1-yl)-propyl]-6-(3-trifluoromethylphenyl)-pyrimidine-2-carbonitrile;
4-[3-(carbamoylmethylamino)-propyl]-6-(3-trifluoromethylphenyl)-pyrimidine-2-carbonitrile;
4-[3-(carboxymethylamino)-propyl]-6-(3-trifluoromethylphenyl)-pyrimidine-2-carbonitrile;
4-[3-(2-dimethylaminoethylamino)-propyl]-6-(3-trifluoromethylphenyl)-pyrimidine-2-carbonitrile;
4-[3-(2-acetylaminoethylamino)-propyl]-6-(3-trifluoromethylphenyl)-pyrimidine-2-carbonitrile;
4-{3-[2-(2-oxo-imidazolidin-1-yl)-ethylamino]-propyl}-6-(3-trifluoromethylphenyl)-pyrimidine-2-carbonitrile;
4-(3,4-dimethylphenyl)-6-[3-(methylcarbamoylmethylamino)-propyl]-pyrimidine-2-carbonitrile;
4-[3-(2-acetylaminoethylamino)-propyl]-6-(3,4-dimethylphenyl)-pyrimidine-2-carbonitrile;
4-(3,4-dimethyl-phenyl)-6-{3-[2-(2-oxo-imidazolidin-1-yl)-ethylamino]-propyl}-pyrimidine-2-carbonitrile;
4-[3-(3-dimethylamino-propylamino)-propyl]-6-(3,4-dimethylphenyl)-pyrimidine-2-carbonitrile;
4-(3,4-dimethylphenyl)-6-{3-[2-(1-methyl-pyrrolidin-2-yl)-ethylamino]-propyl}-pyrimidine-2-carbonitrile;
4-(3-cyclopropylamino-propyl)-6-(3-trifluoromethylphenyl)-pyrimidine-2-carbonitrile
4-[3-(1-(s)-methyl-2-methoxyethylamino)-propyl]-6-(3-trifluoromethylphenyl)-pyrimidine-2-carbonitrile;
4-[3-(1-(S)-carbamoyl-ethylamino)-propyl]-6-(3-trifluoromethylphenyl)-pyrimidine-2-carbonitrile.
4-[3-(1-(R)-carbamoyl-ethylamino)-propyl]-6-(3-trifluoromethylphenyl)-pyrimidine-2-carbonitrile;
4-[3-(1-ethyl-1-methylpropylamino)-propyl]-6-(3-trifluoromethylphenyl)-pyrimidine-2-carbonitrile;
4-[3-(1-methyl-cyclopropylamino)-propyl]-6-(3-trifluoromethylphenyl)-pyrimidine-2-carbonitrile;
4-[3-(2-hydroxy-ethylamino)-propyl]-6-(3-trifluoromethylphenyl)-pyrimidine-2-carbonitrile;
4-[3-(1-carbamoyl-1-methyl-ethylamino)-propyl]-6-(3-trifluoromethylphenyl)-pyrimidine-2-carbonitrile;
4-[3-(2-oxo-pyrrolidin-3-(S)-ylamino)-propyl]-6-(3-trifluoromethylphenyl)-pyrimidine-2-carbonitrile; or a pharmaceutically acceptable salt thereof.

The invention provides in a further aspect pharmaceutical compositions comprising a 4-phenyl-pyrimidine-2-carbonitrile derivative having general formula I, or a pharmaceutically acceptable salt thereof, in admixture with pharmaceutically acceptable auxiliaries.

The 4-phenyl-pyrimidine-2-carbonitrile derivatives of general Formula I may be prepared by, as depicted in Scheme 1, by condensation of an acetophenone derivative having formula (II), wherein R has the meaning as previously defined, with an ester of formula R'—OC(O)R$_2$, wherein R' represents a (C$_{1-6}$)alkyl group and R$_2$ is as previously defined, to form a 1,3-dione derivative of formula (III). Optionally, the group R$_1$ can be introduced by alkylation of the 1,3-dione derivative in the presence of a base, e.g. potassium carbonate, and a suitable solvent, e.g. THF or acetone with heating, to provide a 2-alkyl-1,3-dione derivative having formula (IV). Cyclisation of the 1,3-dione (IV) with urea in the presence of an acid, e.g. concentrated aqueous hydrochloride in a suitable solvent, e.g. ethanol with heating, produces the 2-hydroxy-4-phenyl-pyrimidine derivative of formula (V). Treatment of a compound of formula (V) with POCl$_3$ under heat provides the 2-chloro-4-phenyl-pyrimidine derivative of formula (VI), which upon cyanation with cuprous cyanide in solvent, e.g. dimethylformamide or N-methylpyrrolidinone and with the help of microwave heating provides a 4-phenyl-pyrimidine-2-carbonitrile derivative of general Formula I. The cyanation step can also be performed with zinc cyanide as reagent with transition metal catalyst, e.g. tetrakistriphenylphosphine palladium in a suitable solvent, e.g. dimethylformamide, dimethoxyethane or N-methylpyrrolidinone.

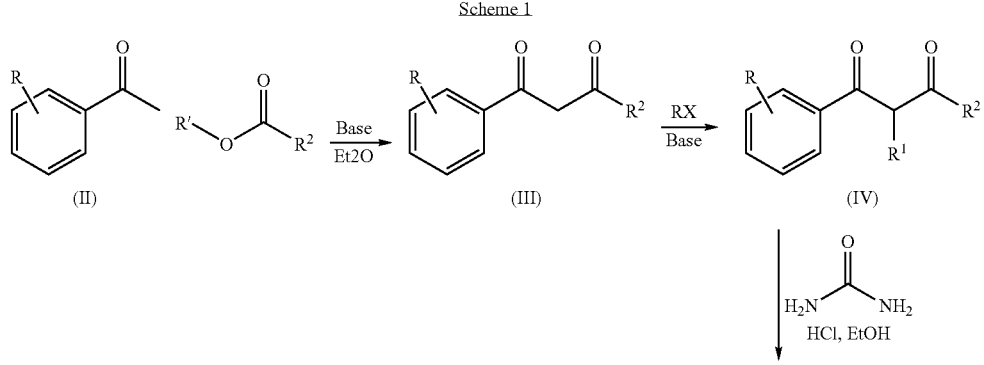

Scheme 1

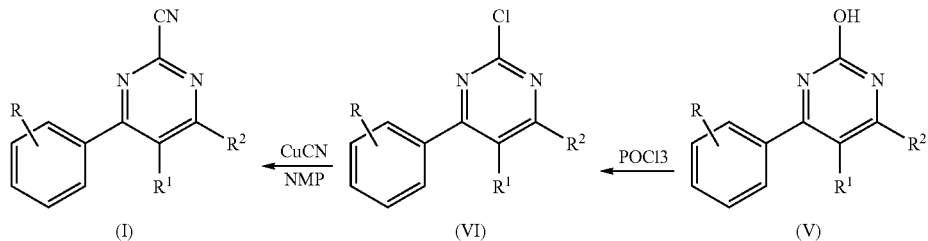

In an alternative method, as depicted in Scheme 2, a 1,3-dione derivative of formula (IV) is treated with S-methyl isothiourinium iodide in a suitable solvent, e.g. isopropanol, and a suitable base, e.g. triethyl amine, to give a 2-methylsulfanyl-4-phenyl-pyrimidine derivative of formula (VII). Oxidation of a derivative of formula VII with potassium monopersulfate (Oxone) or m-chloroperbenzoic acid (MCPBA) in a suitable solvent, e.g. methanol, water, chloroform or a mixture thereof, provides a 2-methanesulphonyl-4-phenyl-pyrimidine derivative of formula (VIII), which upon treatment with sodium cyanide in a suitable solvent, e.g. dimethylsulfoxide yields a 4-phenyl-pyrimidine-2-carbonitrile derivatives of general Formula I.

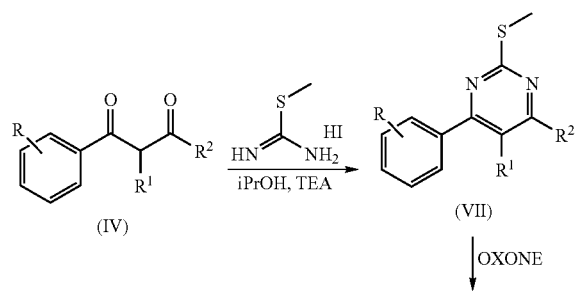

Scheme 2

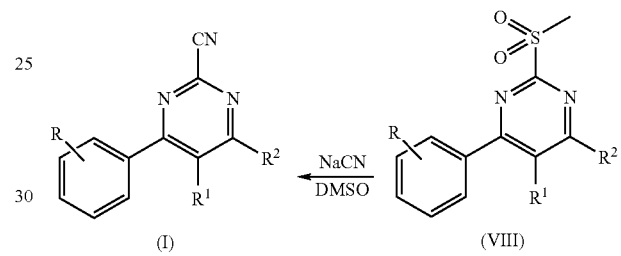

In another method, as depicted in Scheme 3, a β-keto-ester derivative of formula (IX), wherein $R_2$ is as previously defined, is condensed with thiourea in the presence of sodium methoxide to give a 2-mercapto-4-hydroxy-pyrimidine derivative of formula (X), which upon S-Methylation with iodomethane in the presence of a base, e.g. potassium hydroxide, provides a 2-methylsulfanyl-4-hydroxy-pyrimidine derivative of formula (XI). Treatment of a compound of formula XI with $POCl_3$ gives a 2-methylsulfanyl-4-chloropyrimidine derivative of formula (XII), oxidation with MCPBA of which provides a 2-methanesulphonyl-4-chloropyrimidine derivative of formula Scheme 3

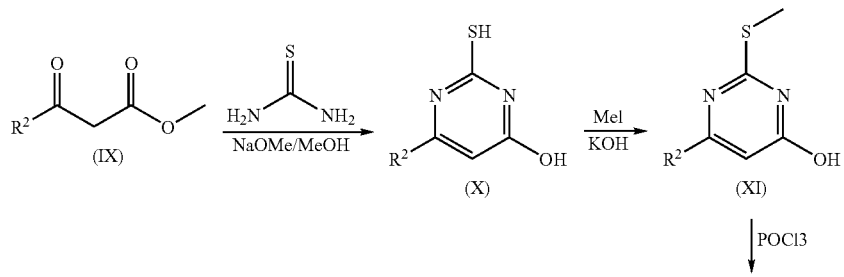

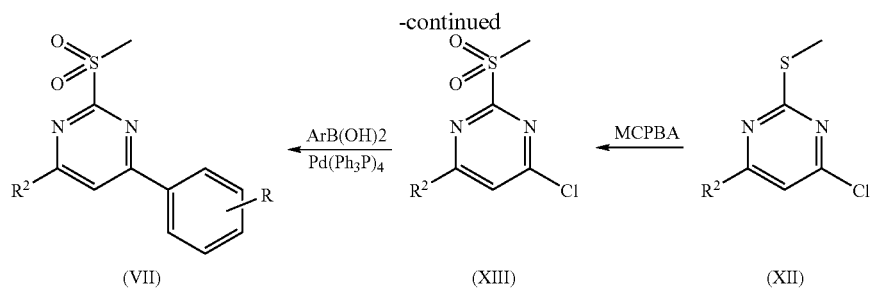

Coupling of XIII with phenyl boronic acids using transition metal catalyst, gives 2-methanesulfonyl-4-phenyl-pyrimidine derivatives of formula (VII), which can subsequently be converted to a 4-phenyl-pyrimidine-2-carbonitrile derivatives of general Formula I by treatment with sodium cyanide in a suitable solvent, e.g. dimethylsulfoxide.

In an alternative method, depicted in scheme 4, for the introduction of a phenyl group at the 4-position of the pyrimidine moiety, a compound having the formula XIII (see scheme 3) can be reacted with hexamethylbisstannane to give a 2-methanesulphonyl-4-trimethylstannyl-pyrimidine derivative of formula (XIV), which upon reaction with sodium cyanide in dimethylsulfoxide produces a 2-cyano-4-trimethylstannyl-pyrimidine derivative of formula (XV). Stille coupling of a compound of formula XV with aryl halides using a transition metal catalyst, as described in the general literature, provides a 4-phenyl-pyrimidine-2-carbonitrile derivative of general Formula I.

Scheme 4

The 4-phenyl-pyrimidine-2-carbonitrile derivatives of general Formula I, wherein $R_2$ represents a $(C_{2-6})$alkyl group substituted with $NR_3R_4$, can advantageously be prepared starting from the corresponding alcohol derivative as depicted in scheme 5 for compounds of the invention in which $R_2$ represent a 3-OH-propyl substituent. Oxidation of the pertinent alcohol derivative of formula (I) with Dess-Martin periodinane, or using an alternative oxidation procedure, provides the corresponding aldehyde derivative according to formula (XVI), which is subsequently condensed with an amine of formula $HNR_3R_4$ under reductive amination conditions to produce said 4-phenyl-pyrimidine-2-carbonitrile derivatives of the invention.

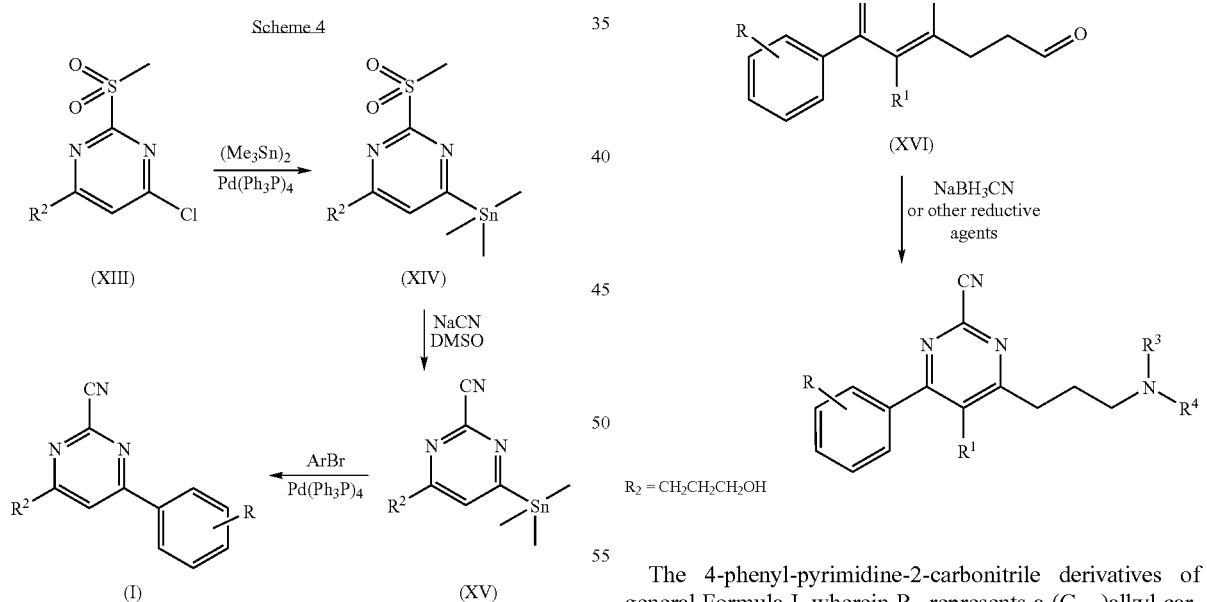

Scheme 5

The 4-phenyl-pyrimidine-2-carbonitrile derivatives of general Formula I, wherein $R_2$ represents a $(C_{2-6})$alkyl carboxylic acid or carboxyamides, can be advantageously prepared starting from the corresponding alcohol derivative as depicted in scheme 6 for compounds of the invention in which $R_2$ represent a 3-OH-propyl substituent. Oxidation of the pertinent alcohol derivative of formula (I) with sodium chlorite and sodium hypochloride in the presence of TEMPO as catalyst gives corresponding acid (XVIII). Coupling of this acid with primary or secondary amines with various coupling reagents, e.g. EDCI, PyBOP, HBTU et al provided the corresponding carboxyamide (XIX) as product.

Scheme 6

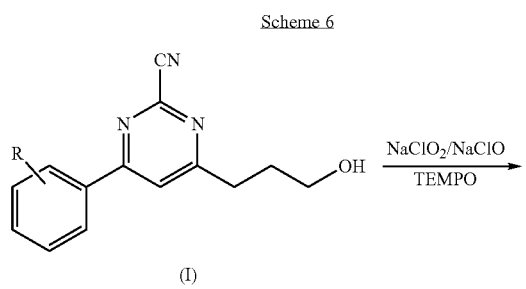

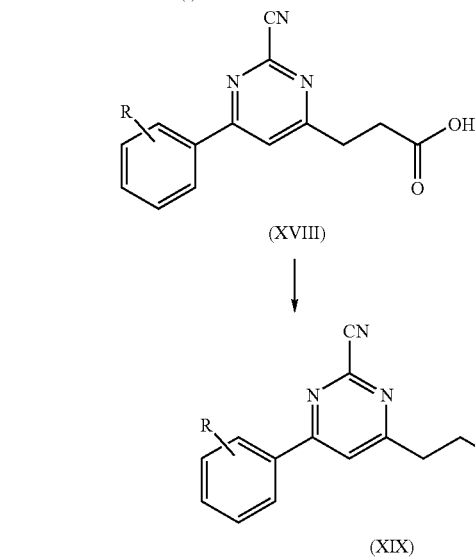

$R_2 = CH_2CH_2CH_2OH$

In another method as depicted in scheme 7, for the introduction of a phenyl group at the 4-position of the pyrimidine moiety, a compound having the formula XV (see scheme 4) was treated with iodine to give 2-cyano-4-iodo-pyrimidine derivative of formula (XX). Subsequently, a Stille or Suzuki or Negishi type of coupling of a compound of formula XX with aryl boronic acids or other aryl metallics of interest using a transition metal catalyst, as described in the general literature, provides a 4-phenyl-pyrimidine-2-carbonitrile derivatives of general Formula I.

Scheme 7

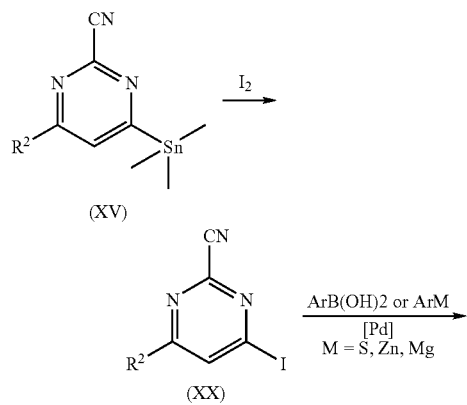

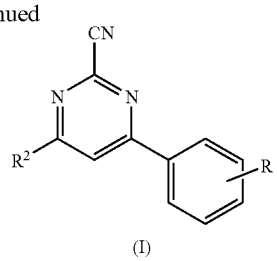

In another method as depicted in scheme 8, for the introduction of $R_2$ and a phenyl group at the 6- and 4-position, respectively, of the pyrimidine moiety, coupling of compound XXI with aryl halides with transition metal as catalyst followed by deprotection of the benzyl group will provide compound of generic formula I where $R_2$ is 3-hydroxypropyl which can be further derivatised according to scheme 5 to produce compounds with various $R_2$ and phenyl at 6- and 4-positions of pyrimidine ring.

Scheme 8

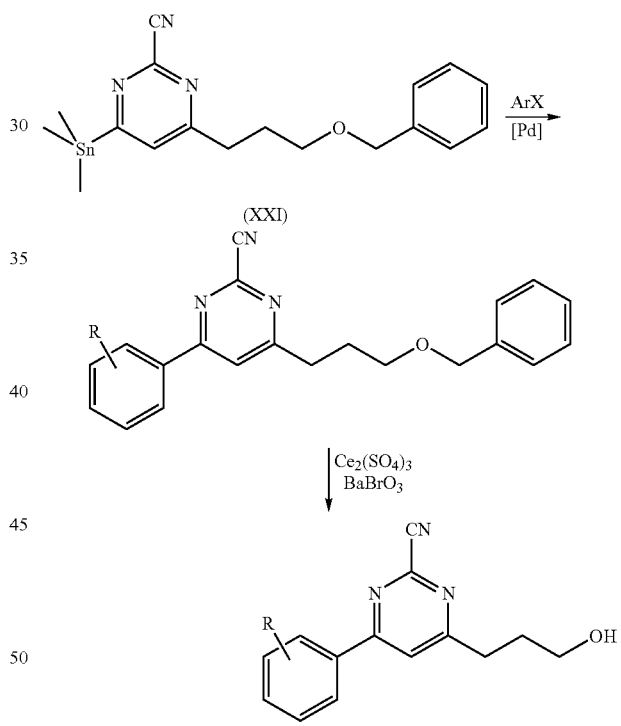

Compound XXI can be synthesised according scheme 3 and scheme 4 with the β-ketone ester with $R_2$ as 4-benzoxypropyl (XXIV) which can be synthesised as depicted in scheme 9. Reaction of 4-benzoxybutyric acid with Meldrum's acid in presence of isopropenyl chloroformate with DMAP as base provided acylated Meldrum acid derivative, which was then converted to XXIV by acid assisted ethanolysis. Alternatively, compound XXIV can also be synthesised from ethyl or methyl acetoacetate (XXV) via well documented double anion chemistry with 3-benzoxyethyl bromide (XXVI) as alkylating agent In the preparation of a 4-phenyl-pyrimidine-2-carbonitrile derivatives of general Formula I in which the $R_2$ group contains a basic amine nitrogen atom (either in the form of $NR_3R_4$ or $NR_5$), such a nitrogen is to be temporarily protected, such as for example by the acid labile t-butyloxycarbonyl (Boc) group protecting group. Other suitable protecting groups for functional groups which are to be temporarily protected during syntheses, are known in the art, for example from Wuts, P. G. M. and Greene, T. W.: *Protective Groups in Organic Synthesis*, Third Edition, Wiley, New York, 1999.

The compounds of the invention were found to be inhibitors of human Cathepsin K and Cathepsin S can therefore in a further aspect of the invention be used in therapy, and especially for the preparation of a medicament for the treatment of osteoporosis, atherosclerosis and related Cathepsin K and Cathepsin S dependent disorders, e.g. inflammation and immune disorders such as rheumatoid arthritis, chronic pain such as neuropathic pain, and further disorders related to

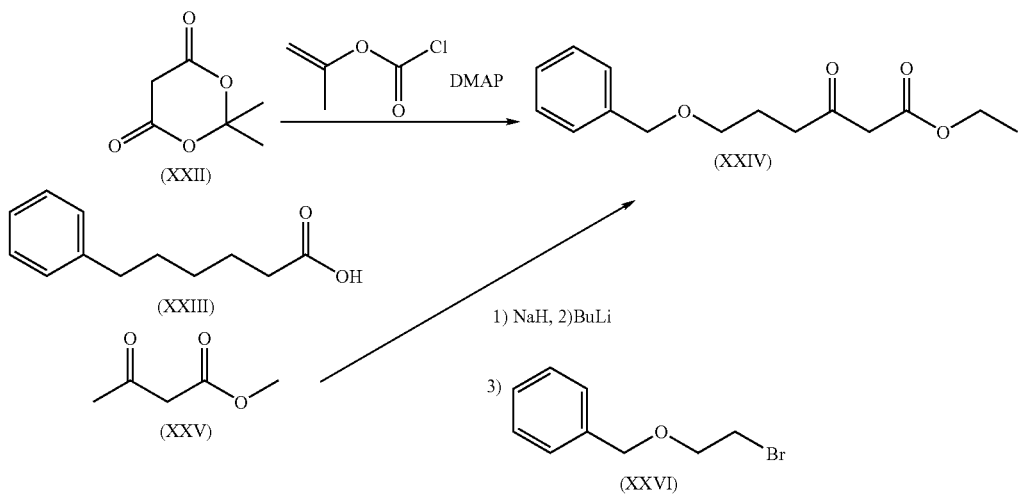

Scheme 9

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid, and ascorbic acid.

Compounds of the invention may exist in solvated as well as in unsolvated forms, including hydrated forms. In general, the solvated forms are equivalent to unsolvated forms and are intended to be encompassed within the scope of the present invention. Compounds of the present invention may exist as amorphous forms, but also multiple crystalline forms may be possible. In general, all physical forms are equivalent for the uses contemplated by the present invention and are intended to be within the scope of this invention.

The 4-phenyl-pyrimidine-2-carbonitrile derivatives of the invention and their salts may contain a centre of chirality in one or more of the side chains R, $R_1$-$R_{10}$, and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

abnormal bone resorption such as Paget's disease, osteoarthritis, osteolytic bone cancer and metastatic bone disease.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray. For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

Methods

General Chemical Procedures. All reagents were either purchased from common commercial sources or synthesised according to literature procedures using commercial sources. Proton NMR ($^1$H NMR) were obtained on a Bruker DPX 400 spectrometer and are referenced to internal TMS. Mass spectra were recorded on a Shimadzu LC-8A (HPLC) PE Sciex API 150EX LCMS. Analytical reversed-phase LCMS analysis was carried out on LUNA C18 column (5μ; 30×4.6 mm) under gradient conditions (90% water/0.1% formic acid to 90% acetonitrile/0.1% formic acid) at a flow rate of 4 ml/min.

Abbreviations

Dimethylformamide (DMF), N-methylpyrrolidinone (NMP), dichloromethane (DCM), dimethylsufoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), 1-(3-dimethylaminopropyl)-3-ethyl carbodiimide HCl (EDCI), 1-hydroxybenzotriazole (HOBt), 2,2,6,6-tetramethyl-1-piperidihyloxy (TEMPO).

EXAMPLE 1

4-Propyl-6-(3-trifluoromethylphenyl)-pyrimidine-2-carbonitrile

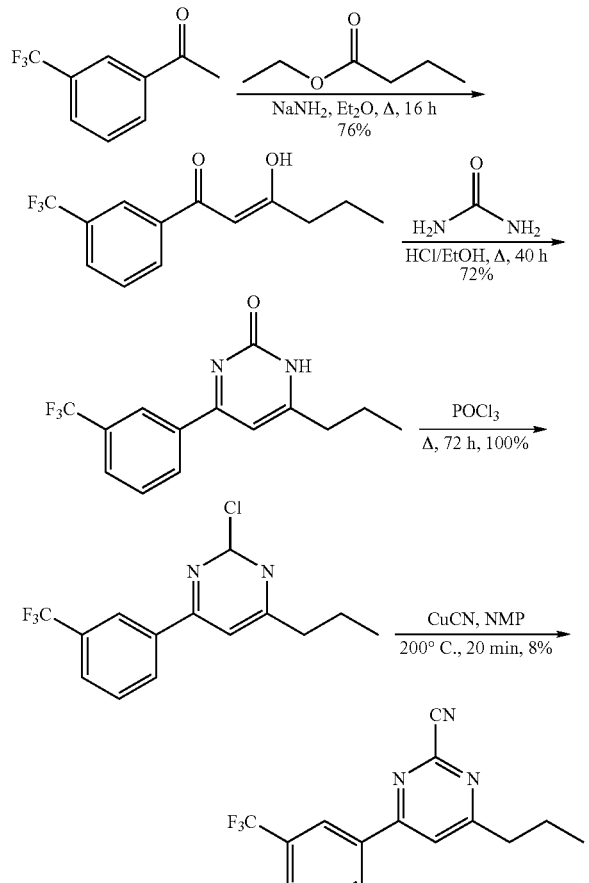

A: 3-hydroxy-1-(3-trifluoromethylphenyl)-hex-2-en-1-one

To a stirred suspension of sodium amide (0.78 g) in ether (40 mL), under nitrogen, was added 3-trifluoroacetophenone (1.52 mL). The mixture was stirred for 5 min, then ethyl butyrate (1.32 mL) was added slowly. The resulting mixture was heated at reflux overnight, cooled to room temperature, and quenched with water (20 mL). The ether layer was removed, and the aqueous acidified with HCl (5M) followed by extraction with ether (3×20 mL). The organic layers were combined, washed with water (20 mL), dried over sodium sulphate, and evaporated at reduced pressure to give the crude product as an oil. Flash silica chromatography afforded 3-hydroxy-1-(3-trifluoromethylphenyl)-hex-2-en-1-one as an oil (0.74 g).

$^1$H NMR (CDCl$_3$): δ 8.12 (s, 1H), 8.06 (d, 1H), 7.77 (d, 1H), 7.59 (t, 1H), 6.19 (s, 1H), 3.88 (br s, 1H), 2.44 (t, 2H), 1.69-1.79 (m, 2H), 1.01 (t, 3H).

B: 6-propyl-4-(3-trifluoromethylphenyl)-1H-pyrimidin-2-one

A stirred mixture of 3-hydroxy-1-(3-trifluoromethylphenyl)-hex-2-en-1-one (259 mg), urea (90 mg), HCl (0.15 mL, 5M) and ethanol (5 mL) was heated at reflux for 16 h. Further urea (60 mg) and HCl (0.15 mL, 5M) were added and heating continued at reflux for 24 h. The mixture was allowed to cool and the solvent was evaporated at reduced pressure. The residue was dissolved in a mixture of ethyl acetate (20 mL) and water (20 mL), the organic layer was separated and further washed with a solution of saturated sodium carbonate (20 mL) followed by water (20 mL). The ethyl acetate extract was then dried over sodium sulphate and evaporated at reduced pressure to afford 6-propyl-4-(3-trifluoromethylphenyl)-1H-pyrimidin-2-one as a brown solid (204 mg). MS m/z 283.0 (M+1), 100%.

C: 2-chloro-4-propyl-6-(3-trifluoromethylphenyl)-pyrimidine

A mixture of 6-propyl-4-(3-trifluoromethylphenyl)-1H-pyrimidin-2-one (204 mg) and phosphorus oxychloride (3 mL) was stirred and heated at reflux for 72 h, then allowed to cool and poured onto a mixture of ice/ether (20 mL). The ether layer was separated, washed with saturated sodium carbonate solution (20 mL), dried over sodium sulphate, and evaporated at reduced pressure to afford 2-chloro-4-propyl-6-(3-trifluoromethylphenyl)-pyrimidine as a dark brown oil (239 mg).

MS m/z 301.3 (M+1), 100%.

D: 4-propyl-6-(3-trifluoromethylphenyl)-pyrimidine-2-carbonitrile

To a solution of 2-chloro-4-propyl-6-(3-trifluoromethylphenyl)-pyrimidine (50 mg) in 1-methyl-2-pyrrolidinone (2 mL), was added copper(I) cyanide (60 mg). The suspension was heated in the microwave at 200° C. for 20 min, than poured into a mixture of ethyl acetate (10 mL) and ammonia solution (5 mL). The organic layer was separated, washed with water (10 mL), dried over sodium sulphate and evaporated at reduced pressure. Preparative HPLC afforded the title compound 4-propyl-6-(3-trifluoromethylphenyl)-pyrimidine-2-carbonitrile as a brown gum (4.1 mg).

$^1$H NMR (CDCl$_3$): δ 8.27-8.37 (m, 2H), 7.82 (d, 1H), 7.34 (s, 1H), 7.68 (t, 1H), 2.88 (t, 2H), 1.78-1.91 (m, 2H), 1.03 (t, 3H). MS m/z 292.0 (M+1), 100%.

EXAMPLE 2

5-Methyl-4-propyl-6-(3-trifluoromethylphenyl)-pyrimidine-2-carbonitrile

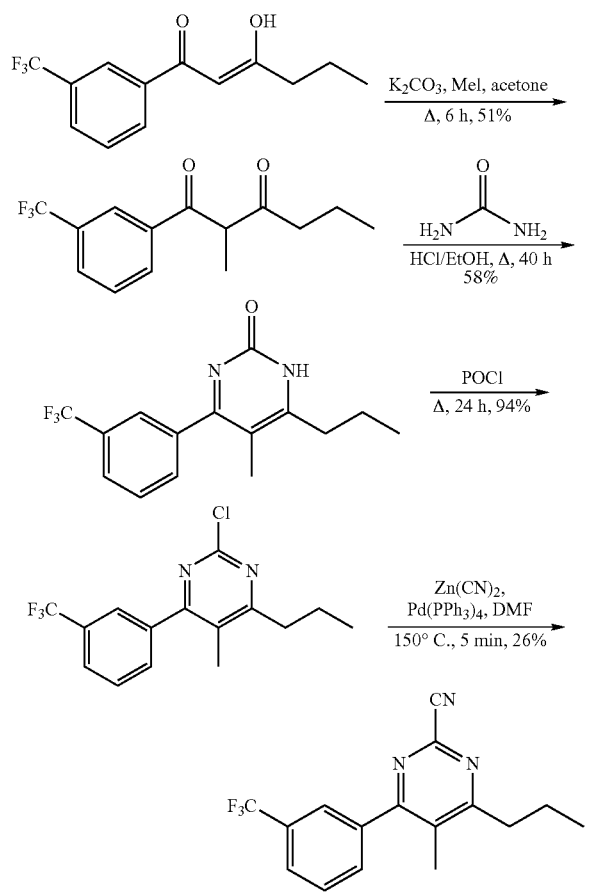

A: 2-methyl-1-(3-trifluoromethylphenyl)-hexane-1,3-dione

To a stirred suspension of potassium carbonate (596 mg) in acetone (7 mL), was added 3-hydroxy-1-(3-trifluoromethylphenyl)-hex-2-en-1-one (190 mg) followed by iodomethane (0.45 mL). The mixture was heated at reflux for 6 h, cooled to room temperature, and the solvent evaporated at reduced pressure. The resulting oil was dissolved in ethyl acetate (20 mL), washed with water (3×20 mL), dried over sodium sulphate and evaporated at reduced pressure to give the crude product as an oil. Flash silica chromatography afforded 2-methyl-1-(3-trifluoromethylphenyl)-hexane-1,3-dione as an oil (102 mg).

$^1$H NMR (CDCl$_3$): δ 8.14 (s, 1H), 8.06 (d, 1H), 7.77 (d, 1H), 7.56 (t, 1H), 4.41 (q, 1H), 2.29-2.48 (m, 2H), 1.46-1.55 (m, 2H), 1.40 (d, 3H), 0.78 (t, 3H).

B: 5-methyl-6-propyl-4-(3-trifluoromethylphenyl)-1H-pyrimidin-2-one

A stirred mixture of 2-methyl-1-(3-trifluoromethylphenyl)-hexane-1,3-dione (102 mg), urea (45 mg), HCl (0.10 mL, 5M) and ethanol (4 mL) was heated at reflux for 16 h. Further urea (30 mg) and HCl (0.10 mL, 5M) were added and heating continued at reflux for 24 h. The mixture was allowed to cool and the solvent was evaporated at reduced pressure. The residue was dissolved in a mixture of ethyl acetate (10 mL) and water (10 mL), the organic layer was separated and further washed with a solution of saturated sodium carbonate (10 mL) followed by water (10 mL). The ethyl acetate extract was then dried over sodium sulphate and evaporated at reduced pressure to afford 5-methyl-6-propyl-4-(3-trifluoromethylphenyl)-1H-pyrimidin-2-one as a yellow oil (64 mg).

MS m/z 297.4 (M+1), 100%.

C: 2-chloro-5-methyl-4-propyl-6-(3-trifluoromethylphenyl)-pyrimidine

A mixture of 5-methyl-6-propyl-4-(3-trifluoromethylphenyl)-1H-pyrimidin-2-one (64 mg) and phosphorus oxychloride (3 mL) was stirred and heated at reflux for 24 h, then allowed to cool and poured onto a mixture of ice/ether (20 mL). The ether layer was separated, washed with saturated sodium carbonate solution (10 mL) and water (10 mL), dried over sodium sulphate, and evaporated at reduced pressure to afford 2-chloro-5-methyl-4-propyl-6-(3-trifluoromethylphenyl)-pyrimidine as an oil (64 mg).

MS m/z 315.0 (M+1), 100%.

D: 5-methyl-4-propyl-6-(3-trifluoromethylphenyl)-pyrimidine-2-carbonitrile

To a solution of 2-chloro-5-methyl-4-propyl-6-(3-trifluoromethylphenyl)-pyrimidine (50 mg) in dimethylformamide (1 mL), was added zinc(II) cyanide (16 mg) and tetrakis(triphenylphosphine)-palladium(0) (16 mg). The suspension was heated in the microwave at 150° C. for 5 min, then poured into ethyl acetate (50 mL) and washed with water (2×10 mL). The organic layer was separated, dried over sodium sulphate and evaporated at reduced pressure. Preparative-HPLC afforded 5-methyl-4-propyl-6-(3-trifluoromethylphenyl)-pyrimidine-2-carbonitrile as a yellow gum (11 mg). $^1$H NMR (CDCl$_3$): δ 7.63-7.81 (m, 4H), 2.87 (t, 2H), 2.39 (s, 3H), 1.80-1.90 (m, 2H), 1.07 (t, 3H). MS m/z 306.4 (M+1), 100%.

EXAMPLE 3

4-(3-hydroxy-1-propyl)-6-(3-trifluoromethylphenyl)-pyrimidine-2-carbonitrile

A: 1,3-dioxo-6-hydroxy-1-(3'-trifluorophenyl)-hexane

To a stirred suspension of sodium hydride (60% in parafin oil, 20 g) in diethyl ether (1 L) at 0° C. was added ethanol (1 ml). To above mixture was then added gamma-butyrolactone (18 g), followed by dropwise addition of diethyl ether solution (100 ml) 3'-trifluoromethylacetophenone (38 g) in 30 minutes. The mixture was allowed to stir at room temperature for 72 hours. Ethanol (20 ml) was then added to destroy excess sodium hydride, followed by addition of aqueous solution of ammonium chloride (20 g in 300 ml water). Organic layer separated and washed with diluted hydrochloric acid (0.1N, 500 ml), then with water (2×200 ml). Ether layer was then dried over sodium sulphate, solvent removed under reduced pressure. The residue was columned on silica gel using petrol and ethyl acetate (1:1) as eluant to give 1,3-dioxo-6-hydroxy-1-(3'-trifluorophenyl)-hexane (32 g). $^1$H NMR (CDCl₃): δ 8.1 (s, 1H), 8.04 (d, 1H), 7.76 (d, 1H), 7.55 (dd, 1H), 6.2 (s, 1H), 3.74 (t, 2H), 2.61 (t, 2H), 1.97 (m, 2H). MS m/z 275 (M+1), 100%.

B: 2-methylsulfanyl-4-(3-hydroxypropyl)-6-(3-trifluoromethylphenyl)pyrimidine To the solution of 1,3-dioxo-6-hydroxy-1-(3'-trifluorophenyl)-hexane (32 g) in isopropanol (30 ml) was added S-methyl isothiouranium iodide salt (34 g). The mixture was heated at 110° C. for 4 hours. After cooling to room temperature, triethylamine (45 ml) and methanol (50 ml) were added, and the mixture was heated to reflux with an oil bath at 85° C. for 6 hours. After removal of solvent and triethyl amine at reduced pressure, the residue was taken into ethyl acetate (500 ml) and water (500 ml). Organic layer was then separated, then washed with diluted hydrochloric acid (0.1N, 500 ml), followed with water (2×300 ml). Organic layer was then dried, solvent removed under reduced pressure. The residue was columned on silica gel using petrol and ethyl acetate (1:1) as eluant to give 2-methylsulfanyl-4-(3-hydroxypropyl)-6-(3-trifluoromethylphenyl)pyrimidine (18 g). ¹H NMR (CDCl₃): δ 8.3 (s, 1H), 8.25 (d, 1H), 7.76 (d, 1H), 7.58 (dd, 1H), 7.28 (s, 1H), 3.74 (t, 2H), 2.92 (t, 2H), 2.65 (s, 3H), 2.03 (m, 2H). MS m/z 329 (M+1), 100%.

C: 2-methanesulphonyl-4-(3-hydroxypropyl)-6-(3-trifluoromethylphenyl)pyrimidine To the solution of 2-methylsulfanyl-4-(3-hydroxypropyl)-6-(3-trifluoromethyl-phenyl)pyrimidine (7.8 g) in a mixed solvent of methanol and water (200 ml, 10:1) was added OXONE (34 g). The mixture was stirred at room temperature for 3 hours, then, diluted with ethyl acetate (500 ml). The mixture was washed with water (3×500 ml). Organic layer dried over sodium sulphate, solvent removed under reduced pressure to give 2-methanesulphonyl-4-(3-hydroxypropyl)-6-(3-trifluoromethylphenyl)-pyrimidine (8.9 g) as crude product which was used for next step without further purification. ¹H NMR (CDCl₃): δ 8.3-8.4 (m, 2H), 7.8-7.87 (m, 2H), 7.68 (dd, 1H), 3.77 (t, 2H), 3.43 (s, 3H), 3.10 (t, 2H), 2.10 (m, 2H).

D: 4-(3-Hydroxy-propyl)-6-(3-trifluoromethylphenyl)-pyrimidine-2-carbonitrile To a stirred solution of 2-methylsulphonyl-4-(3-hydroxypropyl)-6-(3-trifluoro-methylphenyl)pyrimidine (200 mg) in dimethylsulfoxide (5 mL), was added sodium cyanide (27 mg). The mixture was stirred at room temperature for 45 min, then poured into ethyl acetate (50 mL) and washed with water (2×50 mL). The organic layer was dried over sodium sulphate, evaporated at reduced pressure, and purified using preparative-H PLC. 4-(3-Hydroxy-propyl)-6-(3-trifluoromethylphenyl)-pyrimidine-2-carbonitrile was isolated as a gum (78 mg).
¹H NMR (CDCl₃): δ 8.35 (s, 1H), 8.32 (d, 1H), 7.83 (d, 1H), 7.80 (s, 1H), 7.69 (t, 1H), 3.77 (t, 2H), 3.05 (t, 2H), 2.07-2.13 (m, 2H). MS m/z 308.3 (M+1), 100%.

EXAMPLE 4a

4-(3-Piperidin-1-yl-propyl)-6-(3-trifluoromethylphenyl)-pyrimidine-2-carbonitrile

A: 4-(3-oxo-propyl)-6-(3-trifluoromethylphenyl)-pyrimidine-2-carbonitrile

Dess-Martin periodinane (104 mg) was added to a solution of 4-(3-hydroxy-propyl)-6-(3-trifluoromethylphenyl)-pyrimidine-2-carbonitrile (50 mg) in dichloro-methane (5 mL), and the resulting suspension stirred at room temperature for 45 min. The mixture was then washed with water (3×10 mL), dried over sodium sulphate, and evaporated at reduced pressure to afford 4-(3-oxo-propyl)-6-(3-trifluoromethyl-phenyl)-pyrimidine-2-carbonitrile as a brown solid (70 mg). MS m/z 306.1 (M+1), 100%.

B: 4-(3-piperidin-1-yl-propyl)-6-(3-trifluoromethylphenyl)-pyrimidine-2-carbonitrile To a suspension of macroporous cyanoborohydride (102 mg, 2.35 mmol/g) in acetonitrile (0.5 mL), was added piperidine (19 µL), acetic acid (0.1 mL), and a solution of 4-(3-oxo-propyl)-6-(3-trifluoromethylphenyl)-pyrimidine-2-carbonitrile (49 mg) in acetonitrile (0.5 mL). The mixture was heated in the microwave at 150° C. for 10 min, filtered in a fritted tube using a Vacmaster multi-filtration apparatus, and purified by preparative-HPLC. 4-(3-Piperidin-1-yl-propyl)-6-(3-trifluoromethylphenyl)-pyrimidine-2-carbonitrile was isolated as a clear gum (12 mg).
¹H NMR (CDCl₃): δ 8.34 (s, 1H), 8.32 (d, 1H), 7.82 (d, 1H), 7.79 (s, 1H), 7.68 (t, 1H), is 2.93 (t, 2H), 2.32-2.44 (m, 5H), 1.97-2.05 (m, 2H), 1.49-1.60 (m, 4H), 1.37-1.45 (m, 2H), 1.23-1.38 (m, 1H). MS m/z 375.3 (M+1), 85%.

The procedure described above was further applied, using the appropriate amine derivatives, to prepare the following compounds:

4b: 4-(3-Morpholin-4-yl-propyl)-6-(3-trifluoromethylphenyl)-pyrimidine-2-carbonitrile ¹H NMR (CDCl₃): δ 8.28-8.34 (m, 2H), 7.82 (d, 1H), 7.78 (s, 1H), 7.69 (t, 1H), 3.68 (t, 4H), 2.96 (t, 2H), 2.38-2.48 (m, 6H), 1.98-2.07 (m, 2H). MS m/z 377.4 (M+1), 100%.

4c: 4-[3-(4,4-Difluoro-piperidin-1-yl)-propyl]-6-(3-trifluoromethylphenyl)-pyrimidine-2-carbonitrile ¹H NMR (CDCl₃): δ 8.31-8.33 (m, 2H), 7.83 (d, 1H), 7.76 (s, 1H), 7.69 (t, 1H), 2.95 (t, 2H), 2.55 (br t, 4H), 2.48 (t, 2H), 1.92-2.05 (m, 6H). MS m/z 411.3 (M+1), 100%.

4d: 4-[3-(4-Methyl-piperazin-1-yl)-propyl]-6-(3-trifluoromethylphenyl)-pyrimidine-2-carbonitrile ¹H NMR (CDCl₃): δ 8.31-8.33 (m, 2H), 7.82 (d, 1H), 7.78 (s, 1H), 7.69 (t, 1H), 2.94 (t, 2H), 2.30-2.60 (br m, 10H), 2.26 (s, 3H), 1.98-2.05 (m, 2H). MS m/z 390.1 (M+1), 100%.

4e: 4-(3-Cyclohexylamino-propyl)-6-(3-trifluoromethylphenyl)-pyrimidine-2-carbonitrile ¹H NMR (CDCl₃): δ 8.31-8.34 (m, 2H), 7.82 (d, 1H), 7.78 (s, 1H), 7.68 (t, 1H), 2.97 (t, 2H), 2.71 (t, 2H), 2.35-2.45 (m, 1H), 1.92-2.03 (m, 2H), 1.79-1.91 (m, 2H), 1.65-1.77 (m, 2H), 1.54-1.65 (m, 1H), 0.96-1.32 (m, 5H). MS m/z 389.3 (M+1), 100%.

4f: 4-(3-isopropylamino-propyl)-6-(3-trifluoromethylphenyl)-pyrimidine-2-carbonitrile ¹H NMR (CDCl₃): δ 8.31-8.35 (m, 2H), 7.82 (d, 1H), 7.78 (s, 1H), 7.68 (t, 1H), 2.98 (t, 2H), 2.80 (quin, 1H), 2.69 (t, 2H), 1.95-2.02 (m, 2H), 1.05 (d, 6H). MS m/z 349.5 (M+1), 83%.

4g: 4-[3-(Benzyl-methyl-amino)-propyl]-6-(3-trifluoromethylphenyl)-pyrimidine-2-carbonitrile $^1$H NMR (CDCl$_3$): δ 8.33 (s, 1H), 8.28 (d, 1H), 7.82 (d, 1H), 7.69 (s, 1H), 7.67 (t, 1H), 7.20-7.29 (m, 5H), 3.49 (s, 2H), 2.94 (t, 2H), 2.40-2.50 (br t, 2H), 2.23 (s, 3H), 1.97-2.08 (m, 2H). MS m/z 411.3 (M+1), 100%.

4h: 4-(3-Isobutylamino-propyl)-6-(3-trifluoromethylphenyl)-pyrimidine-2-carbonitrile $^1$H NMR (CDCl$_3$): δ 8.34 (s, 1H), 8.32 (d, 1H), 7.82 (d, 1H), 7.78 (s, 1H), 7.68 (t, 1H), 2.98 (t, 2H), 2.69 (t, 2H), 2.42 (d, 2H), 1.95-2.05 (m, 2H), 1.66-1.78 (m, 1H), 0.91 (d, 6H). MS m/z 363.3 (M+1), 98%.

4i: 4-{3-[(Pyridin-4-ylmethyl)-amino]-propyl}-6-(3-trifluoromethylphenyl)-pyrimidine-2-carbonitrile $^1$H NMR (CDCl$_3$): δ 8.54 (d, 2H), 8.34 (s, 1H), 8.30 (d, 1H), 7.83 (d, 1H), 7.75 (s, 1H), 7.68 (t, 1H), 7.24-7.27 (m, 2H), 3.82 (s, 2H), 3.00 (t, 2H), 2.73 (t, 2H), 2.00-2.09 (m, 2H). MS m/z 398.0 (M+1), 100%.

4j: 4-(3-Pyrrolidin-1-yl-propyl)-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.79 (s, 1H), 7.68 (t, 1H), 2.97 (t, 2H), 2.44-2.56 (m, 6H), 2.00-2.07 (m, 2H), 1.74-1.79 (m, 4H). MS m/z 361.1 (M+1), 100%.

4k: 4-(3-Azepan-1-yl-propyl)-6-(3-trifluoromethylphenyl)-pyrimidine-2-carbonitrile $^1$H NMR (CDCl$_3$): δ 8.34 (s, 1H), 8.32 (d, 1H), 7.82 (d, 1H), 7.78 (s, 1H), 7.68 (t, 1H), 2.94 (t, 2H), 2.58-2.61 (m, 4H), 2.53 (t, 2H), 1.94-2.01 (m, 2H), 1.54-1.67 (m, 8H). MS m/z 389:3 (M+1), 100%.

4l: 4-[3-(azacyclooct-1-yl)-propyl]-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.77 (s, 1H), 7.68 (t, 1H), 2.98 (t, 2H), 2.48-2.58 (m, 6H), 1.91-2.00 (m, 2H), 1.51-1.72 (m, 10H). MS m/z 403.5 (M+1), 100%.

4m: 4-(3-Cyclopentylamino-propyl)-6-(3-trifluoromethylphenyl)-Pyrimidine-2-carbonitrile $^1$H NMR (CDCl$_3$): δ 8.36 (s, 1H), 8.30 (d, 1H), 7.81-7.84 (m, 2H), 7.67 (t, 1H), 3.48 (br t, 1H), 3.08-3.20 (br m, 2H), 3.04 (t, 2H), 2.26-2.33 (m, 2H), 2.00-2.13 (m, 2H), 1.71-1.84 (m, 4H), 1.57-1.68 (m, 2H). MS m/z 375.3 (M+1), 100%.

4n: 4-(3-Cycloheptylamino-propyl)-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.79 (s, 1H), 7.68 (t, 1H), 2.97 (t, 2H), 2.67 (t, 2H), 2.58-2.64 (m, 1H), 1.95-2.02 (m, 2H), 1.24-1.84 (m, 12H). MS m/z 403.5 (M+1), 100%.

4o: 4-[3-(Cyclohexylmethyl-amino)-propyl]-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.78 (s, 1H), 7.68 (t, 1H), 2.97 (t, 2H), 2.68 (t, 2H), 2.43 (d, 2H), 1.96-2.04 (m, 2H), 0.85-1.77 (m, 11H). MS m/z 403.5 (M+1), 100%.

4p: 4-(3-tert-Butylamino-propyl)-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.79 (s, 1H), 7.68 (t, 1H), 2.99 (t, 2H), 2.66 (t, 2H), 1.94-2.01 (m, 2H), 1.11 (s, 9H). MS m/z 363.3 (M+1), 100%.

4q: 4-[3-(2,2-Dimethyl-propylamino)-propyl]-6-(3-trifluoromethylphenyl)-pyrimidine-2-carbonitrile $^1$H NMR (CDCl$_3$): δ 8.34 (s, 1H), 8.32 (d, 1H), 7.82 (d, 1H), 7.78 (s, 1H), 7.68 (t, 1H), 2.99 (t, 2H), 2.69 (t, 2H), 2.34 (s, 2H), 1.97-2.04 (m, 2H), 0.90 (s, 9H). MS m/z 377.5 (M+1), 100%.

4r: 4-[3-(1-Ethyl-propylamino)-propyl]-6-(3-trifluoromethylphenyl)-pyrimidine-2-carbonitrile $^1$H NMR (CDCl$_3$): δ 8.35 (s, 1H), 8.32 (d, 1H), 7.82 (d, 1H), 7.79 (s, 1H), 7.68 (t, 1H), 2.99 (t, 2H), 2.66 (t, 2H), 2.33-2.39 (quin, 1H), 1.95-2.02 (m, 2H), 1.35-1.47 (m, 4H), 0.88 (t, 6H). MS m/z 377.5 (M+1), 100%.

4s: 4-{3-[Methyl-(1-methyl-piperidin-4-yl)-amino]-propyl}-6-(3-trifluoromethylphenyl)-pyrimidine-2-carbonitrile $^1$H NMR (CDCl$_3$): δ 8.34 (s, 1H), 8.32 (d, 1H), 7.82 (d, 1H), 7.77 (s, 1H), 7.68 (t, 1H), 2.87-2.95 (m, 4H), 2.51 (t, 2H), 2.29-2.37 (m, 1H), 2.25 (s, 6H), 1.88-2.01 (m, 4H), 1.53-1.70 (m, 4H). MS m/z 418.3 (M+1), 58%.

4t: 4-[3-(2,2,2-Trifluoro-ethylamino)-propyl]-6-(3-trifluoromethylphenyl)-pyrimidine-2-carbonitrile $^1$H NMR (MeOD): δ 8.51 (s, 1H), 8.48 (d, 1H), 8.24 (s, 1H), 7.91 (d, 1H), 7.79 (t, 1H), 3.92 (q, 2H), 3.21 (t, 2H), 3.08 (t, 2H), 2.21-2.29 (m, 2H). MS m/z 389.1 (M+1), 58%.

4u: 4-[3-(4-Methyl-[1,4]diazepan-1-yl)-propyl]-6-(3-trifluoromethylphenyl)-pyrimidine-2-carbonitrile $^1$H NMR (CDCl$_3$): δ 8.32-8.34 (m, 2H), 7.82 (d, 1H), 7.79 (s, 1H), 7.69 (t, 1H), 2.94 (t, 2H), 2.68-2.71 (m, 4H), 2.53-2.62 (m, 6H), 2.34 (s, 3H), 1.94-2.02 (m, 2H), 1.76-1.82 (m, 2H). MS m/z 404.5 (M+1), 100%.

4v: 4-(3-[1,4]Oxazepan-4-yl-propyl)-6-(3-trifluoromethylphenyl)-pyrimidine-2-carbonitrile $^1$H NMR (CDCl$_3$): δ 8.39 (s, 1H), 8.31 (d, 1H), 7.86 (s, 1H), 7.83 (d, 1H), 7.68 (t, 1H), 3.97 (t, 2H), 3.87 (t, 2H), 2.07-3.77 (m, 12H). MS m/z 391.1 (M+1), 100%.

4w: 4-(3-Phenylamino-propyl)-6-(3-trifluoromethylphenyl)-pyrimidine-2-carbonitrile $^1$H NMR (CDCl$_3$): δ 8.31 (s, 1H), 8.26 (d, 1H), 7.81 (d, 1H), 7.72 (s, 1H), 7.66 (t, 1H), 7.16 (t, 2H), 6.70 (t, 1H), 6.60 (d, 2H), 3.72 (br s, 1H), 3.27 (t, 2H), 3.03 (t, 2H), 2.15-2.19 (m, 2H). MS m/z 383.1 (M+1), 58%.

4x: 4-[3-(4-Pyridin-2-yl-benzylamino)-propyl]-6-(3-trifluoromethylphenyl)-pyrimidine-2-carbonitrile $^1$H NMR (CDCl$_3$): δ 8.68 (d, 1H), 8.34 (s, 1H), 8.27 (d, 1H), 7.94 (d, 2H), 7.63-7.81 (m, 5H), 7.41 (d, 2H), 7.21-7.23

(m, 1H), 3.86 (s, 2H), 2.99 (t, 2H), 2.74 (t, 2H), 2.00-2.07 (m, 2H). MS m/z 474.1 (M+1), 42%.

4y: 4-[3-(4-Phenyl-piperazin-1-yl)-propyl]-6-(3-trifluoromethylphenyl)-pyrimidine-2-carbonitrile $^1$H NMR (MeOD): δ 8.51 (s, 1H), 8.47 (d, 1H), 8.24 (s, 1H), 7.90 (d, 1H), 7.77 (t, 1H), 7.21 (t, 2H), 6.93 (d, 2H), 6.83 (t, 1H), 3.11-3.15 (m, 4H), 2.99 (t, 2H), 2.63-2.68 (m, 4H), 2.53 (t, 2H), 2.05-2.13 (m, 2H). MS m/z 452.1 (M+1), 100%.

4z: 4-[3-(4-Benzyl-piperazin-1-yl)-propyl]-6-(3-trifluoromethylphenyl)-pyrimidine-2-carbonitrile $^1$H NMR (CDCl$_3$): δ 8.31-8.34 (m, 2H), 7.82 (d, 1H), 7.78 (s, 1H), 7.67 (t, 1H), 7.25-7.32 (m, 5H), 3.48 (s, 2H), 2.93 (t, 2H), 2.38-2.55 (m, 10H), 1.97-2.05 (m, 2H). MS m/z 466.0 (M+1), 100%.

4a': 4-[3-(4-Pyridin-2-yl-piperazin-1-yl)-propyl]-6-(3-trifluoromethylphenyl)-pyrimidine-2-carbonitrile $^1$H NMR (CDCl$_3$): δ 8.35 (s, 1H), 8.32 (d, 1H), 8.18 (d, 1H), 7.82 (d, 1H), 7.80 (s, 1H), 7.68 (t, 1H), 7.47 (t, 1H), 6.60-6.65 (m, 2H), 3.51-3.53 (m, 4H), 2.98 (t, 2H), 2.54-2.57 (m, 4H), 2.48 (t, 2H), 2.03-2.11 (m, 2H). MS m/z 453.0 (M+1), 100%.

EXAMPLE 5a

4-(3-Isopropyl-phenyl)-6-propyl-pyrimidine-2-carbonitrile

A: 2-mercapto-6-propyl-pyrimidin-4-ol

Sodium (4.6 g) was added by portions at 0° C. to methanol (150 mL). The mixture was stirred at room temperature until dissolution. After cooling at 0° C., thiourea (11.0 g) was added by portions and the mixture was stirred until dissolution. Ethyl butyrylacetate (15.8 g) in methanol (200 mL) was added dropwise at 0° C. over 30 minutes. The mixture was refluxed for 9 h, then concentrated under reduced pressure. The residue was dissolved in water. After acidification with acetic acid until pH=6 and stirring for 1 h, the mixture was filtered. The precipitate was successively washed with water and isopropanol, then dried under reduced pressure to afford 2-mercapto-6-propyl-pyrimidin-4-ol (14.1) as white crystals (mp=220° C.).
$^1$H NMR (DMSO-d$_6$) δ: 12.2 (br. s, 2H); 5.68 (s, 1H); 2.32 (t, J=7 Hz, 2H); 1.60-1.50 (m, 2H); 0.88 (t, J=7 Hz, 3H).

B: 2-methylsulfanyl-6-propyl-pyrimidin-4-ol

A 1N solution of potassium hydroxide in methanol (110 mL) was added dropwise at 0° C. to a suspension of 2-mercapto-6-propyl-pyrimidin-4-ol (17.0 g) in methanol (220 mL). The mixture was stirred at room temperature for 15 minutes. After cooling at 0° C., iodomethane (6.8 mL) was added dropwise over 15 minutes. The mixture was stirred at room temperature for 6 hours, then filtered. The first precipitate was successively washed with methanol, water, isopropanol, then dried under reduced pressure. The filtrate was concentrated under reduced pressure, triturated with water, filtered. The second precipitate was successively washed with methanol, water, isopropanol, then dried under reduced pressure. Both precipitates were combined to afford 2-methylsulfanyl-6-propyl-pyrimidin-4-ol (15.5 g) as white crystals (mp=158° C.).
$^1$H NMR (DMSO-d$_6$) δ: 5.93 (s, 1H); 2.47 (s, 3H); 2.45-2.35 (m, 2H); 1.65-1.55 (m, 2H); 0.89 (t, J=7 Hz, 3H).

C: 4-chloro-2-methylsulfanyl-6-propyl-pyrimidine

A suspension of 2-methylsulfanyl-6-propyl-pyrimidin-4-ol (15.5 g) in phosphorous oxychloride (160 mL) was refluxed for 6 hours. The solvent was distilled off under reduced pressure. The residue was diluted with dichloromethane and poured in ice. The layers were separated, then the aqueous layer was extracted twice with ethyl acetate. The combined organic layers were dried over sodium sulphate, filtered and concentrated under reduced pressure to afford 4-chloro-2-methylsulfanyl-6-propyl-pyrimidine (17.5 g, 100%) as an orange oil.
$^1$H NMR (CDCl$_3$) δ: 6.85 (s, 1H); 2.7-2.6 (m, 2H); 2.57 (s, 3H); 1.8-1.7 (m, 2H); 0.97 (t, J=7 Hz, 3H).

D: 4-chloro-2-methanesulfonyl-6-propyl-pyrimidine m-Chloroperbenzoic acid (65.0 g, 378 mmol) was added by portions over 15 minutes to a solution of 4-chloro-2-methylsulfanyl-6-propyl-pyrimidine (17.5 g, 84 mmol) in DCM (350 mL) at 0° C. The mixture was stirred at room temperature for 24 hours then filtered. The precipitate was successively washed with small amount of DCM, an aqueous solution of sodium metabisulfite, water, and triturated with a saturated solution of sodium bicarbonate, filtered off then washed with water, dried under reduced pressure to afford 4-chloro-2-methanesulfonyl-6-propyl-pyrimidine (18.3 g, 93%) as an off white solid (mp=73° C.).
$^1$H NMR (CDCl$_3$) δ: 7.43 (s, 1H); 3.37 (s, 3H); 2.87 (t, J=7 Hz, 2H); 1.9-1.7 (m, 2H); 1.02 (t, J=7 Hz, 3H).

E: 4-(3-isopropyl-phenyl)-2-methanesulfonyl-6-propyl-pyrimidine

Potassium carbonate (0.850 g, 6 mmol), water (1 ml) and tetrakis(triphenylphosphine)palladium (0.695 g, 0.6 mmol) were successively added under a nitrogen atmosphere, to a mixture of 4-chloro-2-methanesulfonyl-6-propyl-pyrimidine (1.17 g, 5 mmol) and 3-isopropyl-phenylboronic acid (0.984 g, 6 mmol) in dimethoxyethane (40 mL). The mixture was refluxed for 18 hours then concentrated under reduced pressure. The residue was partitioned between ethyl acetate and water. The aqueous layer was extracted twice with ethyl acetate. The combined organic layers were dried over sodium sulphate, filtered and concentrated under reduced pressure. The residue was chromatographed over silica gel (eluent: Cyclohexane/Ethyl acetate 7/3) to afford a yellow oil which crystallised in pentane. After filtration, 4-(3-isopropyl-phenyl)-2-methanesulfonyl-6-propyl-pyrimidine (0.380 g) was obtained as an off white solid (mp=82° C.).
$^1$H NMR (CDCl$_3$) δ: 8.0-7.9 (m, 2H); 7.71 (s, 1H); 7.5-7.4 (m, 2H); 3.43 (s, 3H); 3.1-3.0 (m, 1H); 2.95-2.85 (m, 2H); 1.95-1.85 (m, 2H); 1.32 (d, J=7 Hz, 6H); 1.03 (t, J=7 Hz, 3H). MS m/z: 319.1 (M+1). HPLC (200-400 nm): 99.3%.

F: 4-(3-isopropyl-phenyl)-6-propyl-pyrimidine-2-carbonitrile

Sodium cyanide (65 mg, 1.32 mmol) was added at room temperature to 4-(3-isopropyl-phenyl)-2-methanesulfonyl-6-propyl-pyrimidine (211 mg) in DMSO (2 mL). The mixture was stirred at room temperature for 2 hours, then partitioned between ethyl acetate and water. The aqueous layer was extracted twice with ethyl acetate. The combined organic layers were washed with brine, dried over sodium sulphate, filtered and concentrated under reduced pressure. The residue was chromatographed over silica gel (eluent: Cyclohexane/Ethyl acetate 7/3) to afford a pink oil which crystallised in pentane. After filtration, 4-(3-isopropyl-phenyl)-2-cyano-6-propyl-pyrimidine (164 mg) was obtained as an off white solid (mp=64° C.).

$^1$H NMR (CDCl$_3$) δ: 7.98 (s, 1H); 7.90-7.85 (m, 1H); 7.71 (s, 1H); 7.5-7.4 (m, 2H); 3.10-2.95 (m, 1H); 2.85-2.75 (m, 2H); 1.90-1.80 (m, 2H); 1.32 (d, J=7 Hz, 6H); 1.02 (t, J=7 Hz, 3H). MS m/z: 266.1 (M+1). HPLC (200-400 nm): 98.5%.

The above described procedure was further applied, using the appropriate boronic acid derivatives, to the preparation of the following compounds:

5b: 4-Phenyl-6-propyl-pyrimidine-2-carbonitrile, $^1$H NMR (CDCl$_3$) δ: 8.15-8.05 (m, 2H); 7.71 (s, 1H); 7.60-7.45 (m, 3H); 2.90-2.80 (m, 2H); 1.90-1.80 (m, 2H); 1.03 (t, J=7 Hz, 3H). MS m/z: 224.1 (M+1). HPLC (200-400 nm): 97.1%.

5c: 4-(3-isopropyl-6-methoxy-phenyl)-6-propyl-pyrimidine-2-carbonitrile $^1$H NMR (CDCl$_3$) δ: 8.01 (s, 1H); 7.91 (s, 1H); 7.35 (d, J=8 Hz, 1H); 6.97 (d, J=8 Hz, 1H); 3.90 (s, 3H); 3.1-2.9 (m, 1H); 2.85-2.75 (m, 2H); 1.85-1.75 (m, 2H); 1.28 (d, J=7 Hz, 6H); 1.01 (t, J=7 Hz, 3H). MS m/z: 296.2 (M+1). HPLC (200-400 nm): 98.3%.

5d: 4-(3-Trifluoromethoxy-phenyl)-6-propyl-pyrimidine-2-carbonitrile $^1$H NMR (CDCl$_3$) δ: 8.05 (d, J=8 Hz, 1H); 7.98 (s, 1H); 7.71 (s, 1H); 7.58 (t, J=8 Hz, 1H); 7.42 (d, J=8 Hz, 1H); 2.9-2.8 (m, 2H); 1.9-1.8 (m, 2H); 1.03 (t, J=7 Hz, 3H). MS m/z: 308.1 (M+1). HPLC (200-400 nm): 97.1%.

5e: 4-(4-Fluoro-3-methyl-phenyl)-6-propyl-pyrimidine-2-carbonitrile $^1$H NMR (CDCl$_3$) δ: 7.99 (d, J=8 Hz, 1H); 7.95-7.90 (m, 1H); 7.65 (s, 1H); 7.15 (t, J=8 Hz, 1H); 2.9-2.8 (m, 2H); 2.37 (s, 3H); 1.9-1.8 (m, 2H); 1.02 (t, J=7 Hz, 3H). MS m/z: 256.1 (M+1). HPLC (200-400 nm): 97.1%.

5f: 4-(2,3-Dimethyl-phenyl)-6-propyl-pyrimidine-2-carbonitrile $^1$H NMR (CDCl$_3$) δ: 7.40-7.35 (m, 1H); 7.3-7.1 (m, 3H); 2.85-2.75 (m, 2H); 2.35 (s, 3H); 2.25 (s, 3H); 1.85-1.75 (m, 2H); 1.03 (t, J=7 Hz, 3H). MS m/z: 252.3 (M+1). HPLC (200-400 nm): 99.6%.

5g: 4-(3-Chloro-4-fluoro-phenyl)-6-propyl-pyrimidine-2-carbonitrile $^1$H NMR (CDCl$_3$) δ: 8.21 (d, J=8 Hz, 1H); 8.1-8.0 (m, 1H); 7.66 (s, 1H); 7.35-7.20 (m, 1H); 2.9-2.8 (m, 2H); 1.90-1.75 (m, 2H); 1.03 (t, J=7 Hz, 3H). MS m/z: 276/278 (M+1). HPLC (200-400 nm): 93.3%.

5h: 4-(3,5-Dichloro-phenyl)-6-propyl-pyrimidine-2-carbonitrile $^1$H NMR (CDCl$_3$) δ: 8.00 (s, 2H); 7.68 (s, 1H); 7.55 (s, 1H); 2.9-2.8 (m, 2H); 1.9-1.8 (m, 2H); 1.03 (t, J=7 Hz, 3H). MS m/z: 292/294 (M+1). HPLC (200-400 nm): 93.7%.

5i: 4-(3-Methyl-phenyl)-6-propyl-pyrimidine-2-carbonitrile $^1$H NMR (CDCl$_3$) δ: 7.94 (s, 1H); 7.88 (d, J=8 Hz, 1H); 7.71 (s, 1H); 7.45-7.35 (m, 2H); 2.9-2.8 (m, 2H); 2.47 (s, 3H); 1.9-1.8 (m, 2H); 1.03 (t, J=7 Hz, 3H). MS m/z: 238.2 (M+1). HPLC (200-400 nm): 99.1%.

EXAMPLE 6a 4-(3,5-Bis-trifluoromethyl-phenyl)-6-propyl-pyrimidine-2-carbonitrile A: 2-methanesulfonyl-4-propyl-6-trimethylstannanyl-pyrimidine Tetrakis(triphenylphosphine)palladium (2.48 g, 2.1 mmol) and hexamethyl-distannane (20 g, 61.4 mmol) were successively added under a nitrogen atmosphere to a mixture of 4-chloro-2-methanesulfonyl-6-propyl-pyrimidine (12.8 g, 54.5 mmol), lithium chloride (2.8 g, 66 mmol) and 2,6-di-tert-butyl-4-methylphenol (0.18 g, 0.82 mmol) in dioxane (240 mL). The mixture was refluxed for 3 hours then cooled to room temperature, and filtered. The filtrate was concentrated under reduced pressure. The residue was chromatographed over silica gel (eluent: Cyclohexane/Ethyl acetate 8/2) to afford 2-methanesulfonyl-4-propyl-6-trimethylstannanyl-pyrimidine (9.5 g, 48%) as a yellow oil.

$^1$H NMR (CDCl$_3$) δ: 7.51 (s, 1H); 3.39 (s, 3H); 2.81 (t, J=7 Hz, 2H); 1.9-1.8 (m, 2H); 1.02 (t, J=7 Hz, 3H); 0.44 (s, 9H).

B: 4-propyl-6-trimethylstannanyl-pyrimidine-2-carbonitrile

Sodium cyanide (0.63 g, 12.9 mmol) was added at room temperature to 2-methanesulfonyl-4-propyl-6-trimethylstannanyl-pyrimidine (2.34 g, 6.5 mmol) in DMSO (23 mL). The mixture was stirred at room temperature for 2 hours, then partitioned between ethyl acetate and water. The aqueous layer was extracted twice with ethyl acetate. The combined organic layers were washed with brine, dried over sodium sulphate, filtered and concentrated under reduced pressure. The residue was chromatographed over silica gel (eluent: Cyclohexane/Ethyl acetate 9/1) to give 4-propyl-6-trimethylstannanyl-pyrimidine-2-carbonitrile (1.53 g, 76%) as an off white solid (mp=62° C.).

$^1$H NMR (CDCl$_3$) δ: 7.47 (s, 1H); 2.80-2.65 (t, J=7 Hz, 2H); 1.8-1.7 (m, 2H); 0.99 (t, J=7 Hz, 3H); 0.41 (s, 9H).

C: 4-(3,5-bis-trifluoromethyl-phenyl)-6-propyl-pyrimidine-2-carbonitrile

Bis(triphenylphosphine)palladium dichloride (34 mg, 0.05 mmol) was added under a nitrogen atmosphere to a mixture of 4-propyl-6-trimethylstannanyl-pyrimidine-2-carbonitrile (155 mg, 0.50 mmol) and 3,5-bis-trifluoromethyl-bromobenzene (0.10 mL, 0.58 mmol) in dimethylformamide (3 mL). The mixture was refluxed for 4 hours then concentrated under reduced pressure. The residue was partitioned between ethyl acetate and water. The aqueous layer was extracted twice with ethyl acetate. The combined organic layers were concentrated under reduced pressure. The residue was chromatographed over silica gel (eluent: DCM) to afford a solid which was triturated in pentane. After filtration, 4-(3,5-bis-trifluoromethyl-phenyl)-6-propyl-pyrimidine-2-carbonitrile (63 mg, 35%) was obtained as an off white solid (mp=112° C.).

¹H NMR (CDCl₃) δ: 8.56 (s, 2H); 8.07 (s, 1H); 7.80 (s, 1H); 2.92 (t, J=8 Hz, 2H); 1.95-1.85 (m, 2H); 1.05 (t, J=7 Hz, 3H). MS m/z: 360.3 (M+1). HPLC-(200-400 nm): δ 99.4%.

The above described procedure was further applied, using the appropriate bromo- or iodo-phenyl derivatives, to the preparation of the following compounds:

6b: 4-(3-Chloro-phenyl)-6-propyl-pyrimidine-2-carbonitrile

¹H NMR (CDCl₃) δ: 8.10 (s, 1H); 7.99 (d, J=8 Hz, 1H); 7.69 (s, 1H); 7.6-7.4 (m, 2H); 2.86 (t, J=7 Hz, 2H); 1.90-1.75 (m, 2H); 1.03 (t, J=7 Hz, 3H). MS m/z: 258/260 (M+1). HPLC (200-400 nm): 94.9%.

6c: 4-(3,4-Dichloro-phenyl)-6-propyl-pyrimidine-2-carbonitrile

¹H NMR (CDCl₃) δ: 8.23 (s, 1H); 7.96 (d, J=8 Hz, 1H); 7.67 (s, 1H); 7.62 (d, J=8 Hz, 1H); 2.86 (t, J=8 Hz, 2H); 1.9-1.8 (m, 2H); 1.03 (t, J=7 Hz, 3H). MS m/z: 292/294 (M+1). HPLC (200-400 nm): 99.3%.

6d: 4-(4-Chloro-3-trifluoromethyl-phenyl)-6-propyl-pyrimidine-2-carbonitrile

¹H NMR (CDCl₃) δ: 8.42 (s, 1H); 8.26 (d, J=8 Hz, 1H); 7.75-7.65 (m, 2H); 2.87 (t, J=8 Hz, 2H); 1.9-1.8 (m, 2H); 1.04 (t, J=7 Hz, 3H). MS m/z: 326/328 (M+1). HPLC (200-400 nm): 98.9%.

6e: 4-(4-Cyano-3-methyl-phenyl)-6-propyl-pyrimidine-2-carbonitrile

¹H NMR (CDCl₃) δ: 8.10 (S, 1H); 7.99 (d, J=8 Hz, 1H); 7.77 (d, J=8 Hz, 1H); 7.73 (s, 1H); 2.88 (t, J=8 Hz, 2H); 2.68 (s, 3H); 1.9-1.8 (m, 2H); 1.03 (t, J=7 Hz, 3H). MS m/z: 263.2 (M+1). HPLC (200-400 nm): 99.5%.

6f: 4-(3-Chloro-4-methyl-phenyl)-6-propyl-pyrimidine-2-carbonitrile

¹H NMR (CDCl₃) δ: 8.11 (s, 1H); 7.91 (d, J=8 Hz, 1H); 7.66 (s, 1H); 7.39 (d, J=8 Hz, 1H); 2.84 (t, J=8 Hz, 2H); 2.47 (s, 3H); 1.9-1.8 (m, 2H); 1.03 (t, J=7 Hz, 3H). MS m/z: 272/274 (M+1). HPLC (200-400 nm): 99.3%.

6g: 4-(4-Methyl-3-trifluoromethyl-phenyl)-6-propyl-pyrimidine-2-carbonitrile

¹H NMR (CDCl₃) δ: 8.33 (s, 1H); 8.20 (d, J=8 Hz, 1H); 7.71 (s, 1H); 7.47 (d, J=8 Hz, 1H); 2.86 (t, J=7 Hz, 2H); 2.59 (s, 3H); 1.90-1.75 (m, 2H); 1.03 (t, J=7 Hz, 3H). MS m/z: 306.1 (M+1). HPLC (200-400 nm): 97.8%.

6h: 4-(4-Fluoro-3-trifluoromethyl-phenyl)-6-propyl-pyrimidine-2-carbonitrile

¹H NMR (CDCl₃) δ: 8.4-8.3 (m, 2H); 7.71 (s, 1H); 7.39 (t, J=9 Hz, 1H); 2.88 (t, J=7 Hz, 2H); 1.9-1.8 (m, 2H); 1.03 (t, J=7 Hz, 3H). MS m/z: 310.1 (M+1). HPLC (200-400 nm): 94.0%.

6l: 4-(3,4-Dimethyl-phenyl)-6-propyl-pyrimidine-2-carbonitrile

¹H NMR (CDCl₃) δ: 7.90 (s, 1H), 7.82 (d, J=7.6 Hz, 1H), 7.66 (s, 1H), 7.27 (d, J=7.6 Hz, 1H), 2.82 (t, J=7.8 Hz, 2H), 2.37 (s, 3H), 2.35 (s, 3H), 1.84 (quint, 2H), 1.01 (t, J=7.4 Hz, 3H). MS m/z: 252 (M+1). HPLC (200-400 nm): 99.7%.

6m: 4-(3-Fluoro-4-methyl-phenyl)-6-propyl-pyrimidine-2-carbonitrile

¹H NMR (CDCl₃) δ: 7.79 (d, 2H), 7.65 (s, 1H), 7.34 (t, J=7.8 Hz, 1H), 2.84 (t, J=7.6 Hz, 2H), 2.37 (s, 3H), 1.83 (m, 2H), 1.02 (t, J=7.2 Hz, 3H). MS m/z: 256 (M+1). HPLC (200-400 nm): 98.9%.

The above described procedure was modified for the preparation of the following compounds using the appropriate bromo- or iodo-phenyl derivatives in refluxing 1,2-dichloroethane as solvent instead of DMF.

6n: 4-(4-Chloro-3-fluoro-phenyl)-6-propyl-pyrimidine-2-carbonitrile

¹H NMR (CDCl₃) δ: 8.0-7.9 (m, 1H); 7.86 (d, J=8 Hz, 1H); 7.67 (s, 1H); 7.6-7.5 (m, 1H); 2.86 (t, J=8 Hz, 2H); 1.95-1.80 (m, 2H); 1.03 (t, J=7 Hz, 3H). MS m/z: 276/278 (M+1). HPLC (200-400 nm): 97.6%.

6o: 4-(3-Chloro-4-cyano-phenyl)-6-propyl-pyrimidine-2-carbonitrile

¹H NMR (CDCl₃) δ: 8.28 (s, 1H); 8.11 (d, J=8 Hz, 1H); 7.85 (d, J=8 Hz, 1H); 7.73 (s, 1H); 2.89 (t, J=7 Hz, 2H); 1.95-1.80 (m, 2H); 1.03 (t, J=7 Hz, 3H). MS m/z: 283/285 (M+1). HPLC (200-400 nm): 98.1%.

6r: 4-Propyl-6-(3,4,5-trifluoro-phenyl)-pyrimidine-2-carbonitrile

¹H NMR (CDCl₃) δ: 7.81 (m, 2H), 7.63 (s, 1H), 2.87 (t, J=7.6 Hz, 2H), 1.85 (m, 2H), 1.03 (t, J=8 Hz, 3H). MS m/z: 278 (M+1). HPLC (200-400 nm): 98.6%.

EXAMPLE 7a

4-[3-(Pyridin-2-yl-amino)-propyl]-6-(3-trifluoromethylphenyl)-pyrimidine-2-carbonitrile hydrochloride To a solution of 4-(3-oxopropyl)-6-(trifluoromethylphenyl)-pyrimidine-2-carbonitrile (91 mg) in dichloromethane (6 mL) was added acetic acid (36 μL, 2 equiv.) followed by 2-aminopyridine (1.3 equiv.). The solution was stirred at room temperature for 15 min then sodium triacetoxy borohydride (2 equiv.) was added and the mixture stirred for 18 h at room temperature. Cold, dilute sodium carbonate solution was added, the mixture stirred for 10 min and the organic layer separated. The crude product was chromatographed on a 2 g silica column, eluting with dichloromethane:ethanol 99:1 to give 4-[3-(pyridin-2-yl-amino)-propyl]-6-(3-trifluoromethylphenyl)-pyrimidin-2-carbonitrile as free base. The free base was then dissolved in DCM, and HCl (1M in ether) was added. Solvent was then removed under reduced pressure. The residue was redissolved in DCM and product was precipitated by adding diethyl ether to provide 4-[3-(pyridin-2-yl-amino)-propyl]-6-(3-trifluoromethylphenyl)-pyrimidin-2-carbonitrile as hydrochloric acid salt.

¹H NMR (CD₃OD): δ 8.51 (s, 1H), 8.48 (d, 1H), 8.28 (s, 1H), 7.90 (s, 1H), 7.89 (t, 1H), 7.81 (d, 1H), 7.79 (t, 1H), 7.08 (d, 1H), 6.89 (t, 1H), 3.51 (t, 2H), 3.12 (t, 2H), 2.31-2.20 (m, 2H). MS m/z 384.0 (M+1).

The procedure described above was further applied, using the appropriate amine, to prepare the following compounds as free base or as the corresponding hydrochloric acid salt:

7b: 4-[3-(5-Chloropyridin-2-yl-amino)-propyl]-6-(3-trifluoromethylphenyl)-pyrimidine-2-carbonitrile ¹H NMR (CDCl₃): δ 8.33 (s, 1H), 8.28 (d, 1H), 7.99 (s, 1H), 7.84 (d, 1H), 7.76 (s, 1H), 7.68 (t, 1H), 7.33 (d, 1H), 6.33 (d, 1H), 4.47 (brs, 1H), 3.48-3.40 (m, 2H), 3.01 (t, 2H), 2.22-2.13 (m, 2H). MS m/z 418.1 (M+1)

7c: 4-[3-(4-Methylpyridin-2-yl-amino)-propyl]-6-(3-trifluoromethylphenyl)-pyrimidine-2-carbonitrile ¹H NMR (CDCl₃): δ 8.31 (s, 1H), 8.27 (d, 1H), 7.91 (d, 1H), 7.82 (d, 1H), 7.75 (s, 1H), 7.66 (t, 1H), 6.38 (d, 1H), 6.15 (s, 1H), 4.42 (brs, 1H), 3.47-3.40 (m, 2H), 3.03 (t, 2H), 2.20-2.13 (m, 2H), 2.19 (s, 3H). MS m/z 398.1 (M+1)

7d: 4-[3-(1-Methylbenzimidazol-2-yl-amino)-propyl]-6-(3-trifluoromethylphenyl)-pyrimidine-2-carbonitrile ¹H NMR (CDCl₃): δ 8.31 (s, 1H), 8.16 (d, 1H), 7.79 (d, 1H), 7.78 (s, 1H), 7.60 (t, 1H), 7.41 (d, 1H), 7.09-7.02 (m, 1H), 7.02-6.96 (m, 2H), 4.38 (brs, 1H), 3.74-3-68 (m, 2H), 3.43 (s, 3H), 3.07 (t, 2H), 2.34-2.26 (m, 2H). MS m/z 437.1 (M+1)

7e: 4-[3-(4-Trifluoromethylpyridin-2-yl-amino)-propyl]-6-(3-trifluoromethylphenyl)-pyrimidine-2-carbonitrile ¹H NMR (dmso-d6): δ 8.50 (d, 1H), 8.49 (s, 1H), 8.46 (s, 1H), 8.14 (d, 1H), 7.99 (d, 1H), 7.84 (t, 1H), 7.11 (t, 1H), 6.64 (d, 1H), 6.63 (s, 1H), 3.43-3.36 (m, 2H), 2.97 (t, 2H), 2.12-2.04 (m, 2H). MS m/z 452.1 (M+1)

7f: 4-[3-(Isoquinolin-3-yl-amino)-propyl]-6-(3-trifluoromethylphenyl)-pyrimidine-2-carbonitrile ¹H NMR (CDCl₃): δ 8.80 (s, 1H), 8.30 (s, 1H), 8.20 (d, 1H), 7.79 (d, 1H), 7.72 (s, 1H), 7.71 (d, 1H), 7.60 (t, 1H), 7.51 (d, 1H), 7.46 (t, 1H), 7.19 (t, 1H), 6.49 (s, 1H), 4.66 (brs, 1H), 3.48-3.42 (m, 2H), 3.07 (t, 2H), 2.29-2.22 (m, 2H). MS m/z 434.3 (M+1)

7g: 4-[3-(3,5-Difluoropyridin-2-yl-amino)-propyl]-6-(3-trifluoromethylphenyl)-pyrimidine-2-carbonitrile ¹H NMR (CDCl₃): δ 8.32 (s, 1H), 8.30 (d, 1H), 7.83 (d, 1H), 7.79 (d, 1H), 7.77 (s, 1H), 7.68 (t, 1H), 7.05-6.97 (m, 1H), 4.60 (brs, 1H), 3.58 (q, 2H), 3.02 (t, 2H), 2.24-2.16 (m, 2H). MS m/z 420.0 (M+1)

7h: 4-[3-(1-Methyl-trifluoroethylamino)-propyl]-6-(3-trifluoromethylphenyl)-pyrimidine-2-carbonitrile hydrochloride ¹H NMR (CD₃OD): δ 8.52 (s, 1H), 8.50 (d, 1H), 8.29 (s, 1H), 7.91 (d, 1H), 7.80 (t, 1H), 4.35-4.24 (m, 1H), 3.42-3.26 (m, 2H), 3.12 (t, 2H), 2.40-2.22 (m, 2H), 1.59 (d, 3H). MS m/z 403.1 (M+1)

7i: 4-[3-(2-Amino-2-oxoethyl-methylamino)-propyl]-6-(3-trifluoromethylphenyl)-pyrimidine-2-carbonitrile hydrochloride ¹H NMR (CD₃OD): δ 8.53 (s, 1H), 8.50 (d, 1H), 8.27 (s, 1H), 7.91 (d, 1H), 7.79 (t, 1H), 4.01 (s, 2H), 3.37-3.31 (m, 2H), 3.08 (t, 2H), 2.98 (s, 3H), 2.37-2.27 (m, 2H). MS m/z 378.3 (M+1)

7j: 4-[3-(2-Methoxy-2-oxoethylamino)-propyl]-6-(3-trifluoromethylphenyl)-pyrimidine-2-carbonitrile hydrochloride (isolated as minor product from 4s' below)

¹H NMR (CD₃OD): δ 8.52 (s, 1H), 8.49 (d, 1H), 8.27 (s, 1H), 7.91 (d, 1H), 7.79 (t, 1H), 4.03 (s, 2H), 3.85 (s, 3H), 3.21 (t, 2H), 3.09 (t, 2H), 2.32-2.22 (m, 2H). MS m/z 379.1 (M+1)

7k: 4-[3-(Pyrimidin-2-yl-amino)-propyl]-6-(3-trifluoromethylphenyl)-pyrimidin-2-carbonitrile hydrochloride ¹H NMR (CD₃OD): δ 8.50 (s, 1H), 8.47 (m, 2H), 8.24 (s, 1H), 7.90 (d, 1H), 7.78 (t, 1H), 6.85 (t, 1H), 3.59 (t, 2H), 3.06 (t, 2H), 2.21 (p, 2H). MS m/z 385.0 (M+1).

7l: 4-[3-(6-Methoxy-pyrimidin-4-yl-amino)-propyl]-6-(3-trifluoromethylphenyl)-pyrimidin-2-carbonitrile hydrochloride ¹H NMR (CD₃OD): δ 8.52 (s, 1H), 8.48 (d, 1H), 8.37 (s, 1H), 8.27 (s, 1H), 7.91 (d, 1H), 7.79 (t, 1H), 6.10 (brs, 1H), 4.06 (s, 3H), 3.63 (brs, 2H), 3.07 (brs, 2H), 2.22 (brs, 2H).). MS m/z 415.0 (M+1).

EXAMPLE 8a

4-[3-(Methylcarbamoylmethyl-amino)-propyl]-6-(3-trifluoromethylphenyl)-pyrimidine-2-carbonitrile Trifluoroacetic Acid Salt To a stirred solution of 4-(3-oxo-propyl)-6-(3-trifluoromethylphenyl)-pyrimidine-2-carbonitrile (50 mg) in methanol (1 mL) was added glycine methyl amide hydrochloride (41 mg) and acetic acid (12 µL). The mixture was stirred for 5 minutes then sodium triacetoxy borohydride (42 mg) was added and stirring was continued at room temperature overnight. Methanol was removed in vacuo and the resulting residue dissolved in DCM (20 mL) and washed with saturated sodium bicarbonate and water (1:1, 2×20 mL). The organic layer was separated, dried over sodium sulphate and evaporated to yield crude product as an oil. Purification by preparative-HPLC afforded the TFA salt of 4-[3-(methylcarbamoyl-methyl-amino)-propyl]-6-(3-trifluoromethylphenyl)-pyrimidine-2-carbonitrile as a white solid (13 mg).

¹H NMR (MeOD): δ 8.55 (s, 1H), 8.48 (d, 1H), 8.24 (s, 1H), 7.88 (d, 1H), 7.80 (t, 1H), 3.80 (s, 2H), 3.15 (t, 2H), 3.08 (t, 2H), 2.75 (s, 3H), 2.22 (m, 2H). MS m/z 378.4 (M+1), 100%.

The procedure described above was further applied, using the appropriate amine derivative, to prepare the following compounds:

8b: 4-[3-(2-Dimethylcarbamoyl-pyrrolidin-1-yl)-propyl]-6-(3-trifluoromethylphenyl)-pyrimidine-2-carbonitrile Trifluoroacetic Acid Salt ¹H NMR (MeOD): δ 8.55 (s, 1H), 8.48 (d, 1H), 8.28 (s, 1H), 7.91 (d, 1H), 7.80 (m, 1H), 4.65 (t, 1H), 3.88 (m, 1H), 3.31 (m, 2H), 3.22 (m, 1H), 3.08 (m, 5H), 3.01 (s, 3H), 2.68 (m 1H), 2.22 (m, 3H), 2.24 (m, 2H). MS m/z 432.4 (M+1), 100%.

8c: 4-[3-(Carbamoylmethyl-amino)-propyl]-6-(3-trifluoromethylphenyl)-pyrimidine-2-carbonitrile Trifluoroacetic Acid Salt $^1$H NMR (MeOD): δ 8.55 (s, 1H), 8.48 (d, 1H), 8.28 (s, 1H), 7.91 (d, 1H), 7.80 (t, 1H), 3.85 (s, 2H), 3.18 (t, 2H), 3.08 (t, 2H), 2.26 (m, 2H). MS m/z 364.3 (M+1), 100%.

EXAMPLE 9a 4-(3-Piperazin-1-yl-propyl)-6-(3-trifluoromethylphenyl)-pyrimidine-2-carbonitrile Trifluoroacetic Acid Salt To a stirred solution of 4-(3-oxo-propyl)-6-(3-trifluoromethylphenyl)-pyrimidine-2-carbonitrile (50 mg) in dichloromethane (1 mL) was added tert-butyl 1-piperazine carboxylate (61 mg) and acetic acid (12 μL). The mixture was stirred at room temperature for five minutes then sodium triacetoxyborohydride (42 mg) was added and stirring continued overnight. The reaction mixture was diluted with dichloromethane (20 mL) and washed with saturated sodium bicarbonate and water (1:1, 2×20 mL). Organics were separated, dried over sodium sulphate, filtered, and solvent was removed under reduced pressure. The resulting residue was dissolved in diethyl ether (1 mL), HCl in ether was added (2M, 72 μL) and the reaction was stirred overnight. The mixture was diluted with ether (10 mL), washed with saturated sodium bicarbonate and water (1:1, 2×10 mL), dried over sodium sulphate, filtered, and solvent was removed under reduced pressure to yield crude product. Purification by preparative-HPLC afforded the TFA salt of 4-(3-piperazin-1-yl-propyl)-6-(3-trifluoromethylphenyl)-pyrimidine-2-carbonitrile.

$^1$H NMR (MeOD): δ 8.51 (s, 1H), 8.48 (d, 1H), 8.25 (s, 1H), 7.90 (d, 1H), 7.78 (d, 1H), 3.56 (m, 4H), 3.30 (m, 6H), 3.08 (t, 2H), 2.32 (m, 2H). MS m/z 376.4 (M+1), 100%.

The following compound is also prepared by the same procedure:

9b: 4-(3-[1,4]Diazepan-1-yl-propyl)-6-(3-trifluoromethylphenyl)-pyrimidine-2-carbonitrile Trifluoroacetic Acid Salt To a stirred solution of 4-(3-oxo-propyl)-6-(3-trifluoromethylphenyl)-pyrimidine-2-carbonitrile (50 mg) in dichloromethane (1 mL) was added tert-butyl 1-homopiperazine carboxylate (75 μL) and acetic acid (12 μL). The mixture was stirred at room temperature for five minutes then sodium triacetoxyborohydride (42 mg) was added and stirring continued overnight. The reaction mixture was diluted with dichloromethane (20 mL) and washed with saturated sodium bicarbonate and water (1:1, 2×20 mL). Organics were separated, dried over sodium sulphate, filtered, and solvent was removed under reduced pressure. The resulting residue was dissolved in THF (500 μL) and trifluoroacetic acid (100 μL) was added. The reaction was stirred at room temperature for 2 hours then solvent was removed under reduced pressure to yield the crude product. Purification by preparative-HPLC afforded the TFA salt of 4-(3-[1,4]diazepan-1-yl-propyl)-6-(3-trifluoromethylphenyl)-pyrimidine-2-carbonitrile.

$^1$H NMR (MeOD): δ 8.52 (s, 1H), 8.48 (d, 1H), 8.25 (s, 1H), 7.91 (d, 1H), 7.79 (t, 1H), 3.78 (m, 2H), 3.70 (m, 2H), 3.59 (m, 2H), 3.45 (t, 2H), 3.38 (t, 2H), 3.31 (t, 2H), 2.32 (m, 4H). MS m/z 390.3 (M+1), 100%.

EXAMPLE 10a

4-[3-(Carboxymethyl-amino)-propyl]-6-(3-trifluoromethylphenyl)-pyrimidine-2-carbonitrile Trifluoroacetic Acid Salt To a stirred solution of 4-(3-oxo-propyl)-6-(3-trifluoromethylphenyl)-pyrimidine-2-carbonitrile (50 mg) in methanol (1 mL) was added glycine (25 mg), followed by water (100 μL) and acetic acid (12 μL). The mixture was stirred at room temperature for five minutes then solid supported cyanoborohydride (77 mg, 2.57 mmol/g) was added and stirring continued overnight. The reaction mixture was filtered and the filtrate concentrated under reduced pressure to yield crude product. Purification by preparative-HPLC afforded the TFA salt of 4-[3-(carboxymethyl-amino)-propyl]-6-(3-trifluoromethylphenyl)-pyrimidine-2-carbonitrile.

$^1$H NMR (MeOD): δ 8.55 (s, 1H), 8.48 (d, 1H), 8.25 (s, 1H), 7.91 (d, 1H), 7.80 (t, 1H), 3.91 (s, 2H), 3.17 (t, 2H), 3.08 (t, 2H), 2.28 (m, 2H). MS m/z 365.0 (M+1), 100%.

The procedure described above was further applied, using the appropriate amine derivatives, to prepare the following compounds:

10b: 4-[3-(2-Carbamoyl-ethylamino)-propyl]-6-(3-trifluoromethylphenyl)-pyrimidine-2-carbonitrile Trifluoroacetic Acid Salt $^1$H NMR (MeOD): δ 8.51 (s, 1H), 8.47 (d, 1H), 8.25 (s, 1H), 7.90 (d, 1H), 7.78 (t, 1H), 3.32 (t, 2H), 3.19 (t, 2H), 3.09 (t, 2H), 2.70 (t, 2H), 2.27 (m, 2H). MS m/z 378.3 (M+1), 100%.

10c: 4-[3-Carboxymethyl-methyl-amino)-propyl]-6-(3-trifluoromethylphenyl)-pyrimidine-2-carbonitrile Trifluoroacetic Acid Salt $^1$H NMR (MeOD): δ 8.55 (s, 1H), 8.48 (d, 1H), 8.25 (s, 1H), 7.91 (d, 1H), 7.80 (t, 1H), 4.14 (s, 2H), 3.38 (t, 2H), 3.08 (t, 2H), 3.02 (s, 3H), 2.35 (m, 2H). MS m/z 378.8 (M+1).

EXAMPLE 11a

4-{3-[2-(1-Methyl-pyrrolidin-2-yl)-ethylamino]-propyl}-6-(3-trifluoromethylphenyl)-pyrimidine-2-carbonitrile Trifluoroacetic Acid Salt To a stirred solution of 4-(3-oxo-propyl)-6-(3-trifluoromethylphenyl)-pyrimidine-2-carbonitrile (50 mg) in methanol (1 mL) was added 2-(2-Aminoethyl)-1-methylpyrrolidine (48 μL) and acetic acid (12 μL). The mixture was stirred at room temperature for five minutes then solid supported cyanoborohydride (77 mg, 257 mmol/g) was added and stirring continued overnight. The reaction mixture was filtered and the filtrate concentrated under reduced pressure to yield crude product. Purification by preparative-HPLC afforded the TFA salt of 4-{3-[2-(1-methyl-pyrrolidin-2-yl)-ethylamino]-propyl}-6-(3-trifluoromethylphenyl)-pyrimidine-2-carbonitrile.

$^1$H NMR (MeOD): δ 8.52 (s, 1H), 8.48 (d, 1H), 8.25 (s, 1H), 7.90 (d, 1H), 7.79 (t, 1H), 3.75 (m, 1H), 3.38 (m, 1H), 3.19 (m, 5H), 3.12 (t, 2H), 2.96 (s, 3H), 2.40 (m, 2H), 2.27 (t, 2H), 2.15 (m, 2H), 2.05 (m, 1H), 1.82 (m, 1H). MS m/z 418.3 (M+1), 100%.

The procedure described above was further applied, using the appropriate amine derivatives, to prepare the following compounds:

11b: 4-[3-(2-Pyrrolidin-1-yl-ethylamino)-propyl]-6-(3-trifluoromethylphenyl)-pyrimidine-2-carbonitrile Trifluoroacetic Acid Salt $^1$H NMR (MeOD): δ 8.51 (s, 1H), 8.48 (d, 1H), 8.25 (s, 1H), 7.90 (d, 1H), 7.78 (t, 1H), 3.61 (t, 2H), 3.50 (m, 6H), 3.24 (t, 2H), 3.10 (t, 2H), 3.29 (m, 2H), 2.13 (m, 4H). MS m/z 404.5 (M+1), 100%.

11c: 4-{3-[(1-Ethyl-pyrrolidin-2-yl-methyl)-amino]-propyl}-6-(3-trifluoromethylphenyl)-pyrimidine-2-carbonitrile Trifluoroacetic Acid Salt $^1$H NMR (MeOD): δ 8.51 (s, 1H), 8.48 (d, 1H), 8.25 (s, 1H), 7.90 (d, 1H), 7.78 (t, 1H), 3.82 (m, 1H), 3.78 (m, 1H), 3.68 (m, 1H), 3.55 (m, 1H), 3.45 (m, 1H), 3.31 (m, 1H), 3.27 (t, 2H), 3.20 (m, 1H), 3.11 (t, 2H), 2.50 (m, 1H), 2.31 (m, 2H), 2.19 (m, 2H), 2.05 (m, 1H), 1.38 (t, 3H). MS m/z 418.1 (M+1), 100%.

11d: 4-[3-(1-Aza-bicyclo[2.2.2]oct-3-yl-amino)-propyl]-6-(3-trifluoromethylphenyl)-pyrimidine-2-carbonitrile Trifluoroacetic Acid Salt $^1$H NMR (MeOD): δ 8.51 (s, 1H), 8.48 (d, 1H), 8.25 (s, 1H), 7.90 (d, 1H), 7.78 (t, 1H), 3.95 (m, 1H), 3.86 (m, 1H), 3.42 (m, 5H), 3.25 (t, 2H), 3.11 (t, 2H), 2.57 (m, 1H), 2.32 (m, 2H), 2.20 (m, 2H), 2.05 (m, 2H). MS m/z 416.1 (M+1), 100%.

11e: 4-[3-(2-Morpholin-4-yl-ethylamino)-propyl]-6-(3-trifluoromethylphenyl)-pyrimidine-2-carbonitrile Trifluoroacetic Acid Salt $^1$H NMR (MeOD): δ 8.52 (s, 1H), 8.48 (d, 1H), 8.25 (s, 1H), 7.90 (d, 1H), 7.80 (t, 1H), 3.87 (t, 4H), 3.45 (t, 2H), 3.23 (m, 4H), 3.10 (t, 6H), 2.28 (m, 2H). MS m/z 420.1 (M+1), 100%.

11f: 4-[3-(2-Methoxy-ethylamino)-propyl]-6-(3-trifluoromethylphenyl)-pyrimidine-2-carbonitrile Trifluoroacetic Acid Salt $^1$H NMR (MeOD): δ 8.52 (s, 1H), 8.48 (d, 1H), 8.24 (s, 1H), 7.90 (d, 1H), 7.79 (t, 1H), 3.66 (t, 2H), 3.42 (s, 3H), 3.25 (t, 2H), 3.16 (t, 2H), 3.08 (t, 2H), 2.24 (m, 2H). MS m/z 365.0 (M+1), 100%.

11g: 4-{3-[2-(2-Oxo-imidazolidin-1-yl)-ethylamino]-propyl}-6-(3-trifluoromethylphenyl)-pyrimidine-2-carbonitrile Trifluoroacetic Acid Salt $^1$H NMR (MeOD): δ 8.52 (s, 1H), 8.48 (d, 1H), 8.25 (s, 1H), 7.90 (d, 1H), 7.79 (t, 1H), 3.53 (m, 2H), 3.46 (m, 4H), 3.24 (m, 2H), 3.19 (t, 2H), 3.08 (t, 2H), 2.25 (m, 2H). MS m/z 419.0 (M+1), 100%.

11h: 4-[3-(2-Dimethylamino-ethylamino)-propyl]-6-(3-trifluoromethylphenyl)-pyrimidine-2-carbonitrile Trifluoroacetic Acid Salt $^1$H NMR (MeOD): δ 8.52 (s, 1H), 8.48 (d, 1H), 8.28 (s, 1H), 7.91 (d, 1H), 7.80 (t, 1H), 3.54 (s, 4H), 3.28 (t, 2H), 3.12 (t, 2H), 2.98 (s, 6H), 2.30 (m, 2H). MS m/z 378.4 (M+1), 100%.

11i: 4-[3-(2-Acetylamino-ethylamino)-propyl]-6-(3-trifluoromethylphenyl)-pyrimidine-2-carbonitrile Trifluoroacetic Acid Salt $^1$H NMR (MeOD): δ 8.52 (s, 1H), 8.48 (d, 1H), 8.25 (s, 1H), 7.90 (d, 1H), 7.79 (t, 1H), 3.51 (t, 2H), 3.18 (m, 4H), 3.08 (t, 2H), 2.25 (m, 2H), 1.99 (s, 3H). MS m/z 392.1 (M+1), 100%.

EXAMPLE 12

4-(3-Hydroxy-1-propyl)-6-(3,4-dimethylphenyl)-pyrimidine-2-carbonitrile

A: 2-methylsulfanyl-4-(3-hydroxypropyl)-6-(3,4-dimethylphenyl)pyrimidine

To a stirred suspension of sodium hydride (60% in parafin oil, 20 g) in diethyl ether (1 L) at 0° C. was added ethanol (1 ml). To above mixture was then added gamma-butyrolactone (18 g), followed by dropwise addition of diethyl ether solution (100 ml) 3',4'-dimethylacetophenone (29.6 g) in 30 minutes. The mixture was allowed to stir at room temperature for 72 hours. Ethanol (20 ml) was then added to destroy excess sodium hydride, followed by addition of aqueous solution of ammonium chloride (20 g in 300 ml water). Organic layer separated and washed with diluted hydrochloric acid (0.1N, 500 ml), then with water (2×200 ml). Ether layer was then dried over sodium sulphate, solvent removed under reduced pressure. The residue was then mixed with S-methyl isothiouranium iodide salt (37 g). The mixture was heated at 130° C. for 4 hours. After cooling to room temperature, triethylamine (45 ml) and methanol (50 ml) were added, and the mixture was heated to reflux with an oil bath at 85° C. for 6 hours. After removal of solvent and triethyl amine at reduced pressure, the residue was taken into ethyl acetate (500 ml) and water (500 ml). Organic layer was then separated, washed with diluted hydrochloric acid (0.1N, 500 ml), followed with water (2×300 ml). Organic layer was then dried, solvent removed under reduced pressure. The residue was columned on silica gel using petrol and ethyl acetate (1:1) as eluant to give 2-methylsulfanyl-4-(3-hydroxypropyl)-6-(3,4-dimethylphenyl)pyrimidine (17.5 g). $^1$H NMR (CDCl$_3$): δ 7.84 (s, 1H), 7.80 (d, 1H), 7.15-7.25 (m, 2H), 3.72 (t, 2H), 2.87 (t, 2H), 2.63 (s, 3H), 2.34 (s, 3H), 2.32 (s, 3H), 2.03 (m, 2H).

B: 4-(3-hydroxypropyl)-6-(3,4-dimethylphenyl)pyrimidine-2-carbonitrile

To the solution of 2-methylsulfanyl-4-(3-hydroxypropyl)-6-(3,4-dimethyl-phenyl)pyrimidine (5.8 g) in a mixed solvent of methanol and water (110 ml, 10:1) was added OXONE (35 g). The mixture was stirred at room temperature for 3 hours, then diluted with ethyl acetate (500 ml). The mixture was washed with water (3×500 ml). Organic layer dried over sodium sulphate, solvent removed under reduced pressure to give 2-methanesulphonyl-4-(3-hydroxypropyl)-6-(3,4-dimethylphenyl)-pyrimidine as crude product. To a stirred solution of above 2-methylsulphonyl-4-(3-hydroxypropyl)-6-(3,4-dimethylphenyl)pyrimidine in dimethylsulfoxide (50 mL), was added sodium cyanide (2.9 g). The mixture was stirred at room temperature for 4 hours, then poured into ethyl acetate (300 mL) and washed with water (2×200 mL). The organic layer was dried over sodium sulphate, solvent evaporated at reduced pressure, the above residue was flashed on silica gel using Petrol/EtOAc (1:1) as eluent to give 4-(3-Hydroxy-propyl)-6-(3,4-dimethylphenyl)-pyrimidine-2-carbonitrile as product (4.8 g).

¹H NMR (CDCl₃): δ 8.01 (s, 1H), 7.96 (s, 1H), 7.89 (d, 1H), 7.25 (d, 1H), 3.64 (t, 2H), 2.93 (t, 2H), 2.36 (s, 3H), 2.34 (s, 3H), 2.0 (m, 2H). MS m/z 268 (M+1), 100%.

EXAMPLE 13a 4-(3,4-Dimethylphenyl)-6-[3-(pyridin-2-yl-amino)-propyl]-pyrimidine-2-carbonitrile Hydrochloride A: 4-(3-oxo-1-propyl)-6-(3,4-dimethylphenyl)-pyrimidine-2-carbonitrile Dess-Martin periodinane (4.2 g) was added to a solution of 4-(3-hydroxy-propyl)-6-(3,4-dimethylphenyl)-pyrimidine-2-carbonitrile (2.0 g) in dichloromethane (100 mL), and the resulting suspension stirred at room temperature for 45 min. The mixture was then washed with water (3×100 mL), dried over sodium sulphate, and evaporated at reduced pressure. The residue was flashed on silica gel using Petrol/EtOAc (2:1) to afford 4-(3-oxo-propyl)-6-(3,4-dimethylphenyl)-pyrimidine-2-carbonitrile as a white solid (1.9 g).
¹H NMR (CDCl₃): δ 7.87 (s, 1H), 7.8 (d, 1H), 7.75 (s, 1H), 7.25 (d, 1H), 3.16 (t, 2H), 3.09 (t, 2H), 2.36 (s, 3H), 2.34 (s, 3H). MS m/z 266 (M+1), 100%.

B: 4-(3,4-dimethylphenyl)-6-[3-(pyridin-2-yl-amino)-propyl]-pyrimidine-2-carbonitrile Hydrochloride To a solution of 4-(3-oxo-propyl)-6-(3,4-dimethylphenyl)-pyrimidine-2-carbonitrile (91 mg) in dichloromethane (6 mL) was added acetic acid (2 equiv.) followed by 2-aminopyridine (1.3 equiv.). The solution was stirred at room temperature for 15 min then sodium triacetoxy borohydride (2 equiv.) was added and the mixture stirred for 18 h at room temperature.
Cold, dilute sodium carbonate solution was added, the mixture stirred for 10 min and the organic layer separated and solvent removed under reduced pressure. The crude product was chromatographed on a 2 g silica column, eluting with dichloromethane:ethanol (99:1) to afford product as free base. The free base was then dissolved in DCM, and HCl (1M in ether) was added. Solvent was then removed under reduced pressure. The residue was redissolved in DCM and product was precipitated by adding diethyl ether to provide 4-(3,4-dimethylphenyl)-6-[3-(pyridin-2-yl-amino)-propyl]-pyrimidine-2-carbonitrile hydrochloride (60 mg).
¹H NMR (CD₃OD): δ 8.09 (s, 1H), 8.00 (s, 1H), 7.95-7.86 (m, 2H), 7.83 (d, 1H), 7.32 (d, 1H), 7.07 (d, 1H), 6.88 (t, 1H), 3.48 (t, 2H), 3.05 (t, 2H), 2.29-2.19 (m, 2H). MS m/z 344.1 (M+1)
Using the appropriate amines, the following compounds were prepared as either free base or corresponding hydrochloric acid salt.

13b: 4-(3,4-Dimethylphenyl)-6-[3-(4-methylpyridin-2-yl-amino)-propyl]-pyrimidine-2-carbonitrile Hydrochloride ¹H NMR (CD₃OD): δ 8.08 (s, 1H), 7.98 (s, 1H), 7.92 (d, 1H), 7.69 (d, 1H), 7.31 (d, 1H), 6.82 (s, 1H), 6.74 (d, 1H), 3.37 (t, 2H), 3.04 (t, 2H), 2.37 (s, 6H), 2.35 (s, 3H), 2.28-2.18 (m, 2H). MS m/z 358.0 (M+1)

13c: 4-[3-(2-Dimethylamino-1-methylethylamino)-propyl]-6-(3,4-dimethylphenyl)-pyrimidine-2-carbonitrile di-hydrochloride ¹H NMR (CD₃OD): δ 8.13 (s, 1H), 8.02 (s, 1H), 7.95 (d, 1H), 7.31 (d, 1H), 3.95-3.80 (m, 1H), 3.65-3.48 (m, 1H), 3.25-3.15 (m, 2H), 3.11-3.04 (m, 2H), 2.98 (s, 6H), 2.37 (s, 3H), 2.35 (s, 3H), 2.32-2.26 (m, 2H), 1.50 (d, 3H). MS m/z 352.5 (M+1)

13d: 4-(3,4-Dimethylphenyl)-6-[3-(1-ethylpyrrolidin-2-methylamino)-propyl]-pyrimidine-2-carbonitrile di-hydrochloride ¹H NMR (CD₃OD): δ 8.13 (s, 1H), 8.02 (s, 1H), 7.95 (d, 1H), 7.32 (d, 1H), 3.87-3.69 (m, 2H), 3.68-3.50 (m, 2H), 3.50-3.38 (m, 1H), 3.27-3.21 (m, 2H), 3.21-3.11 (m, 1H), 3.13 (t, 2H), 2.52-2.41 (m, 1H), 2.38 (s, 3H), 2.35 (s, 3H), 2.35-2.26 (m, 2H), 2.24-2.10 (m, 2H), 2.09-1.97 (m, 1H), 1.41 (t, 3H). MS m/z 378.5 (M+1)

13e: (S)-4-(3,4-Dimethylphenyl)-6-[3-(quinuclidinyl-3-amino)-propyl]-pyrimidine-2-carbonitrile Hydrochloride ¹H NMR (CD₃OD): δ 8.13 (s, 1H), 8.02 (s, 1H), 7.95 (d, 1H), 7.31 (d, 1H), 3.94-3.85 (m, 1H), 3.85 (t, 1H), 3.67-3.53 (m, 3H), 3.46-3.31 (m, 2H), 3.22 (t, 2H), 3.07 (t, 2H), 2.57 (brs, 1H), 2.38 (s, 3H), 2.35 (s, 3H), 2.36-2.26 (m, 3H), 2.22-2.10 (m, 1H), 2.10-1.99 (m, 2H). MS m/z 376.4 (M+1)

13f: 4-(3,4-Dimethylphenyl)-6-[3-(prop-2-yl-amino)-propyl]-pyrimidine-2-carbonitrile ¹H NMR (CDCl₃): δ 7.90 (s, 1H), 7.82 (d, 1H), 7.69 (s, 1H), 7.28 (d, 1H), 2.91 (t, 2H), 2.84-2.77 (m, 1H), 2.68 (t, 2H), 2.37 (s, 3H), 2.35 (s, 3H), 2.02-1.93 (m, 2H), 1.06 (d, 3H). MS m/z 309.4 (M+1)

13g: 4-(3,4-Dimethylphenyl)-6-[3-(1-methyl-trifluoroethylamino)-propyl]-pyrimidine-2-carbonitrile hydrochloride ¹H NMR (CD₃OD): δ 8.10 (s, 1H), 8.01 (s, 1H), 7.94 (d, 1H), 7.32 (d, 1H), 4.32-4.21 (m, 1H), 3.39-3.33 (m, 2H), 3.05 (t, 2H), 2.38 (s, 3H), 2.36 (s, 3H), 2.35-2.17 (m, 2H), 1.57 (d, 6H). MS m/z 363.1 (M+1)

13h: 4-(3,4-Dimethylphenyl)-6-{3-[2-(morpholin-4-yl)-ethylamino]-propyl}-pyrimidine-2-carbonitrile di-hydrochloride ¹H NMR (CD₃OD): δ 8.06 (s, 1H), 8.00 (s, 1H), 7.92 (d, 1H), 7.32 (d, 1H), 3.69 (t, 4H), 2.93 (t, 2H), 2.75 (t, 2H), 2.70 (t, 2H), 2.52 (t, 2H), 2.50-2.45 (m, 4H), 2.38 (s, 3H), 2.35 (s, 3H), 2.06-1.98 (m, 2H). MS m/z 380.4 (M+1)

13i: 4-{[3-(3-Diethylcarbamoyl)-piperidin-1-yl]-propyl}-6-(3,4-dimethylphenyl)-pyrimidin-2-carbonitrile Hydrochloride ¹H NMR (CD₃OD): δ 8.11 (s, 1H), 8.01 (s, 1H), 7.94 (d, 1H), 7.31 (d, 1H), 3.9-2.9 (m, 13H), 2.38 (s, 3H), 2.35 (s, 3H), 2.33 (m, 2H), 2.1-1.6 (m, 4H), 1.27-1.05 (m, 6H). MS m/z 434.4 (M+1).

13j: 4-(3,4-Dimethylphenyl)-6-[3-(4-pyridin-2-yl-piperazin-1-yl)-propyl]-pyrimidin-2-carbonitrile di-hydrochloride ¹H NMR (CD₃OD): δ 8.14 (d, d 1H), 8.12 (s, 1H), 8.10 (d, 1H), 8.02 (s, 1H), 7.95 (d, 1H), 7.46 (d, 1H), 7.32 (d, 1H), 7.14

(t, 1H), 4.42 (brs, 2H), 3.80 (brs, 4H), 3.38 (d, d 2H), 3.35 (brs, 2H), 3.07 (t, 2H), 2.40 (m, 2H), 2.38 (s, 3H), 2.36 (s, 3H). MS m/z 413.3 (M+1

EXAMPLE 14a 4-(3,4-Dimethyl-phenyl)-6-[3-(2-hydroxy-1,1-dimethyl-ethylamino)-propyl]-pyrimidine-2-carbonitrile Trifluoroacetic Acid Salt To a stirring solution of 4-(3-oxo-propyl)-6-(3,4-dimethylphenyl)-pyrimidine-2-carbonitrile (50 mg) in Acetonitrile (1.5 ml) was added 2-amino-2-methyl-1-propanol (36 µl), macroporous cyanoborohydride (110 mg, 2.57 mmol/g) and acetic acid (16 µl), and the resulting suspension was stirred at room temperature for 16 hrs. Reaction mixture was filtered and purified by preparative-HPLC to give 4-(3,4-dimethyl-phenyl)-6-[3-(2-hydroxy-1,1-dimethyl-ethylamino)-propyl]-pyrimidine-2-carbonitrile trifluoroacetic acid salt as a white solid (10 mg).

$^1$H NMR (MeOD): δ 8.08 (s, 1H), 8.00 (s, 1H), 7.92 (d, 1H), 7.33 (d, 1H), 3.55 (s, 1H), 3.11 (t, 2H), 3.02 (t, 2H), 2.38 (s, 1H), 2.36 (s, 1H), 2.16-2.25 (m, 2H), 1.34 (s, 6H). MS m/z 339.1 (M+1), 100%.

14b: 4-(3,4-Dimethyl-phenyl)-6-[3,(2-methoxy-ethylamino)-propyl]-pyrimidine-2-carbonitrile Trifluoroacetic Acid Salt To a stirring solution of 4-(3-oxo-propyl)-6-(3,4-dimethylphenyl)-pyrimidine-2-carbonitrile (50 mg) in MeOH (1.5 ml) was added 2-methoxyethylamine (26 µl). Once in solution, macroporous cyanoborohydride (110 mg, 2.57 mmol/g) and acetic acid (16 µl) were added, and the resulting suspension was stirred at room temperature for 16 hrs. Reaction mixture was filtered and purified by preparative-LCMS to give 4-(3,4-di-methylphenyl)-6-[3, (2-methoxy-ethylamino)-propyl]-pyrimidine-2-carbonitrile trifluoroacetic acid salt as a white solid (8 mg).

$^1$H NMR (MeOD): δ 8.07 (s, 1H), 8.00 (s, 1H), 7.94 (d, 1H), 7.33 (d, 1H), 3.64 (t, 2H), 3.42 (s, 3H), 3.24 (t, 2H), 3.13 (t, 3H), 3.01 (t, 2H), 2.38 (s, 3H), 2.36 (s, 3H), 2.16-2.26 (m, 2H). MS m/z 325.5 (M+1), 100%.

The procedure described above was further applied, using the appropriate amine derivatives, to prepare the following compounds:

14c: 4-(3,4-Dimethyl-phenyl)-6-{3-[(pyridin-2-ylmethyl)-amino]-propyl}-pyrimidine-2-carbonitrile Trifluoroacetic Acid Salt $^1$H NMR (CDCl$_3$): δ 8.62 (d, 1H), 7.98 (t, 1H), 7.90 (s, 1H), 7.84 (d, 1H), 7.75 (s, 1H), 7.60 (d, 1H), 7.52 (m, 1H), 7.27 (d, 1H), 4.48 (s, 2H), 3.33 (t, 2H), 3.07 (t, 2H), 2.36 (s, 3H), 2.35 (s, 3H), 2.23-2.35 (m, 2H). MS m/z 358.0 (M+1), 100%.

14d: 4-(3,4-Dimethyl-phenyl)-6-{3-[3-(1H-imidazol-4-yl)-propylamino]-propyl}-pyrimidine-2-carbonitrile Trifluoroacetic Acid Salt $^1$H NMR (MeOD): δ 8.81 (s, 1H), 8.08 (s, 1H), 8.00 (s, 1H), 7.93 (d, 1H), 7.45 (s, 1H), 7.30 (d, 1H), 3.39 (t, 2H), 3.18-3.22 (m, 4H), 3.04 (t, 2H), 2.38 (s, 3H), 2.36 (s, 3H), 2.20-2.28 (m, 2H). MS m/z 361.0 (M+1), 100%.

14e: 4-[3-(Bicyclo[2.2.1]hept-2-ylamino)-propyl]-6-(3,4-dimethyl-phenyl)-pyrimidine-2-carbonitrile Trifluoroacetic Acid Salt $^1$H NMR (CDCl$_3$): δ 7.87 (s, 1H), 7.82 (d, 1H), 7.70 (s, 1H), 7.52 (m, 1H), 3.37-3.42 (m, 1H), 3.01-3.09 (m, 2H), 2.96 (t, 2H), 2.54 (s, 1H), 2.35 (s, 3H), 2.33 (s, 3H), 2.22-2.30 (m, 3H), 1.93-2.04 (m, 1H), 1.68-1.78 (m, 1H), 1.53-1.60 (m, 2H), 1.38-1.45 (m, 3H), 1.26 (d, 1H). MS m/z 361.0 (M+1), 100%.

14f: 4-(3,4-Dimethyl-phenyl)-6-{3-[3-(2-oxo-pyrrolidin-1-yl)-propylamino]-propyl}-pyrimidine-2-carbonitrile Trifluoroacetic Acid Salt $^1$H NMR (CDCl$_3$): δ 7.91 (s, 1H), 7.84 (d, 1H), 7.81 (s, 1H), 7.27 (d, 1H), 3.47-3.50 (m, 4H), 3.12 (m, 2H), 3.05 (t, 2H), 2.98 (m, 2H), 2.49 (t, 2H), 2.36 (s, 3H), 2.34 (s, 3H), 2.29 (m, 2H), 2.08-2.16 (m, 4H). MS m/z 392.3 (M+1), 100%.

14g: 4-[3-(1,1-Dimethyl-2-morpholin-4-yl-ethylamino)-propyl]-6-(3,4-dimethyl-phenyl)-pyrimidine-2-carbonitrile Trifluoroacetic Acid Salt $^1$H NMR (CDCl$_3$): δ 7.91 (s, 1H), 7.86 (d, 1H), 7.78 (s, 1H), 7.27 (d, 1H), 3.92 (m, 4H), 3.34 (s, 2H), 3.14-3.18 (m, 6H), 3.01 (t, 2H), 2.37 (s, 3H), 2.35 (s, 3H), 2.30-2.35 (m, 2H), 1.52 (s, 6H). MS m/z 408.1 (M+1), 100%.

14h 4-(3,4-Dimethyl-phenyl)-6-{3-[2-(1H-indol-3-yl)-ethylamino]-propyl}-pyrimidine-2-carbonitrile Trifluoroacetic Acid Salt $^1$H NMR (MeOD): δ 8.03 (s, 1H), 7.99 (s, 1H), 7.93 (d, 1H), 7.58 (d, 1H), 7.31-7.37 (m, 2H), 7.19 (s, 1H), 7.12 (t, 1H), 7.04 (t, 1H), 3.33-3.38 (m, 2H), 3.14-3.21 (m, 4H), 2.99 (t, 2H), 2.38 (s, 3H), 2.35 (s, 3H), 2.14-2.21 (m, 2H). MS m/z 411.0 (M+1), 100%.

14i: 4-(3,4-Dimethyl-phenyl)-6-[3-(methylcaramoyl-methyl-amino)-propyl]-pyrimidine-2-carbonitrile Trifluoroacetic Acid Salt $^1$H NMR (MeOD): δ 8.07 (s, 1H), 8.00 (s, 1H), 7.94 (d, 1H), 7.31 (d, 1H), 3.73 (s, 1H), 3.08 (t, 2H), 3.01 (t, 2H), 2.79 (s, 3H), 2.38 (s, 3H), 2.36 (s, 3H), 2.19 (t, 2H). MS m/z 338.5 (M+1), 100%.

14j: 4-[3-(2-Acetylamino-ethylamino)-propyl]-6-(3,4-dimethyl-phenyl)-pyrimidine-2-carbonitrile Trifluoroacetic Acid Salt $^1$H NMR (MeOD): δ 8.08 (s, 1H), 8.00 (s, 1H), 7.94 (d, 1H), 7.31 (d, 1H), 3.50 (t, 2H), 3.15 (m, 4H), 3.01 (t, 2H), 2.38 (s, 3H), 2.35 (s, 3H), 2.21 (m, 2H), 1.99 (s, 3H). MS m/z 352.4 (M+1), 100%.

14k: 4-(3,4-Dimethyl-phenyl)-6-{3-[2-(1-methyl-pyrrolidin-2-yl)-ethylamino]-propyl}-pyrimidine-2-carbonitrile Trifluoroacetic Acid Salt $^1$H NMR (MeOD): δ 8.08 (s, 1H), 8.00 (s, 1H), 7.94 (d, 1H), 7.33 (d, 1H), 3.70-3.77 (m, 1H), 3.33-3.41 (m, 1H), 3.12-3.21 (m, 5H), 3.04 (t, 2H), 2.94 (s, 3H), 2.38-2.43 (m, 2H), 2.38 (s, 3H), 2.36 (s, 3H), 2.20-2.28 (m, 2H), 2.04-2.18 (m, 2H), 1.93-2.04 (m, 1H), 1.75-1.86 (m, 1H). MS m/z 378.5 (M+1), 100%.

14l: 4-[3-(Carbamoylmethyl-methyl-amino)-propyl]-6-(3,4-dimethyl-phenyl)-pyrimidine-2-carbonitrile Trifluoroacetic Acid Salt $^1$H NMR (MeOD): δ 8.08 (s, 1H), 8.00 (s, 1H), 7.94 (d, 1H), 7.32 (d, 1H), 4.00 (br s, 2H), 3.24-3.30 (m, 2H), 3.01 (t, 2H), 2.98 (t, 2H), 2.38 (s, 3H), 2.36 (s, 3H), 2.23-2.30 (m, 2H). MS m/z 338.4 (M+1), 100%.

14m: 4-[3-(Dimethylcarbamoylmethyl-amino)-propyl]-6-(3,4-dimethyl-phenyl)-pyrimidine-2-carbonitrile Trifluoroacetic Acid Salt $^1$H NMR (CDCl$_3$): δ 7.89 (s, 1H), 7.83 (d, 1H), 7.76 (s, 1H), 7.27 (d, 1H), 4.00 (s, 2H), 3.24 (t, 2H), 3.03 (m, 2H), 3.01 (s, 6H), 2.36 (s, 3H), 2.34 (s, 3H), 2.23-2.35 (m, 2H). MS m/z 352.3 (M+1), 100%.

14n: 4-(3,4-Dimethyl-phenyl)-6-{3-[2-(2-oxo-imidazolidin-1-yl)-ethylamino]-propyl}-pyrimidine-2-carbonitrile Trifluoroacetic Acid Salt $^1$H NMR (MeOD): δ 8.08 (s, 1H), 8.00 (s, 1H), 7.94 (d, 1H), 7.33 (d, 1H), 3.51-3.55 (m, 2H), 3.43-3.48 (m, 4H), 3.23 (t, 2H), 3.17 (t, 2H), 3.02 (t, 2H), 2.38 (s, 3H), 2.36 (s, 3H), 2.17-2.27 (m, 2H). MS m/z 379.4 (M+1), 100%.

14o: 4-[3-(3-Dimethylamino-propylamino)-propyl]-6-(3,4-dimethyl-phenyl)-pyrimidine-2-carbonitrile Trifluoroacetic Acid Salt $^1$H NMR (MeOD): δ 8.07 (s, 1H), 7.99 (s, 1H), 7.93 (d, 1H), 7.31 (d, 1H), 3.24 (t, 2H), 3.13-3.20 (m, 4H), 3.03 (t, 2H), 2.92 (s, 6H), 2.37 (s, 3H), 2.35 (s, 3H), 2.20-2.28 (m, 2H), 2.12-2.19 (m, 2H). MS m/z 352.4 (M+1), 100%.

EXAMPLE 15

4-(3-Hydroxy-3-oxopropyl)-6-(3-trifluoromethyl phenyl)-pyrimidine-2-carbonitrile To a stirred solution of 4-(3-hydroxypropyl)-6-(3-trifluoromethylphenyl)-pyrimidine-2-carbonitrile (1.54 g) in acetonitrile (15 mL) was added 0.2M KH$_2$PO$_4$ pH 6.5 buffer (15 mL), followed by TEMPO (120 mg). The mixture was heated to 45° C. and solutions of NaClO$_2$ (1.26 g in 5 mL H$_2$O) and 5% NaOCl (0.25 mL in 5 mL H$_2$O) added concomitantly over 1 h (approx. 1.5 mL of each added as initial aliquots). After 5 h the mixture was cooled and basified to pH~9.0 by the addition of 4N NaOH, followed by addition of cold sodium sulfite solution. Neutrals were removed by extraction with ethyl acetate. The aqueous phase was acidified to pH~3.5 by addition of 5N HCl and extracted twice with DCM (material insoluble in the bi-phasic mixture was removed by filtration through celite) and the organic layer washed with water then brine. Removal of solvent followed by trituration with ether gave a white precipitate containing TEMPO residues and some 2-carboxamide-pyrimide derivative as by-product. The resulting mother liquors contained the required acid, 4-(3-hydroxy-3-oxopropyl)-6-(3-trifluoromethylphenyl)-pyrimidine-2-carbonitrile, 370 mg.

$^1$H NMR (CDCl$_3$): δ 8.35 (s, 1H), 8.31 (d, 1H), 7.83 (s, 1H), 7.83 (d, 1H), 7.68 (t, 1H), 3.22 (t, 2H), 3.00 (t, 2H) MS m/z 322.1 (M+1)

EXAMPLE 16a

4-[3-(Piperidin-1-yl)-3-oxopropyl]-6-(3-trifluoromethylphenyl)-pyrimidine-2-carbonitrile To a solution of 4-(3-hydroxy-3-oxopropyl)-6-(3-trifluoromethylphenyl)-pyrimidine-2-carbonitrile (64 mg) in DCM (6 mL) was added 1-hydroxybenzotriazole (30 mg) and 1-(3-dimethylaminopropyl)-3-ethyl carbodiimide HCl (38 mg). The solution was stirred at room temperature for 15 min and piperidine (22 mg) added. After standing for 18 h, the reaction mixture was washed with HCl (1M, 2×5 ml), H$_2$O then brine and dried with sodium sulfate. After removal of solvent, crystallisation from a trace of acetone/ether gave 4-(3-piperidin-1-yl-3-oxopropyl)-6-(3-trifluoromethylphenyl)-pyrimidine-2-carbonitrile as a white solid, 35 mg.

$^1$H NMR (CDCl$_3$): δ 8.37 (s, 1H), 8.31 (d, 1H), 7.91 (s, 1H), 7.80 (d, 1H), 7.66 (t, 1H), 3.51 (t, 2H), 3.46 (t, 2H), 3.23 (t, 2H), 2.95 (t, 2H), 1.70-1.58 (m, 4H), 1.56-1.48 (m, 2H). MS m/z 389.1 (M+1)

The following compounds were prepared in a similar manner by coupling the acid with the appropriate amine in the presence of HOBt and EDCI.

16b: 4-[3-(Homopiperazin-1-yl)-3-oxopropyl]-6-(3-trifluoromethylphenyl)-pyrimidine-2-carbonitrile Hydrochloride $^1$H NMR (CD$_3$OD): δ 8.51 (s, 1H), 8.48 (d, 1H), 8.28 (s, 1H), 7.90 (d, 1H), 7.78 (t, 1H), 3.98-3.92 and 3.84-3.78 (m, 2H) (rotamers), 3.81-3.76 and 3.71-3.66 (m, 2H) (rotamers), 3.50-3.45 and 3.33-3.27 (m, 2H) (rotamers), 3.41-3.35 and 3.33-3.27 (m, 2H) (rotamers), 3.29-3.23 (m, 2H), 3.07 (t, 2H), 2.26-2.16 and 2.10-2.02 (m, 2H) (rotamers). MS m/z 404.4 (M+1)

16c: 4-(3,4-Dimethyl-phenyl)-6-[2-(2-pyridin-2-yl-ethylcarbamoyl)-ethyl]-pyrimidine-2-carbonitrile Trifluoromethanesulfonte Salt $^1$H NMR (CDCl$_3$): δ 8.62 (d, 1H), 8.27 (t, 1H), 7.88 (s, 1H), 7.81 (d, 1H), 7.62-7.78 (m, 4H), 7.28 (s, 1H), 3.70-3.80 (m, 2H), 3.33 (t, 2H), 3.04 (t, 2H), 2.70 (t, 2H), 2.34 (d, 6H). MS m/z 386.0 (M+1), 95%.

16d: 4-(3,4-Dimethyl-phenyl)-6-[2-(2-piperidin-1-yl-ethylcarbamoyl)-ethyl]-pyrimidine-2-carbonitrile $^1$H NMR (CDCl$_3$): δ 7.90 (s, 1H), 7.85 (d, 1H), 7.78 (s, 1H), 7.28 (s, 1H), 3.29 (t, 2H), 3.19 (t, 2H), 2.75 (t, 2H), 2.30-2.40 (m, 12H), 1.52-1.60 (m, 4H), 1.41-1.47 (m, 2H). MS m/z 392.1 (M+1), 100%.

EXAMPLE 17

4-(3-tert-Butyl-Phenyl)-6-(3-oxo-propyl)-pyrimidine-2-carbonitrile

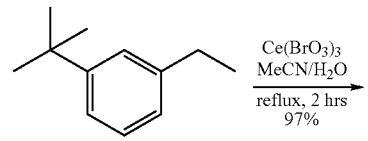

-continued

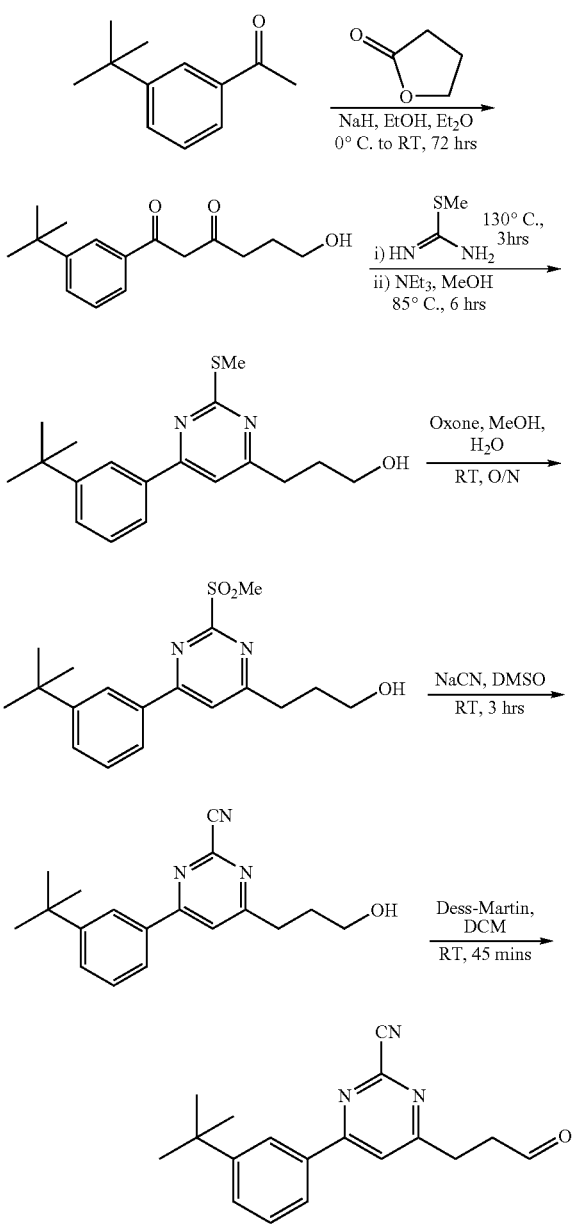

A: 1-(3-tert-Butyl-phenyl)-ethanone

To a stirring solution of 1-tert-butyl-3-ethylbenzene (11.15) in acetonitrile (350 ml) and water (150 ml) at room temperature was added cerium (III) sulfate (6.05 g) and barium bromate (13.5 g). The resulting suspension was heated at reflux for 16 hrs. After cooling to room temperature, the reaction mixture was filtered. Saturated aqueous sodium thiosulphate solution was added to the filtrate, and the product was extracted into DCM (3×100 ml). Combined organics were washed with brine, dried over MgSO$_4$ and concentrated in vacuo to give 1-(3-tert-butyl-phenyl)-ethanone as a yellow oil crude product (13.5 g). $^1$H NMR (CDCl$_3$): δ 8.00 (s, 1H), 7.75 (d, 1H), 7.61 (d, 1H), 7.39 (t, 1H), 2.61 (s, 3H), 1.36 (s, 9H).

B: 1,3-Dioxo-6-hydroxy-1-(3'-tert-Butyl-phenyl)-hexane

To a stirring suspension of NaH (60% in oil, 7.66 g) in ether (480 ml) at 0° C. was added ethanol (479 μL), followed by γ-butyrolactone (6.18 ml). This was followed by dropwise addition of 1-(3-tert-butyl-phenyl)-ethanone (13.5 g) in ether (80 ml). The resulting mixture was allowed to warm to room temperature and stirred for 72 hours. After careful addition of ethanol (10.5 ml), ammonium chloride solution (10 g in 250 ml water) was then added, ether layer was then separated and washed with brine (300 ml), dried over MgSO$_4$ and concentrated in vacuo to give 1,3-dioxo-6-hydroxy-1(3'-tert-butyl-phenyl)-hexane as crude product (18.5 g). This required no purification and was immediately used in the next reaction.
MS m/z 245.4 (M+1), 80%.

C: 2-Methylsulfanyl-4-(3-hydroxypropyl)-6-(3-tert-butyl-methyl-phenyl)-pyrimidine 1,3-Dioxo-6-hydroxy-1(3'-tert-butyl-phenyl)-hexane (crude product, 18.5 g) and S-methylisothiouranium salt (30.7 g) were heated at 110° C. for 3 hours. The reaction mixture was then allowed to cool to room temperature, methanol (30 ml) and triethylamine (26 ml) were added, and the resulting mixture was heated at 85° C. for 4 hours. The reaction mixture was concentrated in vacuo, and the product was taken into ethyl acetate (400 ml) then washed with water (2×200 ml) and organic layer dried over MgSO$_4$. After removal of solvent under vacuum, the residue was columned on silica gel using petrol and ethyl acetate (1:1) as eluant to give of 2-methylsulfanyl-4-(3-hydroxypropyl)-6-(3-tert-butyl-methyl-phenyl)-pyrimidine (5.2 g) as an oil.
$^1$H NMR (CDCl$_3$): δ 8.12 (s, 1H), 7.86 (d, 1H), 7.52 (d, 1H), 7.40 (t, 1H), 7.25 (s, 1H), 3.75 (t, 2H), 2.88 (t, 2H), 2.64 (s, 3H), 1.99-2.06 (m, 2H), 1.38 (s, 9H). MS m/z 317.1 (M+1), 95%.

D: 2-Methylsulphonyl-4-(3-hydroxypropyl)-6-(3-trifluoromethylphenyl)-pyrimidine

To the solution of 2-methylsulfanyl-4-(3-hydroxypropyl)-6-(3-tert-butyl-phenyl)-pyrimidine (5.2 g) in a mixed solvent of methanol and water (122 ml, 10:1) was added OXONE (23.2 g). The mixture was stirred at room temperature overnight. After diluting with water (200 ml), then product was extracted into ethyl acetate (3×200 ml). Combined organics were washed with brine (200 ml), dried over MgSO$_4$ and concentrated in vacuo to generate of 2-methylsulphonyl-4-(3-hydroxypropyl)-6-(3-tert-butyl-methyl-phenyl)-pyrimidine (4.6 g) as a pale brown solid. This was used as crude in the next step without further purification.
$^1$H NMR (CDCl$_3$): δ 8.12 (s, 1H), 7.92 (d, 1H), 7.73 (s, 1H), 7.59 (d, 1H), 7.45 (t, 1H), 3.75 (t, 2H), 3.43 (s, 3H), 3.08 (t, 2H), 2.08-2.16 (m, 2H), 1.40 (s, 9H). MS m/z 349.4 (M+1), 95%.

E: 4-(3-tert-Butyl-phenyl)-6-(3-hydroxy-propyl)-pyrimidine-2-carbonitrile

To a stirring solution of 2-methylsulphonyl-4-(3-hydroxypropyl)-6-(3-tert-butyl-methyl-phenyl)-pyrimidine (4.6 g) in DMSO (120 ml) at room temperature was added sodium cyanide (647 mg). The resulting suspension was stirred at room temperature for 3 hours. After adding ethyl acetate (200 ml), the mixture was then washed with water (100 ml×3). Organic layer was dried over MgSO$_4$ and concentrated in vacuo, the residue was columned on silica gel using Petrol and EtOAc as eluent to give 4-(3-tert-butyl-phenyl)-6-(3-hydroxy-propyl)-pyrimidine-2-carbonitrile (4.0 g) as an oil.

$^1$H NMR (CDCl$_3$): δ 8.14 (s, 1H), 7.89 (d, 1H), 7.74 (s, 1H), 7.60 (d, 1H), 7.46 (t, 1H), 3.76 (t, 2H), 3.00 (t, 2H), 2.05-2.13 (m, 2H), 1.40 (s, 9H). MS m/z 296.0 (M+1), 95%.

F: 4-(3-tert-Butyl-phenyl)-6-(3-oxo-propyl)-pyrimidine-2-carbonitrile

Dess-Martin periodinane (679 mg) was added to a solution of 4-(3-tert-butyl-phenyl)-6-(3-hydroxy-propyl)-pyrimidine carbonitrile (394 mg) in DCM (5 ml) and the resulting suspension was stirred at room temperature for 45 mins. Reaction mixture was diluted with EtOAc (100 ml) then washed with water (2×100 ml). Organic layer was dried over MgSO$_4$ and concentrated in vacuo. The residue was columned on silica gel using petrol and ethyl acetate (1:1) as eluent to generate 4-(3-tert-butyl-phenyl)-6-(3-oxo-propyl)-pyrimidine-2-carbonitrile as a pale yellow solid (266 mg).

$^1$H NMR (CDCl$_3$): δ 8.13 (s, 1H), 7.88 (d, 1H), 7.79 (s, 1H), 7.60 (d, 1H), 7.46 (t, 1H), 3.18 (m, 2H), 3.11 (m, 2H), 1.40 (s, 9H). MS m/z 294.0 (M+1), 95%.

EXAMPLE 18a 4-(3-Benzyloxy-propyl)-6-(3-trifluoromethyl-phenyl)-pyrimidine-2-carbonitrile A: 6-Benzyloxy-3-oxo-hexanoic Acid Ethyl Ester 4-Benzyloxybutyric acid (6.38 mL), Meldrum's acid (5.76 g) and dimethylaminopyridine (9.77 g) were dissolved in DCM (200 mL) and cooled to 0° C. A solution of isopropenyl chloroformate in dichloromethane (100 mL) was added dropwise and stirring at 0° C. continued for a further 2 h. Potassium hydrogen sulphate (200 mL of a 10% aqueous solution) was then added, the organic phase separated, dried over sodium sulphate, and evaporated under reduced pressure. The residue was dissolved in ethanol (200 mL) and heated at reflux overnight. Following cooling, the solvent was evaporated under reduced pressure and the resultant oil was purified by flash silica column chromatography. 6-Benzyloxy-3-oxo-hexanoic acid ethyl ester was isolated as an orange oil (8.53 g).

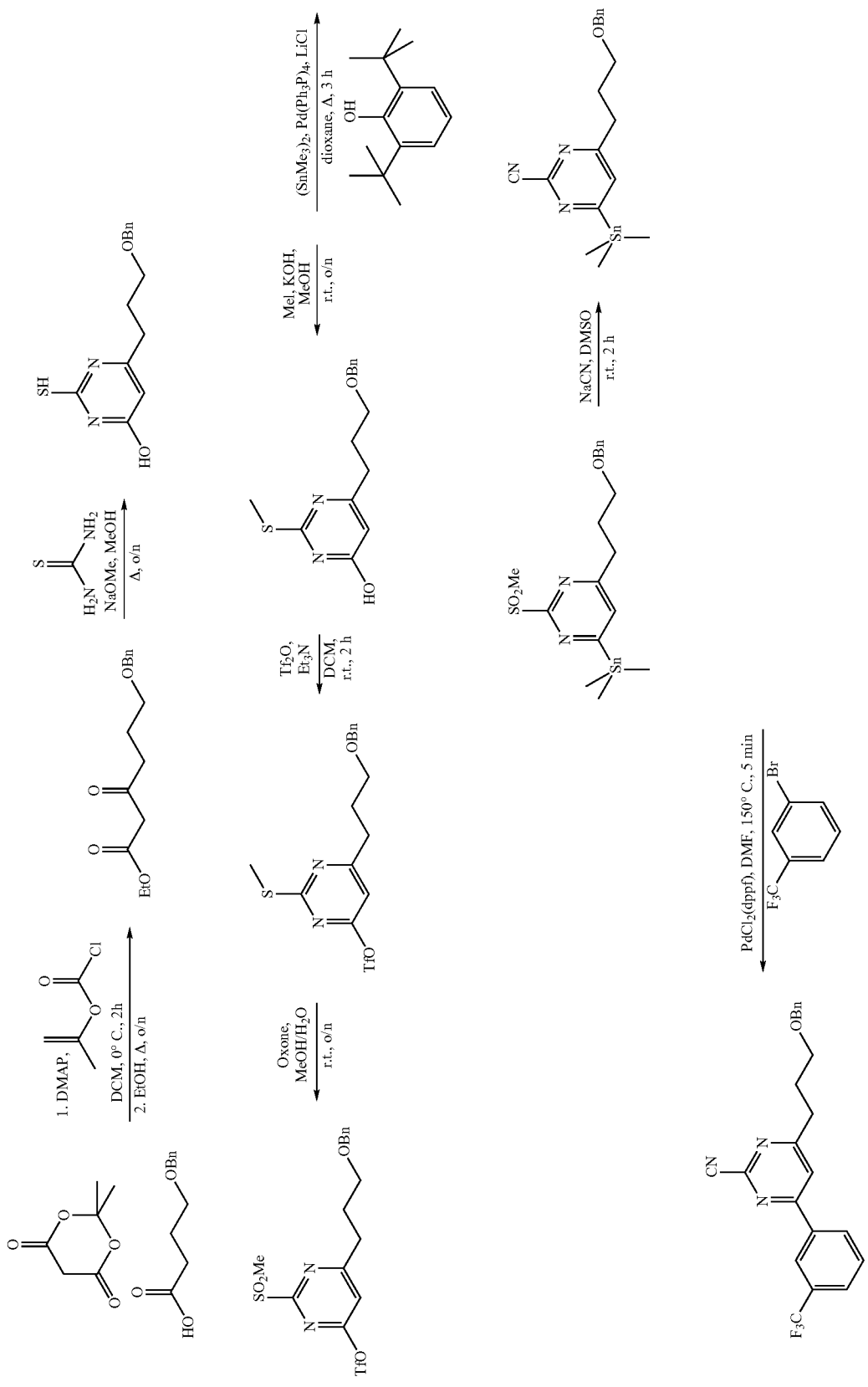

¹H NMR (CDCl₃): δ 7.26-7.35 (m, 5H), 4.48 (s, 2H), 4.18 (q, 2H), 3.49 (t, 2H), 3.44 (s, 2H), 2.67 (t, 2H), 1.90-1.97 (m, 2H), 1.27 (t, 3H). MS m/z 287.0 (M+1), 100%.

B: 6-(3-Benzyloxy-propyl)-2-mercapto-pyrimidin-4-ol

To a stirred suspension of sodium methoxide (3.48 g) in methanol (40 mL), cooled to 0° C., was added thiourea (3.56 g). The mixture was stirred until it dissolved, then 6-benzyloxy-3-oxo-hexanoic acid ethyl ester (8.52 g in 20 mL methanol) was added slowly. The solution was heated at reflux overnight, cooled to room temperature, and concentrated under vacuum. The residue was dissolved in water (50 mL), acidified to pH 6 with acetic acid, and stirred for 1 h. The precipitate was filtered, washed successively with water (2×20 mL) and isopropanol (2×20 mL), then dried to afford 6-(3-benzyloxy-propyl)-2-mercapto-pyrimidin-4-ol as a white powder (7.94 g). MS m/z 277.1 (M+1), 100%.

C: 6-(3-Benzyloxy-propyl)-2-methylsulfanyl-pyrimidin-4-ol

A mixture of 6-(3-benzyloxy-propyl)-2-mercapto-pyrimidin-4-ol (7.94 g), potassium hydroxide (32 mL of 1N solution in methanol) and methyl iodide (1.97 mL) was stirred at room temperature overnight. The precipitate was filtered, washed successively with methanol (2×20 mL), isopropanol (2×20 mL) and water (2×20 mL), then dried to afford 6-(3-benzyloxy-propyl)-2-methylsulfanyl-pyrimidin-4-ol as a white powder (7.0 g). MS m/z 291.0 (M+1), 100%.

D: Trifluoro-acetic acid 6-(3-benzyloxy-propyl)-2-methylsulfanyl-pyrimidin-4-yl Ester A solution of 6-(3-benzyloxy-propyl)-2-methylsulfanyl-pyrimidin-4-ol (200 mg) and triethylamine (0.2 mL) in dichloromethane (5 mL) was cooled to 0° C., whereupon trifluoroacetic anhydride (0.14 mL) was added and the resultant mixture warmed to room temperature. After 2 h, the reaction mixture was washed with water (2×20 mL), dried over sodium sulphate and evaporated under reduced pressure. Flash silica column chromatography afforded trifluoro-acetic acid 6-(3-benzyloxy-propyl)-2-methylsulfanyl-pyrimidin-4-yl ester (160 mg) as a yellow oil.

¹H NMR (CDCl₃): δ 7.30-7.40 (m, 5H), 6.58 (m, 1H), 4.49 (s, 2H), 3.51 (t, 2H), 2.88 (t, 2H), 2.54 (s, 3H), 2.04-2.10 (m, 2H).

E: Trifluoro-acetic acid 6-(3-benzyloxy-propyl)-2-methanesulfonyl-pyrimidin-4-yl Ester A suspension of trifluoro-acetic acid 6-(3-benzyloxy-propyl)-2-methylsulfanyl-pyrimidin-4-yl ester (494 mg) and Oxone (419 mg) in methanol/water (8/2 mL) was stirred at room temperature overnight. Methanol was evaporated under reduced pressure, and the resultant suspension was extracted with ethyl acetate (2×20 mL). The organic fraction was dried over sodium sulphate and evaporated under reduced pressure to afford trifluoro-acetic acid 6-(3-benzyloxy-propyl)-2-methanesulfonyl-pyrimidin-4-yl ester (135 mg).

¹H NMR (CDCl₃): δ 7.28-7.40 (m, 5H), 7.15 (m, 1H), 4.47 (s, 2H), 3.54 (t, 2H), 3.33 (s, 3H), 3.11 (t, 2H), 2.10-2.18 (m, 2H). MS m/z 477.0 (M+1), 100%.

F: 4-(3-Benzyloxy-propyl)-2-methanesulfonyl-6-trimethylstannanyl-pyrimidine

A mixture of trifluoro-acetic acid 6-(3-benzyloxy-propyl)-2-methanesulfonyl-pyrimidin-4-yl ester (13.5 g), hexamethylditin (11.8 g), tetrakis(triphenylphosphine)-palladium(0) (1.4 g), lithium chloride (1.4 g), and 2-6-di-tert-butylphenol (150 mg) in dioxane (100 mL) was heated to reflux under N₂ for 3 h. Upon cooling, the suspension was filtered and the filtrate evaporated to dryness under reduced pressure. Flash silica chromatography afforded 4-(3-benzyloxy-propyl)-2-methanesulfonyl-6-trimethylstannanyl-pyrimidine (8.0 g) as a pale yellow oil.

¹H NMR (CDCl₃): δ 7.47 (s, 1H), 7.25-7.4 (m, 5H), 4.5 (s, 2H), 3.55 (t, 2H), 3.35 (s, 3H), 2.90 (t, 2H), 2.06 (m, 2H), 0.40 (s, 9H).

G: 4-(3-Benzyloxy-propyl)-6-trimethylstannanyl-pyrimidine-2-carbonitrile

A solution of 4-(3-benzyloxy-propyl)-2-methanesulfonyl-6-trimethylstannanyl-pyrimidine (200 mg) and sodium cyanide (42 mg) in dimethylsulfoxide (1 mL) was stirred at room temperature for 2 h. The reaction mixture was diluted with ethyl acetate (10 mL), washed with water (2×10 mL), dried over sodium sulphate and evaporated at reduced pressure. Flash silica chromatography afforded 4-(3-benzyl-oxy-propyl)-6-trimethylstannanyl-pyrimidine-2-carbonitrile as a yellow oil (111 mg).

¹H NMR (CDCl₃): δ 7.45 (s, 1H), 7.28-7.37 (m, 5H), 4.50 (s, 2H), 3.54 (t, 2H), 2.84 (t, 2H), 2.02-2.10 (m, 2H), 0.39 (s, 9H).

H: 4-(3-Benzyloxy-propyl)-6-(3-trifluoromethyl-phenyl)-pyrimidine-2-carbonitrile A solution of 4-(3-benzyloxy-propyl)-6-trimethylstannanyl-pyrimidine-2-carbonitrile (100 mg), trifluoromethylbromobenzene (36 μL) and 1,1'-(bistriphenylphosphino)ferrocenedichloropalladium(II) (16 mg) in dimethylformamide (5 mL) was heated in microwave at 150° C. for 5 min. The resulting suspension was diluted with ethyl acetate and water (20 mL), the organic layer being separated, dried over sodium sulphate and evaporated at reduced pressure. Flash silica chromatography afforded 4-(3-benzyloxy-propyl)-6-(3-trifluoromethyl-phenyl)-pyrimidine-2-carbonitrile as a yellow gum (47 mg).

¹H NMR (CDCl₃): δ 8.31 (s, 1H), 8.25 (d, 1H), 7.82 (d, 1H), 7.72 (s, 1H), 7.67 (t, 1H), 7.24-7.32 (m, 5H), 4.49 (s, 2H), 3.57 (t, 2H), 3.02 (t, 2H), 2.10-2.18 (m, 2H). MS m/z 398.1 (M+1), 100%.

The procedure described above was further applied, using the appropriate aryl bromide derivatives, to prepare the following compounds:

18b: 4-(3-Amino-5-trifluoromethyl-phenyl)-6-(3-benzyloxy-propyl)-pyrimidine-2-carbonitrile ¹H NMR (CDCl₃): δ 7.67 (s, 1H), 7.59 (s, 1H), 7.56 (s, 1H), 7.24-7.35 (m, 5H), 7.05 (s, 1H), 4.49 (s, 2H), 4.08 (br s, 2H), 3.56 (t, 2H), 3.00 (t, 2H), 2.10-2.18 (m, 2H). MS m/z 413.3 (M+1), 100%.

18c: 4-(3-Benzyloxy-propyl)-6-(3-carboxy-5-trifluoromethyl-phenyl)-pyrimidine-2-carbonitrile ¹H NMR (CDCl₃): δ 8.86 (s, 1H), 8.55 (s, 1H), 8.47 (s, 1H), 7.76 (s, 1H), 7.24-7.35 (m, 5H), 4.43 (s, 2H), 3.53 (t, 2H), 3.00 (t, 2H), 2.09-2.15 (m, 2H). MS m/z 440.3 (M-H), 100%.

EXAMPLE 19

4-(3-Benzyloxy-propyl)-6-(3-methanesulfonylamino-5-trifluoromethylphenyl)-pyrimidine-2-carbonitrile A: N-(3-Bromo-5-trifluoromethyl-phenyl)-methanesulfonamide To a solution of 3-Amino-5-bromobenzotrifluoride (200 mg) in pyridine (2 mL) was added methane sulphonyl chloride (115 mg) and one crystal of 4-(dimethyl-amino)pyridine. The mixture was stirred at room temperature for four hours then diluted with ethyl acetate (50 mL) and washed with HCl (2M, 50 mL) and saturated sodium chloride solution (50 mL). Organics were separated, dried over sodium sulphate, filtered, and solvent was removed under reduced pressure to yield N-(3-bromo-5-trifluoromethyl-phenyl)-methanesulfonamide (264 mg).

$^1$H NMR (MeOD): δ7.59 (s, 1H), 7.58 (s, 1H), 7.40 (s, 1H), 7.00 (s, 1H), 3.11 (s, 3H). MS m/z 318.9 (M+1).

B: 4-(3-Benzloxy-propyl)-6-(3-methanesulfonylamino-5-trifluoromethylphenyl)-pyrimidine-2-carbonitrile N-(3-Bromo-5-trifluoromethyl-phenyl)-methanesulfonamide (37 mg), 4-(3-benzyloxy-propyl)-6-trimethylstannanyl-pyrimidine-2-carbonitrile (40 mg) and dichlorobis(triphenylphosphine)palladium(II) (7 mg) in DMF (1 mL) were heated in a microwave to 180° C. for five minutes. The mixture was diluted with ethyl acetate (10 mL) and filtered through celite. The filtrate was washed with water (10 mL) and saturated sodium chloride solution (10 mL). Organics were separated, dried over sodium sulphate, filtered and solvent was removed under reduced pressure to yield crude product. Purification by HPLC afforded 4-(3-benzyloxy-propyl)-6-(3-methanesulfonylamino-5-trifluoromethylphenyl)-pyrimidine-2-carbonitrile.

$^1$H NMR (MeOD): δ 8.10 (s, 1H), 8.09 (s, 1H), 7.74 (s, 1H), 7.70 (5, 1H), 7.29 (m, 5H), 4.49 (s, 2H), 3.58 (t, 2H), 3.12 (s, 3H), 3.06 (t, 2H), 2.17 (m, 2H). MS m/z 491.1 (M+1) 100%.

EXAMPLE 20

4-(3-Benzyloxy-propyl)-6-(3-methylsulphamoyl-5-trifluoromethyl-phenyl)-pyrimidine-2-carbonitrile A: 3-Bromo-N-methyl-5-trifluoromethyl-benzenesulphonamide To a solution of 3-bromo-5-(trifluoromethyl)-benzene sulphonyl chloride (200 mg) in 1,4-dioxane (1 mL) was added methylamine (40% aqueous solution, 96 mg). The mixture was stirred at room temperature for three hours then diluted with ethyl acetate (20 mL) and washed with HCl (1M, 2×20 mL). Organics were separated, dried over sodium sulphate, filtered, and solvent was removed under reduced pressure to yield 3-bromo-N-methyl-5-trifluoromethyl-benzenesulphonamide (181 mg) as a yellow solid. $^1$H NMR (MeOD): δ 8.19 (s, 1H), 8.05 (s, 1H), 7.98 (s, 1H), 4.58 (m, 1H), 2.74 (d, 3H). MS m/z 319.8 (M+1).

B: 4-(3-Benzyloxy-propyl)-6-(3-methylsulphamoyl-5-trifluoromethyl-phenyl)pyrimidine-2-carbonitrile 3-Bromo-N-methyl-5-trifluoromethyl-benzenesulphonamide (37 mg), 4-(3-benzyloxy-propyl)-6-trimethylstannanyl-pyrimidine-2-carbonitrile (40 mg) and dichlorobis(triphenylphosphine)palladium(II) (7 mg) in DMF (1 mL) were heated in a microwave to 180° C. for five minutes. The mixture was diluted with ethyl acetate (20 mL) and washed with water (3×20 mL). Organics were separated, dried over sodium sulphate, filtered, and solvent was removed under reduced pressure to yield crude product. Purification by preparative-HPLC afforded 4-(3-benzyloxy-propyl)-6-(3-methylsulphamoyl-5-trifluoromethyl-phenyl)-pyrimidine-2-carbonitrile (16.5 mg).

$^1$H NMR (MeOD): δ 8.70 (s, 1H), 8.54 (s, 1H), 8.27 (s, 1H), 7.82 (s, 1H), 7.27 (m, 5H), 4.78 (m, 1H), 4.48 (s, 2H), 3.59 (t, 2H), 3.06 (t, 2H), 2.75 (d, 3H), 2.16 (m, 2H). MS m/z 491.1 (M+1) 100%.

EXAMPLE 21

4-(3-Hydroxy-propyl)-6-(3-methylsulphamoyl-5-trifluoromethyl-phenyl)-pyrimidine-2-carbonitrile To a solution of 4-(3-benzyloxy-propyl)-6-(3-methylsulphamoyl-5-trifluoromethyl-phenyl)-pyrimidine-2-carbonitrile (14.4 mg) in acetonitrile (700 μL) and water (300 μL) was added cerium sulphate (3 mg) and barium bromate (6 mg). The mixture was heated to reflux overnight then filtered through a sinter glass funnel, the residue washed with DCM (10 mL). The filtrate was washed with saturated sodium thiosulphate (10 mL) organics separated, dried over sodium sulphate, filtered, and solvent was removed under reduced pressure to yield crude product. Purification by preparative-HPLC afforded 4-(3-hydroxy-propyl)-6-(3-methylsulphamoyl-5-trifluoromethyl-phenyl)-pyrimidine-2-carbonitrile (3.2 mg).

$^1$H NMR (MeOD): δ 8.89 (s, 1H), 8.78 (s, 1H), 8.31 (s, 1H), 8.28 (s, 1H), 3.66 (t, 2H), 3.05 (t, 2H), 2.61 (s, 3H), 2.08 (m, 2H). MS m/z 401.1 (M+1) 100%.

EXAMPLE 22

4-(3-Dimethylsulfamoyl-5-trifluoromethyl-phenyl)-6-(3-piperidin-1-yl-propyl)-pyrimidine-2-carbonitrile

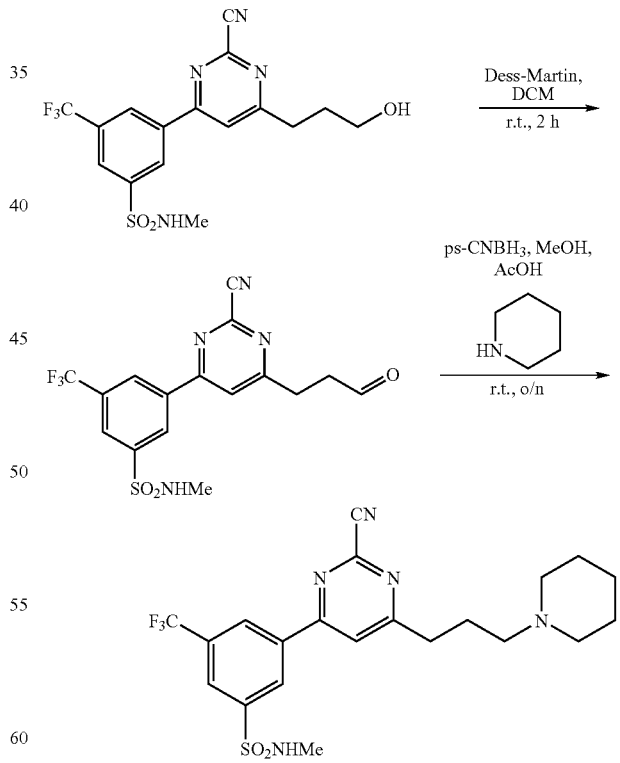

A: 4-(3-Methylsulfamoyl-5-trifluoromethyl-phenyl)-6-(3-oxo-propyl)-pyrimidine-2-carbonitrile A suspension of 4-(3-hydroxy-propyl)-6-(3-methylsulfamoyl-5-trifluoromethyl-phenyl)-pyrimidine-2-carbonitrile (235 mg) and Dess Martin reagent (299 mg) in dichloromethane (5 mL) was stirred at room temperature for 2 h. The reaction mixture was purified by flash silica chromatography to afford 4-(3-methylsulfamoyl-5-tri-fluoromethyl-phenyl)-6-(3-oxo-propyl)-pyrimidine-2-carbonitrile as a pink oil (300 mg). MS m/z 399.0 (M+1), 100%.

From this aldehyde, the following compound was synthesised by using reductive amination method as previously described as in EXAMPLE 7a B: 4-(3-Dimethylsulfamoyl-5-trifluoromethyl-phenyl)-6-(3-piperidin-1-yl-propyl)-Pyrimidine-2-carbonitrile $^1$H NMR (CDCl$_3$): δ 8.75 (s, 1H), 8.60 (s, 1H), 8.28 (s, 1H), 7.88 (s, 1H), 2.98 (t, 2H), 2.77 (s, 3H), 2.35-2.50 (br m, 6H), 2.02-2.08 (m, 2H), 1.42-1.66 (br m, 6H). MS m/z 468.0 (M+1), 100%.

EXAMPLE 23

4-(4-Methoxy-3-trifluoromethyl-phenyl)-6-propyl-pyrimidine-2-carbonitrile

Bis(triphenylphosphine)palladium dichloride (34 mg, 0.05 mmol) was added under a nitrogen atmosphere to a mixture of 4-propyl-6-trimethylstannanyl-pyrimidine-2-carbonitrile (150 mg, 0.48 mmol) and 4-methoxy-3-trifluoromethyl-bromobenzene (148 mg, 0.58 mmol) in dimethylformamide (3 mL). The mixture was heated for 5 hours at 80° C. then concentrated under reduced pressure. The residue was partitioned between ethyl acetate and water. The aqueous layer was extracted twice with ethyl acetate. The combined organic layers were concentrated under reduced pressure. The residue was chromatographed over silica gel (eluent Cyclohexane/DCM 7/3) to afford a solid which was triturated in pentane. After filtration, 4-(4-methoxy-3-trifluoromethyl-phenyl)-6-propyl-pyrimidine-2-carbonitrile (18 mg, 11%) was obtained as an off white solid.

$^1$H NMR (CDCl$_3$) δ: 8.34 (d, J=8 Hz, 1H); 8.30 (s, 1H); 7.65 (s, 1H); 7.15 (s, 1H) 4.01 (s, 3H); 2.92 (t, J=8 Hz, 2H); 1.95-1.85 (m, 2H); 1.05 (t, J=7 Hz, 3H).

MS m/z: 322.1 (M+1).

EXAMPLE 24

4-(5-tert-butyl-2-methoxy-phenyl)-6-propyl-pyrimidine-2-carbonitrile

A: 1-tert-Butyl-4-methoxy-3-iodobenzene $^1$H NMR (CDCl$_3$) δ: 7.76 (d, J=2 Hz, 1H); 7.30 (dd, J=8 Hz, J'=2 Hz, 1H); 6.74 (d, J=8 Hz, 1H); 3.83 (s, 3H); 1.28 (s, 9H).

$^{13}$C NMR (CDCl$_3$) δ: 155.8, 145.5, 136.3, 126.3, 110.4, 85.9, 56.3, 34.0, 31.4.

B: 4-(5-tert-butyl-2-methoxy-phenyl)-6-propyl-pyrimidine-2-carbonitrile $^1$H NMR (CDCl$_3$) δ: 8.05 (s, 1H); 7.99 (s, 1H); 7.51 (d, J=8 Hz, 1H); 6.97 (d, J=8 Hz, 1H); 3.90 (s, 3H); 2.81 (t, J=8 Hz, 2H); 1.85-1.75 (m, 2H); 1.36 (s, 9H); 1.01 (t, J=8 Hz, 3H).

MS m/z: 310 (M+1).

EXAMPLE 25

4-(3-Cyclopropyl-phenyl)-6-propyl-pyrimidine-2-carbonitrile

A: 3-Bromo-1-cyclopropyl-benzene

Iodine (0.335 g, 1.32 mmol), diiodomethane (4.3 mL, 53.0 mmol) and 3-bromostyrene (5 g, 26.4 mmol) were added successively to a suspension of copper (7.5 g, 118.8 mmol) in toluene (50 mL). The mixture was refluxed for 140 h, then filtered and concentrated in vacuo. The residue was distilled under reduced pressure to afford 3-bromo-1-cyclopropylbenzene (0.55 g, 10%) as a colorless oil.

$^1$H NMR (CDCl$_3$) δ: 7.35-7.25 (m, 1H); 7.25-7.20 (m, 1H); 7.15-7.05 (m, 1H); 7.05-6.95 (m, 1H); 1.95-1.85 (m, 1H); 1.05-0.95 (m, 2H); 0.75-0.65 (m, 2H).

B: 4-(3-Cyclopropyl-phenyl)-6-propyl-pyrimidine-2-carbonitrile $^1$H NMR (CDCl$_3$) δ: 7.85-7.80 (m, 2H); 7.68 (s, 1H); 7.41 (t, J=8 Hz, 1H); 7.30-7.20 (m, 1H); 2.84 (t, J=8 Hz, 2H); 2.05-2.95 (m, 1H); 1.90-1.80 (m, 2H); 1.10-0.95 (m, 5H); 0.80-0.75 (m, 2H).

MS m/z: 264 (M+1).

HPLC (200-400 nm): 92.2%.

EXAMPLE 26a 4-(3,4-dimethoxy-phenyl)-6-propyl-pyrimidine-2-carbonitrile

A: 4-iodo-6-propyl-pyrimidine-2-carbonitrile

Iodine (1.64 g, 6.5 mmol) was added at room temperature to a solution of 4-propyl-6-trimethylstannanyl-pyrimidine-2-carbonitrile (2.0 g, 6.5 mmol) in THF (100 mL). The mixture was stirred at room temperature for 2 hours, then diluted with a saturated solution of sodium thiosulfate and the THF was removed under reduced pressure. The aqueous layer was extracted with ethyl acetate (3×100 ml). The combined organic layers were washed with brine, dried over sodium sulphate, filtered and concentrated under reduced pressure. The residue was chromatographed over silica gel (eluent: Cyclohexane/Ethyl acetate 5/5) to afford 4-iodo-6-propyl-pyrimidine-2-carbonitrile (1.28 g, 72%) as a colorless oil.

$^1$H NMR (CDCl$_3$) δ: 7.81 (s, 1H); 2.71 (t, J=8 Hz, 2H); 1.8-1.7 (m, 2H); 0.99 (t, J=8 Hz, 3H).

$^{13}$C NMR (CDCl$_3$) δ: 172.0, 143.7, 134.2, 129.2, 114.7, 38.8, 21.8, 13.7.

MS m/z; 274 (M+1).

B: 4-(3,4-dimethoxy-phenyl)-6-propyl-pyrimidine-2-carbonitrile

Under nitrogen atmosphere, a solution (c=0.18 M) of 4-iodo-6-propyl-pyrimidine-2-carbonitrile (1 mL, 0.18 mmol) in degassed toluene, an aqueous solution (c=2 M) of potassium carbonate (0.225 mL, 0.45 mmol) and tetrakis-(triphenylphosphine) palladium (10 mg, 0.09 mmol) were successively added to a solution (c=0.216 M) of 3,4-dimethoxyphenyl boronic acid (1 ml, 0.216 mmol) in degassed toluene. The mixture was heated at 105° C. for 4 h, then was allowed to cool to room temperature and mixed with water (4 mL). The organic layer was evaporated under reduced pressure. The residue was chromatographed by preparative HPLC (H2O+0.05% TFA/CH3CN+0.05% TFA) to afford 4-(3,4-dimethoxy-phenyl)-6-propyl-pyrimidine-2-carbonitrile (28 mg).

$^1$H NMR (CDCl$_3$) δ: 7.75 (s, 1H); 7.66 (d, J=8 Hz, 1H); 7.63 (s, 1H); 6.97 (d, J=8 Hz, 1H); 4.02 (s, 3H); 3.97 (s, 3H); 2.82 (t, J=8 Hz, 2H); 1.85-1.75 (m, 2H); 1.02 (t, J=7 Hz, 3H). MS m/z: 284 (M+1).

The above described procedure was applied, using the appropriate boronic acid derivatives in the synthesis of the following derivatives:

26b: 4-(2,3-Dihydro-benzofuran-5-yl)-6-propyl-pyrimidine-2-carbonitrile $^1$H NMR (CDCl$_3$) δ: 8.1-8.0 (m, 1H); 7.9-7.8 (m, 1H); 7.58 (s, 1H); 6.9-6.8 (m, 1H); 4.7-4.6 (m, 2H); 3.35-3.25 (m, 2H); 2.85-2.70 (m, 2H); 1.9-1.8 (m, 2H); 1.00 (t, J=8 Hz, 3H). MS m/z: 266 (M+1).

26c: 4-(3-Cyano-phenyl)-6-propyl-pyrimidine-2-carbonitrile $^1$H NMR (CDCl$_3$) δ: 8.4-8.3 (m, 2H); 7.86 (d, J=8 Hz, 1H); 7.73 (s, 1H); 7.69 (t, J=8 Hz, 1H); 2.89 (t, J=8 Hz, 2H); 1.9-1.8 (m, 2H); 1.04 (t, J=8 Hz, 3H). MS m/z: 249 (M+1).

26d: 4-(3-Chloro-phenyl)-6-propyl-pyrimidine-2-carbonitrile $^1$H NMR (CDCl$_3$) δ: 8.10 (s, 1H); 7.99 (d, J=8 Hz, 1H); 7.67 (s, 1H); 7.55-7.45 (m, 2H); 2.86 (t, J=8 Hz, 2H); 1.9-1.8 (m, 2H); 1.03 (t, J=8 Hz, 3H). MS m/z: 258/260 (M+1).

26e: 4-(4-Dimethylamino-phenyl)-6-propyl-pyrimidine-2-carbonitrile $^1$H NMR (CDCl$_3$) δ: 8.03 (d, J=8 Hz, 2H); 7.53 (s, 1H); 6.75 (d, J=8 Hz, 2H); 3.08 (s, 6H); 2.76 (t, J=8 Hz, 2H); 1.9-1.8 (m, 2H); 1.00 (t, J=8 Hz, 3H). MS m/z: 267 (M+1).

26f: 4-(2,3-Dihydro-benzo[1,4]dioxin-6-yl)-6-propyl-pyrimidine-2-carbonitrile $^1$H NMR (CDCl$_3$) δ: 7.7-7.6 (m, 2H); 7.58 (s, 1H); 6.98 (d, J=8 Hz, 1H); 4.35-4.25 (m, 4H); 2.80 (t, J=8 Hz, 2H); 1.85-1.75 (m, 2H); 1.01 (t, J=8 Hz, 3H). MS m/z: 282 (M+1).

26n: 4-Propyl-6-(4-trifluoromethyl-phenyl)-pyrimidine-2-carbonitrile $^1$H NMR (CDCl$_3$) δ: 8.23 (d, J=8 Hz, 2H); 7.80 (d, J=8 Hz, 2H); 7.75 (s, 1H); 2.88 (t, J=8 Hz, 2H); 1.9-1.8 (m, 2H); 1.04 (t, J=8 Hz, 3H). MS m/z: 292 (M+1).

26h: 4-(2-Methoxy-phenyl)-6-propyl-pyrimidine-2-carbonitrile $^1$H NMR (CDCl$_3$) δ: 8.07 (d, J=8 Hz, 1H); 8.02 (s, 1H); 7.50-7.45 (m, 1H); 7.15-7.10 (m, 1H); 7.04 (d, J=8 Hz, 1H); 3.93 (s, 3H); 2.82 (t, J=8 Hz, 2H); 1.9-1.8 (m, 2H) 1.02 (t, J=8 Hz, 3H). MS m/z: 254 (M+1).

26i: 4-propyl-6-(2-trifluoromethyl-phenyl)-pyrimidine-2-carbonitrile $^1$H NMR (CDCl$_3$) δ: 7.83 (d, J=8 Hz, 1H); 7.75-7.50 (m, 2H); 7.54 (d, J=8 Hz, 1H); 7.49 (s, 1H); 2.87 (t, J=8 Hz, 2H); 1.9-1.8 (m, 2H); 1.01 (t, J=8 Hz, 3H). MS m/z: 292 (M+1).

26j: 4-(3-Acetyl-phenyl)-6-propyl-pyrimidine-2-carbonitrile $^1$H NMR (CDCl$_3$) δ: 8.67 (s, 1H); 8.37 (d, J=8 Hz, 1H); 8.14 (d, J=8 Hz, 1H); 7.80 (s, 1H); 7.67 (t, J=8 Hz, 1H); 2.88 (t, J=8 Hz, 2H); 2.72 (s, 3H); 1.9-1.8 (m, 2H); 1.03 (t, J=8 Hz, 3H). MS m/z: 266 (M+1)

26k: 4-(4-Isopropyl-phenyl)-6-propyl-pyrimidine-2-carbonitrile $^1$H NMR (CDCl$_3$) δ: 8.04 (d, J=8 Hz, 2H); 7.67 (s, 1H); 7.39 (d, J=8 Hz, 2H); 3.05-2.95 (m, 1H); 2.83 (t, J=8 Hz, 2H); 1.9-1.8 (m, 2H); 1.30 (s, 3H); 1.29 (s, 3H); 1.02 (t, J=8 Hz, 3H). MS m/z: 266 (M+1).

26l: 4-(Benzo[1,3]dioxol-5-yl)-6-propyl-pyrimidine-2-carbonitrile $^1$H NMR (CDCl$_3$) δ: 7.68 (d, J=8 Hz, 1H); 7.62 (s, 1H); 7.58 (s, 1H); 6.94 (d, J=8 Hz, 1H); 6.08 (s, 2H); 2.81 (t, J=8 Hz, 2H); 1.85-1.75 (m, 2H); 1.01 (t, J=8 Hz, 3H). MS m/z: 268 (M+1).

26m: 4-(3-Nitro-phenyl)-6-propyl-pyrimidine-2-carbonitrile $^1$H NMR (CDCl$_3$) δ: 8.92 (s, 1H); 8.53 (d, J=8 Hz, 1H); 8.43 (d, J=8 Hz, 1H); 7.81 (s, 1H); 7.77 (t, J=8 Hz, 1H); 2.91 (t, J=8 Hz, 2H); 1.9-1.8 (m, 2H); 1.05 (t, J=8 Hz, 3H). MS m/z: 269 (M+1).

26n: 4-(3-Chloro-4-fluoro-phenyl)-6-propyl-pyrimidine-2-carbonitrile $^1$H NMR (CDCl$_3$) δ: 8.21 (d, J=8 Hz, 1H); 8.1-8.0 (m, 1H); 7.66 (s, 1H); 7.35-7.20 (m, 1H); 2.9-2.8 (m, 2H); 1.90-1.75 (m, 2H); 1.03 (t, J=7 Hz, 3H). MS m/z: 266 (M+1).

26o: 4-(2,5-Dimethoxy-phenyl)-6-propyl-pyrimidine-2-carbonitrile $^1$H NMR (CDCl$_3$) δ: 8.07 (s, 1H); 7.66 (d, J=3 Hz, 1H); 7.05 (dd, J=8 Hz, J'=3 Hz, 1H); 6.97 (d, J=8 Hz, 1H); 3.88 (s, 3H); 3.87 (s, 3H); 2.82 (t, J=8 Hz, 2H); 1.85-1.75 (m, 2H); 1.02 (t, J=7 Hz, 3H). MS m/z: 284 (M+1).

EXAMPLE 27a

4-(2-Chloro-5-trifluoromethyl-phenyl)-6-propyl-pyrimidine-2-carbonitrile

Under nitrogen atmosphere, a solution (c=0.18 M) of 4-iodo-6-propyl-pyrimidine-2-carbonitrile (1 mL, 0.18 mmol) in degassed toluene, an aqueous solution (c=2 M) of potassium carbonate (0.225 mL, 0.45 mmol) and tetrakis (triphenylphosphine) palladium (10 mg, 0.09 mmol) were successively added to a solution (c=0.216 M) of 2-chloro-5-(trifluoromethyl)phenyl boronic acid (1 ml, 0.216 mmol) in degassed toluene. The mixture was heated at 105° C. for 4 h, then was allowed to cool to room temperature and mixed with water (4 mL). The organic layer was evaporated under reduced pressure. The residue was chromatographed by preparative HPLC (H2O+0.05% TFA/CH3CN+0.05% TFA) to afford 4-(2-chloro-5-trifluoromethyl-phenyl)-6-propyl-pyrimidine-2-carbonitrile (34 mg, 58%) as a solid.

$^1$H NMR (CDCl$_3$) δ: 7.99 (s, 1H); 7.78 (s, 1H); 7.7-7.6 (m, 2H); 2.89 (t, J=8 Hz, 2H); 1.90-1.80 (m, 2H); 1.03 (t, J=8 Hz, 3H).

MS m/z: 326/328 (M+1).

The above described procedure was applied, using the appropriate aryl boronic acid derivatives in the synthesis of the following derivatives:

27b: 4-(3-Methanesulfonyl-phenyl)-6-propyl-pyrimidine-2-carbonitrile $^1$H NMR (CDCl$_3$) δ: 8.63 (s, 1H); 8.48 (d, J=8 Hz, 1H); 8.14 (d, J=8 Hz, 1H); 7.80-7.75 (m, 2H); 3.15 (s, 3H); 2.89 (t, J=8 Hz, 2H); 1.9-1.8 (m, 2H); 1.04 (t, J=8 Hz, 3H). MS m/z: 308/310 (M+1).

EXAMPLE 28

4-(3-Cyclopentyl-phenyl)-6-propyl-pyrimidine-2-carbonitrile

A: N,N-dibenzyl-3-cyclopentyl-aniline

A solution of bromo cyclopentane (7.62 g, 51.1 mmol) in dry THF (25 ml) was added dropwise to a suspension of magnesium turnings (1.24 g, 51 mmol) in ether (3 ml) under nitrogen at such a rate so to maintain the inner temperature between 45 to 50° C. (After addition of a few drops of solution the mixture was heated to about 50° C. to initiate the Grignard reagent formation) After 1.5 h the Grignard reagent was canulated into a dropping funnel, diluted with 25 ml of dry THF and added dropwise over 30 minutes to a cold (0° C.) solution of dried ZnBr$_2$ (11.5 g, 51 mmol) in dry THF (90 ml) under a nitrogen atmosphere. After 15 minutes the reaction mixture was cooled to −60° C. and PdCl$_2$(dppf)$_2$ (249 mg, 0.34 mmol) was added (the solution became red). A solution of 3-bromo-N,N-Dibenzyl-aniline (6 g, 17 mmol) in dry THF (50 ml) was added to this solution over 35 minutes. The dry ice bath was then removed and the solution was allowed to warm to room temperature overnight. After addition of 3N HCl (70 ml), the THF was removed under reduced pressure. The aqueous residue was extracted three times with AcOEt (3×70 ml). The combined organic layers were washed with brine (50 ml), then with a saturated NaHCO$_3$ solution (50 ml). The insoluble material was filtered off and the solution was washed again with brine (50 ml). The organic layer was dried over MgSO$_4$ and concentrated under reduced pressure to give the above titled compound (5.8 g) which was used in the next step without any further purification.

$^1$H NMR (CDCl$_3$) δ: 7.28-7.32 (4H, m), 7.21-7.25 (6H, m), 7.08 (1H, t, J=8 Hz), 6.60-6.64 (2H, m), 6.55 (1H, dd, J$_1$=8 Hz, J$_2$=2.4 Hz), 4.62 (4H, s), 2.85 (1H, quint), 1.90-2.00 (2H, m), 1.65-1.75 (2H, m), 1.5-1.65 (2H, m), 1.45-1.5 (2H, m).

B: 3-cyclopentyl-aniline Hydrochloride

N,N-Dibenzyl-3-cyclopentyl-aniline (6.07 g, 17.03 mmol) was hydrogenated over Pd(OH)$_2$ (600 mg) under 10 bars in a mixture of MeOH (80 ml), methoxyethanol (20 ml), CH$_2$Cl$_2$ (20 ml) and concentrated HCl (1.63 ml) for 20 h, The catalyst was removed by filtration and the solvent was removed under reduced pressure. The residue was partitioned between CH$_2$Cl$_2$ and water. The pH was set to about 10 by adding NaOH in pellets. The organic layer was washed with brine, dried over MgSO$_4$ and concentrated under reduced pressure to give 2.65 g of the expected aniline. The hydrochloride was obtained by treatment with ethereal HCl: 2.38 g, yield: 71%. HPLC: 100%.

$^1$H NMR (CD$_3$OD) δ: 7.44 (1H, t, J=8 Hz), 7.38 (H, d, J=8 Hz), 7.29 (1H, s), 7.21 (1H, m), 3.08 (1H, quint), 2.09-2.13 (2H, m), 1.83-1.86 (2H, m), 1.73-1.76 (2H, m), 1.60-1.63 (2H, m).

C: 1-cyclopentyl-3-iodo-benzene

A solution of sodium nitrite (558 mg, 8.1 mmol) in water (10 ml) was added over 5 minutes to a cooled (5° C.) solution of 3-cyclopentyl-aniline hydrochloride (1 g, 5.1 mmol) in 6N HCl (25 ml). After 50 minutes, a solution of potassium iodide (2.02 g, 12.2 mmol) in water (10 ml) was added over 5 minutes. The mixture was then heated for 1 h at 70° C. After cooling down to room temperature, the pH was set over 11 with 6N NaOH, and the mixture was extracted three times with CH$_2$Cl$_2$ (3×100 ml). The combined organic layers were washed with sodium thiosulfate (75 ml) then brine (75 ml) and dried over MgSO$_4$. The solvent was removed under reduced pressure to give 1.23 g of crude material (HPLC: 67%) which was purified by chromatography over silica gel (eluent:cyclohexane) to yield the above titled compound as an oil: 825 mg, yield: 60%.

$^1$H NMR (CDCl$_3$) δ: 7.58 (1H, m), 7.50 (1H, d, J=8 Hz), 7.19 (1H, br d), 7.00 (1H, t, J=8 Hz), 2.92 (1H, quint), 2.03-2.07 (2H, m), 1.76-1.82 (2H, m), 1.65-1.70 (2H, m), 1.54-1.57 (2H, m).

D. 4-(3-cyclopentyl-phenyl)-6-propyl-pyrimidine-2-carbonitrile

A mixture of 1-cyclopentyl-3-iodo-benzene (158 mg, 0.58 mmol), 4-propyl-6-trimethylstannanyl-pyrimidine-2-carbonitrile (150 mg, 0.48 mmol) and PdCl$_2$(PPh$_3$)$_2$ (34 mg, 0.05 mmol) in dry DMF (3 ml) was heated to 80° C. for 6 h under a nitrogen atmosphere. More catalyst (40 mg, 0.06 mmol) was added and the mixture was heated for 12 h at 80° C. The solvent was removed under reduced pressure and the residue was partitioned between water (5 ml) and AcOEt (5 ml). The aqueous layer was extracted twice with AcOEt (2×5 ml). The combined organic layers were washed with brine, dried over MgSO$_4$ and concentrated under reduced pressure to give 272 mg of crude product which was purified by silica gel chromatography (eluent:cyclohexane/AcOEt 95/5) to give the above titled compound: 51 mg, yield: 36%, HPLC: 98%.

$^1$H NMR (CDCl$_3$) δ: 7.99 (1H, s), 7.87 (1H, dt, J$_1$=5 Hz, J$_2$=2 Hz), 7.69 (1H, s), 7.44 (2H, d, J=5 Hz), 3.10 (1H, quint), 2.84 (2H, t, J=7.6 Hz), 2.12-2.15 (2H, m), 1.81-1.88 (4H, m), 1.60-1.76 (4H, m), 1.02 (3H, t, J=7.2 Hz). MS m/z: 292 (M+1).

EXAMPLE 29a

4-(3-Cyclopropylamino-propyl)-6-(3-trifluoromethylphenyl)-pyrimidine-2-carbonitrile To a solution of 4-(3-oxo-propyl)-6-(3-trifluoromethylphenyl)-pyrimidine-2-carbonitrile (153 mg) in methanol (2 ml) was added cyclopropylamine (140 μL), acetic acid (0.12 mL), and followed by sodium triacetoxyborohydride (210 mg). The mixture was stirred at room temperature for 24 hours, then purified by preparative-HPLC. 4-(3-cyclopropylamino-propyl)-6-(3-trifluoromethylphenyl)-pyrimidine-2-carbonitrile TFA salt was isolated as a white solid (70 mg).

¹H NMR (MeOD): δ 8.50 (s, 1H), 8.47 (d, 1H), 8.25 (s, 1H), 7.90 (d, 1H), 7.81 (t, 1H), 3.28 (t, 2H), 3.09 (t, 2H), 2.80 (m, 1H), 2.25 (m, 2H), 0.85-1.05 (m, 4H). MS m/z 347.4 (M+1), 30%.

29b: 4-[3-(1-(s)-Methyl-2-methoxyethylamino)-propyl]-6-(3-trifluoromethylphenyl)-pyrimidine-2-carbonitrile To a solution of 4-(3-oxo-propyl)-6-(3-trifluoromethylphenyl)-pyrimidine-2-carbonitrile (610 mg) in methanol (8 ml) was added 1-(s)-methyl-2-methoxyethylamine (0.85 mL), acetic acid (0.5 mL), and followed by sodium triacetoxyborohydride (0.82 g). The mixture was stirred at room temperature for 4 hours, then diluted with sodium bicarbonate aqueous solution (5%, 50 ml). The mixture was extracted with ethyl acetate (50 ml plus 3×20 ml). Combined organic layer was dried over sodium sulphate, filtered, solvent removed under vacuum. Residue was columned on silica gel using DCM-MeOH (20:1) as eluant to give 4-[3-(1-(s)-methyl-2-methoxyethylamino)-propyl]-6-(3-trifluoromethylphenyl)-pyrimidine-2-carbonitrile (250 mg). The above neutral product was dissolved in DCM and then HCl (1M in ether, 1 ml) added, 4-[3-(1-(s)-methyl-2-methoxyethylamino)-propyl]-6-(3-trifluoromethylphenyl)-pyrimidine-2-carbonitrile HCl salt was collected by filtration (180 mg). ¹H NMR (MeOD): δ 8.50 (s, 1H), 8.48 (d, 1H), 8.27 (s, 1H), 7.90 (d, 1H), 7.79 (t, 1H), 3.68 (m, 1H), 3.48 (m, 2H), 3.43 (s, 3H), 3.17 (m, 2H), 3.10 (t, 2H), 2.25 (m, 2H), 1.36 (d, 3H). MS m/z 379.5 (M+1), 80%.

The procedure described above was further applied, using the appropriate amine derivatives, to prepare the following compounds:

29c: 4-[3-(1-(S)-Carbamoyl-ethylamino)-propyl]-6-(3-trifluoromethylphenyl)-pyrimidine-2-carbonitrile ¹H NMR (MeOD): δ 8.51 (s, 1H), 8.48 (d, 1H), 8.22 (s, 1H), 7.88 (d, 1H), 7.77 (t, 1H), 3.29 (m, 1H), 3.01 (t, 2H), 2.70 (t, 2H), 2.05 (m, 2H), 1.32 (d, 3H). MS m/z 377.9 (M+1). 100%.

29d: 4-[3-(1-(R)-Carbamoyl-ethylamino)-propyl]-6-(3-trifluoromethyl-phenyl)-pyrimidine-2-carbonitrile ¹H NMR (MeOD): δ 8.51 (s, 1H), 8.48 (d, 1H), 8.22 (s, 1H), 7.88 (d, 1H), 7.77 (t, 1H), 3.23 (q, 1H), 3.00 (t, 2H), 2.65 (t, 2H), 2.05 (m, 2H), 1.28 (d, 3H). MS m/z 378.4 (M+1), 100%.

29e: 4-[3-(1-Ethyl-1-methyl-propylamino)-propyl]-6-(3-trifluoromethylphenyl)-pyrimidine-2-carbonitrile Trifluoroacetic Acid (1:1) Salt ¹H NMR (MeOD): δ 8.54 (s, 1H), 8.48 (d, 1H), 8.24 (s, 1H), 7.90 (d, 1H), 7.79 (t, 1H), 3.12 (m, 4H), 2.27 (m, 2H), 1.76 (m, 4H), 1.32 (s, 3H), 0.99 (t, 6H). MS m/z 391.3 (M+1), 100%.

29f: 4-[3-(1-Methyl-cyclopropylamino)-propyl]-6-(3-trifluoromethylphenyl)-pyrimidine-2-carbonitrile Trifluoroacetic Acid (1:1) Salt ¹H NMR (CDCl₃): δ 9.13 (bs, 2H), 8.36 (s, 1H), 8.31 (d, 1H), 7.83 (s, 1H), 7.82 (d, 1H), 7.68 (t, 1H), 3.24 (m, 2H), 3.04 (t, 2H), 2.28 (m, 2H), 1.50 (s, 3H), 1.21 (t, 2H), 0.74 (t, 2H). MS m/z: 361.1 (M+1), 27%.

29g: 4-[3-(2-Hydroxy-ethylamino)-propyl]-6-(3-trifluoromethylphenyl)-pyrimidine-2-carbonitrile; Trifluoroacetic Acid (1:1) Salt ¹H NMR (CDCl₃): δ 9.04 (bs, 2H), 8.34 (s, 1H), 8.29 (d, 1H), 7.84 (s, 1H), 7.81 (d, 1H), 7.66 (t, 1H), 4.00 (m, 2H), 3.22 (m, 4H), 3.05 (t, 2H), 2.34 (m, 2H). MS m/z: 351.3 (M+1), 20%.

29h: 4-[3-(1-Carbamoyl-1-methyl-ethylamino)-propyl]-6-(3-trifluoromethylphenyl)-pyrimidine-2-carbonitrile ¹H NMR (MeOD): δ 8.55 (s, 1H), 8.48 (d, 1H), 8.22 (s, 1H), 7.90 (d, 1H), 7.79 (t, 1H), 3.03 (t, 2H), 2.74 (t, 2H), 2.02-2.12 (m, 2H), 1.39 (s, 6H). MS m/z 392.0 (M+1), 100%.

29i: 4-[3-(2-Oxo-pyrrolidin-3-(S)-ylamino)-propyl]-6-(3-trifluoromethylphenyl)-pyrimidine-2-carbonitrile Trifluoroacetic Acid (1:1) Salt ¹H NMR (MeOD): δ 8.52 (s, 1H), 8.48 (d, 1H), 8.25 (s, 1H), 7.91 (d, 1H), 7.80 (t, 1H), 4.12 (t, 1H), 3.38-3.47 (m, 3H), 3.20-3.27 (m, 1H), 3.10 (t, 2H), 2.60-2.68 (m, 1H), 2.11-2.35 (m, 3H). MS m/z 390.3 (M+1), 100%.

EXAMPLE 30

Assay Procedures

Cathepsin K Activity.

The inhibitory activity of the compounds of the invention was demonstrated in vitro by measuring the inhibition of recombinant human Cathepsin K as follows:

To a 384 well microtitre plate is added 5 μl of a 100 μM solution of test compound in assay buffer (100 mM sodium acetate pH5.5, 5 mM EDTA, 5 mM dithiothreitol) with 10% dimethylsulfoxide (DMSO), plus 10 μl of 100 μM solution of the substrate Z-Phe-Arg-AMC (Bachem; 7-amido-coumarine derivative of the dipeptide N-benzyloxycarbonyl-Phe-Arg-OH) in assay buffer and 25 μl of assay buffer. 10 μl of a 1 mg/l solution of activated recombinant human cathepsin K, in assay buffer, is then added to the well, yielding a final inhibitor concentration of 10 μM.

Enzyme activity is determined by measuring the fluorescence of the liberated aminomethylcoumarin at 440 μM using 390 μM excitation, at 10 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention typically have a $pIC_{50}$ (negative logarithm of the $IC_{50}$ concentration) for inhibition of human cathepsin K of more than 6, preferably more than 7 such as for the compounds of Examples 1, 2, 4h, and most preferably a $pIC_{50}$ of more than 8, such as for the compounds of Examples 3, 4a, 4d, 4e, 4f, 4g, 4i, 4r, 4s, 4u, 4a', 8a, 8c, 14j, 14n.

Cathepsin S Activity.

The inhibitory activity of the compounds of the invention was demonstrated in vitro by measuring the inhibition of recombinant human Cathepsin S as follows:

To a 384 well microtitre plate is added 10 μl of a 100 μM solution of test compound in assay buffer (100 mM sodium acetate pH5.5, 5 mM EDTA, 5 mM dithiothreitol) with 10% dimethylsulfoxide (DMSO), plus 20 μl of 250 μM solution of the substrate Z-Val-Val-Arg-AMC (Bachem; 7-amido-coumarine derivative of the tripeptide N-benzyloxycarbonyl-Val-Val-Arg-OH) in assay buffer and 45 µd of assay buffer. 25 µl of a 2 mg/l solution of activated recombinant human cathepsin S, in assay buffer, is then added to the well, yielding a final inhibitor concentration of 10 µM.

Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity).

The invention claimed is:

1. A 4-phenyl-pyrimidine-2-carbonitrile compound having the general formula I

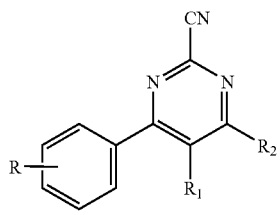

Formula I wherein
- R represents 1-3 optional substituents independently selected from $(C_{1-6})$alkyl (optionally substituted with one or more halogens), $(C_{1-6})$alkyloxy (optionally substituted with one or more halogens), cyano, halogen, hydroxy, nitro, $(C_{3-6})$cycloalkyl, $CO(C_{1-6})$alkyl, $S(C_{1-6})$alkyl, $SO(C_{1-6})$alkyl, $SO_2(C_{1-6})$alkyl, $SO_2NH(C_{1-8})$alkyl, $SO_2NH_2$, $NHCO(C_{1-8})$alkyl and $CO_2H$; or 2 substituents R on adjacent positions represent together $OCH_2O$, $OCH_2CH_2O$ or $CH_2CH_2O$;
- $R^1$ is H or $(C_{1-6})$alkyl;
- $R^2$ is $(C_{2-6})$alkyl, optionally substituted with OH, $(C_{1-4})$alkyloxy, $(C_{6-10})$aryloxy, $(C_{6-10})$aryl$(C_{1-4})$alkyloxy, one or more halogens, $NR_3R_4$, $CO_2H$ or $CONR_6R_7$;
- $R_3$ and $R_4$ are independently H, $(C_{1-8})$alkyl [optionally substituted with one or more halogens, $(C_{1-4})$alkyloxy or $(C_{6-10})$aryloxy], $(C_{3-8})$cycloalkyl [optionally substituted with one or more halogens], $(C_{1-4})$alkyl substituted with a 4-8 membered saturated heterocyclic ring comprising a heteroatom selected from O, S and $NR_5$, a 4-8 membered saturated heterocyclic ring comprising a heteroatom selected from O, S and $NR_5$, $(C_{6-10})$aryl, $(C_{2-9})$heteroaryl [optionally substituted with 1-3 substituents selected from halogen, $CF_3$, $(C_{1-4})$alkyl and $(C_{1-4})$alkyloxy], $(C_{6-10})$aryl$(C_{1-4})$alkyl or $(C_{2-9})$heteroaryl$(C_{1-4})$alkyl; or
- $R_3$ and $R_4$ together with the nitrogen to which they are bound form a 4-8 membered saturated heterocyclic ring, optionally substituted with one or more halogens or with $CONR_8R_9$, and optionally further comprising 1 or more heteroatoms selected from O, S and $NR_5$; or
- $R_3$ is H or $(C_{1-4})$alkyl; and $R_4$ is $(C_{1-4})$alkyl substituted with $CONR_8R_9$, $COOR_{10}$, $NR_8$, $R_9$, $NR_8COR_9$, or $NR_8CONR_9R_{10}$;
- $R_5$ is H, $(C_{1-4})$alkyl [optionally substituted with $(C_{3-8})$cycloalkyl, $(C_{6-10})$aryl or $(C_{2-5})$heteroaryl], $(C_{3-8})$cycloalkyl, $(C_{6-10})$aryl or $(C_{2-5})$heteroaryl;
- $R_6$ and $R_7$ are independently H, $(C_{1-4})$alkyl or a 4-8 membered saturated heterocyclic ring comprising a heteroatom selected from O, S and $NR_5$; or
- $R_6$ and $R_7$ together with the nitrogen to which they are bound form a 4-8 membered saturated heterocyclic ring, optionally substituted with one or more halogens, and optionally further comprising 1 or more heteroatoms selected from O, S and $NR_5$;
- $R_8$ and $R_9$ are independently H or $(C_{1-4})$alkyl; or
- $R_8$ and $R_9$ together with the atoms to which they are bound form a 4-8 membered saturated heterocyclic ring, optionally comprising 1 or more heteroatoms selected from O, S and $NR_5$:
- $R_{10}$ is H or $(C_{1-4})$alkyl;

or a pharmaceutically acceptable salt thereof.

2. The 4-phenyl-pyrimidine-2-carbonitrile compound according to claim 1, wherein
- R represents 1-3 optional substituents independently selected from $(C_{1-6})$alkyl [optionally substituted with one or more halogens], $(C_{1-6})$alkyloxy [optionally substituted with one or more halogens], cyano and halogen;
- $R_1$ is H or $(C_{1-6})$alkyl;
- $R_2$ is $(C_{2-6})$alkyl, optionally substituted with OH, $(C_{1-4})$alkyloxy, one or more halogens, or $NR_3R_4$;
- $R_3$ and $R_4$ are independently H, $(Cp_{1-8})$alkyl [optionally substituted with one or more halogens], $(C_{3-8})$cycloalkyl [optionally substituted with one or more halogens], a 4-8 membered saturated heterocyclic ring comprising a heteroatom selected from O, S and $NR_5$, $(C_{6-10})$aryl, $(C_{2-9})$heteroaryl, $(C_{6-10})$aryl$(C_{1-4})$alkyl or $(C_{2-9})$heteroaryl$(C_{1-4})$alkyl; or
- $R_3$ and $R_1$ together with the nitrogen to which they are bound form a 4-8 membered saturated heterocyclic ring, optionally substituted with one or more halogens, and optionally further comprising 1 or more heteroatoms selected from O, S and $NR_5$;
- $R_5$ is H, $(C_{1-4})$alkyl [optionally substituted with $(C_{3-8})$cycloalkyl, $(C_{6-10})$aryl or $(C_{2-5})$heteroaryl], $(C_{3-8})$cycloalkyl, $(C_{6-10})$aryl or $(C_{2-5})$heteroaryl;

or a pharmaceutically acceptable salt thereof.

3. The 4-phenyl-pyrimidine-2-carbonitrile compound according to claim 2, wherein $R_2$ is $(C_{2-6})$alkyl substituted with OH, $(C_{1-4})$alkyloxy, one or more halogens, or $NR_3R_1$.

4. The 4-phenyl-pyrimidine-2-carbonitrile compound according to claim 2, wherein $R_2$ is propyl substituted at the 3-position with $NR_3R_4$.

5. The 4-phenyl-pyrimidine-2-carbonitrile compound according to claim 2, wherein the 4-phenyl group comprises a trifluoromethyl substituent at a meta position.

6. The 4-phenyl-pyrimidine-2-carbonitrile compound of formula I according to claim 1 which is selected from:

4-(3-hydroxy-1-propyl)-6-(3-trifluoromethylphenyl)-pyrimidine-2-carbonitrile;

(3-(piperidin-1-yl)propyl)-6-(3-trifluoromethylphenyl)-pyrimidine-2-carbonitrile;

[3-(1-ethyl-propylamino)-propyl]-6-(3-trifluoromethylphenyl)-pyrimidine-2-carbonitrile;

4-[3-(4-methyl-[1,4]diazepan-1-yl)-propyl]-6-(3-trifluoromethylphenyl)-pyrimidine-2-carbonitrile;

4-(3-cyclohexylamino-propyl)-6-(3-trifluoromethylphenyl)-pyrimidine-2-carbonitrile;

4-{3-[methyl-(1-methyl-piperidin-4-yl)-amino]-propyl}-6-(3-trifluoromethylphenyl)-pyrimidine-2-carbonitrile;

4-[3-(4-methyl-piperazin-1-yl)-propyl]-6-(3-trifluoromethylphenyl)-pyrimidine-2-carbonitrile;

4-(3-isopropylamino-propyl)-6-(3-trifluoromethylphenyl)-pyrimidine-2-carbonitrile;

4-[3-(4-pyridin-2-yl-piperazin-1-yl)-propyl]-6-(3-trifluoromethylphenyl)-pyrimidine-2-carbonitrile;
4-[3-(carbamoylmethylamino)-propyl]-6-(3-trifluoromethylphenyl)-pyrimidine-2-carbonitrile;
4-[3-(carboxymethylamino)-propyl]-6-(3-trifluoromethylphenyl)-pyrimidine-2-carbonitrile;
4-[3-(2-dimethylaminoethylamino)-propyl]-6-(3-trifluoromethylphenyl)-pyrimidine-2-carbonitrile;
4-[3-(2-acetylaminoethylamino)-propyl]-6-(3-trifluoromethylphenyl)-pyrimidine-2-carbonitrile;
4-{3-[2-(2-oxo-imidazolidin-1-yl)-ethylamino]-propyl}-6-(3-trifluoromethylphenyl)-pyrimidine-2-carbonitrile;
4-(3,4-dimethylphenyl)-6-[3-(methylcarbamoylmethylamino)-propyl]-pyrimidine-2-carbonitrile;
4-[3-(2-acetylaminoethylamino)-propyl]-6-(3,4-dimethylphenyl)-pyrimidine-2-carbonitrile;
4-[3-(3-dimethylamino-propylamino)-propyl]-6-(3,4-dimethyl-phenyl)-pyrimidine-2-carbonitrile;
4-(3,4-dimethylphenyl)-6-{3-[2-(1-methyl-pyrrolidin-2-yl)-ethylamino]-propyl}-pyrimidine-2-carbonitrile;
4-(3-cyclopropylamino-propyl)-6-(3-trifluoromethylphenyl)-pyrimidine-2-carbonitrile;
4-[3-(1-(s)-methyl-2-methoxyethylamino)-propyl]-6-(3-trifluoromethylphenyl)-pyrimidine-2-carbonitrile;
4-[3-(1-(S)-carbamoyl-ethylamino)-propyl]-6-(3-trifluoromethylphenyl)-pyrimidine-2-carbonitrile;
4-[3-(1-(R)-carbamoyl-ethylamino)-propyl]-6-(3-trifluoromethylphenyl)-pyrimidine-2-carbonitrile;
4-[3-(1-ethyl-1-methyl-propylamino)-propyl]-6-(3-trifluoromethylphenyl)-pyrimidine-2-carbonitrile;
4-[3-(1-methyl-cyclopropylamino)-propyl]-6-(3-trifluoromethylphenyl)-pyrimidine-2-carbonitrile;
4-[3-(2-hydroxyethylamino)-propyl]-6-(3-trifluoromethylphenyl)-pyrimidine-2-carbonitrile;
4-[3-(1-carbamoyl-1-methyl-ethylamino)-propyl]-6-(3-trifluoromethylphenyl)-pyrimidine-2-carbonitrile; and
4-[3-(2-oxo-pyrrolidin-3-(S)-ylamino)-propyl]-6-(3-trifluoromethylphenyl)-pyrimidine-2-carbonitrile; or a pharmaceutically acceptable salt thereof.

7. A pharmaceutical composition comprising a 4-phenyl-pyrimidine-2-carbonitrile compound according to claim 1, or a pharmaceutically acceptable salt thereof, in admixture with pharmaceutically acceptable auxiliaries.

8. The pharmaceutical composition according to claim 7, wherein the 4-phenyl-pyrimidine-2-carbonitrile compound of formula I is selected from:
4-(3-hydroxy-1-propyl)-6-(3-trifluoromethylphenyl)-pyrimidine-2-carbonitrile;
(3-(piperidin-1-yl)propyl)-6-(3-trifluoromethylphenyl)-pyrimidine-2-carbonitrile;
[3-(1-ethyl-propylamino)-propyl]-6-(3-trifluoromethylphenyl)-pyrimidine-2-carbonitrile;
4-[3-(4-methyl-[1,4]diazepan-1-yl)-propyl]-6-(3-trifluoromethylphenyl)-pyrimidine-2-carbonitrile;
4-(3-cyclohexylamino-propyl)-6-(3-trifluoromethylphenyl)-pyrimidine-2-carbonitrile;
4-{3-[methyl-(1-methyl-piperidin-4-yl)-amino]-propyl}-6-(3-trifluoromethylphenyl)-pyrimidine-2-carbonitrile;
4-[3-(4-methyl-piperazin-1-yl)-propyl]-6-(3-trifluoromethylphenyl)-pyrimidine-2-carbonitrile;
4-(3-isopropylamino-propyl)-6-(3-trifluoromethylphenyl)-pyrimidine-2-carbonitrile;
4-[3-(4-pyridin-2-yl-piperazin-1-yl)-propyl]-6-(3-trifluoromethylphenyl)-pyrimidine-2-carbonitrile;
4-[3-(carbamoylmethylamino)-propyl]-6-(3-trifluoromethylphenyl)-pyrimidine-2-carbonitrile;
4-[3-(carboxymethylamino)-propyl]-6-(3-trifluoromethylphenyl)-pyrimidine-2-carbonitrile;
4-[3-(2-dimethylaminoethylamino)-propyl]-6-(3-trifluoromethylphenyl)-pyrimidine-2-carbonitrile;
4-[3-(2-acetylaminoethylamino)-propyl]-6-(3-trifluoromethylphenyl)-pyrimidine-2-carbonitrile;
4-{3-[2-(2-oxo-imidazolidin-1-yl)-ethylamino]-propyl}-6-(3-trifluoromethylphenyl)-pyrimidine-2-carbonitrile;
4-(3,4-dimethylphenyl)-6-[3-(methylcarbamoylmethylamino)-propyl]-pyrimidine-2-carbonitrile;
4-[3-(2-acetylaminoethylamino)-propyl]-6-(3,4-dimethylphenyl)-pyrimidine-2-carbonitrile;
4-[3-(3-dimethylamino-propylamino)-propyl]-6-(3,4-dimethyl-phenyl)-pyrimidine-2-carbonitrile;
4-(3,4-dimethylphenyl)-6-{3-[2-(1-methyl-pyrrolidin-2-yl)-ethylamino]-propyl}-pyrimidine-2-carbonitrile;
4-(3-cyclopropylamino-propyl)-6-(3-trifluoromethylphenyl)-pyrimidine-2-carbonitrile;
4-[3-(1-(s)-methyl-2-methoxyethylamino)-propyl]-6-(3-trifluoromethylphenyl)-pyrimidine-2-carbonitrile;
4-[3-(1-(S)-carbamoyl-ethylamino)-propyl]-6-(3-trifluoromethylphenyl)-pyrimidine-2-carbonitrile;
4-[3-(1-(R)-carbamoyl-ethylamino)-propyl]-6-(3-trifluoromethylphenyl)-pyrimidine-2-carbonitrile;
4-[3-(1-ethyl-1-methyl-propylamino)-propyl]-6-(3-trifluoromethylphenyl)-pyrimidine-2-carbonitrile;
4-[3-(1-methyl-cyclopropylamino)-propyl]-6-(3-trifluoromethylphenyl)-pyrimidine-2-carbonitrile;
4-[3-(2-hydroxyethylamino)-propyl]-6-(3-trifluoromethylphenyl)-pyrimidine-2-carbonitrile;
4-[3-(1-carbamoyl-1-methyl-ethylamino)-propyl]-6-(3-trifluoromethylphenyl)-pyrimidine-2-carbonitrile; and
4-[3-(2-oxo-pyrrolidin-3-(S)-ylamino)-propyl]-6-(3-trifluoromethylphenyl)-pyrimidine-2-carbonitrile; or a pharmaceutically acceptable salt thereof.

9. The 4-phenyl-pyrimidine-2-carbonitrile compound according to claim 3, wherein $R_2$ is propyl substituted at the 3-position with $NR_3R_4$.

10. The 4-phenyl-pyrimidine-2-carbonitrile compound according to claim 3, wherein the 4-phenyl group comprises a trifluoromethyl substituent at a meta position.

11. The 4-phenyl-pyrimidine-2-carbonitrile compound according to claim 4, wherein the 4-phenyl group comprises a trifluoromethyl substituent at a meta position.

12. A method for the treatment of a cathepsin K and cathepsin S related disorders selected from atherosclerosis, rheumatoid arthritis and chronic pain in a human in need of treatment, the method comprising administering to the human an effective amount of the 4-phenyl-pyrimidine-2-carbonitrile compound according to claim 1, or pharmaceutically acceptable salt thereof.

13. The method according to claim 12, wherein the disorders is atherosclerosis.

14. The method according to claim 12, wherein disorder is rheumatoid arthritis.

15. The method according to claim 12, wherein the disorder is chronic pain.

16. The method according to claim 15, wherein the chronic pain is neuropathic pain.

17. 4-[3-(1-carbamoyl-1-methyl-ethylamino)-propyl]-6-(3-trifluoromethylphenyl)-pyrimidine-2-carbonitrile or a pharmaceutically acceptable salt thereof.

18. A pharmaceutical composition comprising the compound according to claim 17, or a pharmaceutically acceptable salt thereof in admixture with pharmaceutically acceptable auxiliaries.

19. A method for the treatment of a cathepsin K and cathepsin S disorder selected from atherosclerosis, rheumatoid arthritis and chronic pain in a human in need of treatment, the method comprising administering to the human an effective amount of the compound according to claim 17, or a pharmaceutically acceptable salt thereof.

20. The method according to claim 19, wherein the disorder is atherosclerosis.

21. The method according to claim 19, wherein the disorder is rheumatoid arthritis.

22. The method according to claim 19, wherein the disorder is chronic pain.

23. The method according to claim 19, wherein the chronic pain is neuropathic pain.

\* \* \* \* \*